US009245304B2

(12) United States Patent
Luciano, Jr. et al.

(10) Patent No.: US 9,245,304 B2
(45) Date of Patent: Jan. 26, 2016

(54) MANUFACTURING SEPARABLE POUCHES WITH A CENTER CUT BLADE

(75) Inventors: Robert A. Luciano, Jr., Reno, NV (US); Russell Bradford, Reno, NV (US); Leslie Baker, Reno, NV (US); Clay McElhany, Reno, NV (US)

(73) Assignee: EDGE MEDICAL PROPERTIES, LLC, Reno, NV (US)

( * ) Notice: Subject to any disclaimer, the term of this patent is extended or adjusted under 35 U.S.C. 154(b) by 333 days.

(21) Appl. No.: 12/424,483

(22) Filed: Apr. 15, 2009

(65) Prior Publication Data

US 2010/0069213 A1    Mar. 18, 2010

Related U.S. Application Data

(63) Continuation-in-part of application No. 11/923,321, filed on Oct. 24, 2007, now Pat. No. 8,266,878, which is a continuation-in-part of application No. 11/796,123, filed on Apr. 25, 2007, now Pat. No. 7,690,173, and a continuation-in-part of application (Continued)

(51) Int. Cl.
*B65B 61/00* (2006.01)
*G06Q 50/22* (2012.01)
*G06Q 10/08* (2012.01)

(52) U.S. Cl.
CPC .............. *G06Q 50/22* (2013.01); *G06Q 10/087* (2013.01)

(58) Field of Classification Search
USPC .......... 53/415, 450, 131.2, 135.3, 550, 131.4; 83/835, 697, 699.21, 746
See application file for complete search history.

(56) References Cited

U.S. PATENT DOCUMENTS

| 2,294,220 | A | * | 8/1942 | Albertson ................. 53/415 |
| 3,254,828 | A | * | 6/1966 | Hershey ..................... 383/37 |
| 3,432,951 | A | | 3/1969 | Cherrin |
| 3,497,982 | A | | 3/1970 | Schulz |
| 3,503,493 | A | * | 3/1970 | Nagy ......................... 206/232 |
| 3,703,955 | A | | 11/1972 | Inacker |
| 3,780,856 | A | | 12/1973 | Braverman |
| 3,921,804 | A | | 11/1975 | Tester |
| 3,933,245 | A | | 1/1976 | Mullen |
| 4,039,080 | A | | 8/1977 | Cappuccilli |
| 4,062,445 | A | | 12/1977 | Moe |
| 4,318,477 | A | | 3/1982 | Kerpe |
| 4,416,375 | A | * | 11/1983 | Braverman et al. ........ 206/534.1 |

(Continued)

FOREIGN PATENT DOCUMENTS

DE           3502647 A1    7/1986
WO    WO 96/13790 A1    5/1996

(Continued)

*Primary Examiner* — Sameh Tawfik
(74) *Attorney, Agent, or Firm* — Kerr IP Group, LLC; Michael A. Kerr

(57) ABSTRACT

A system for manufacturing a plurality of separable pouches comprising a means for forming sealed pouches, a center cut blade and a means for segregating each sealed pouch with the center cut blade is described. The means for forming the sealed pouches includes placing a plurality of different tablets corresponding to different medications into each sealed pouch. The center cut blade includes a side cut on each end of the blade, a center cut in the middle of the blade, and at least one perforation cut between each side cut and the center cut. The means for separating each sealed pouch with the center cut blade provides each sealed pouch with a sealed top end, a sealed bottom end, and two sides, in which at least one side is also sealed.

20 Claims, 40 Drawing Sheets

Related U.S. Application Data

No. 11/796,124, filed on Apr. 25, 2007, now Pat. No. 8,074,426, and a continuation-in-part of application No. 11/796,125, filed on Apr. 25, 2007, application No. 12/424,483, which is a continuation-in-part of application No. 11/241,783, filed on Sep. 30, 2005, now Pat. No. 8,123,036.

(60) Provisional application No. 61/045,160, filed on Apr. 15, 2008, provisional application No. 61/045,166, filed on Apr. 15, 2008, provisional application No. 61/045,171, filed on Apr. 15, 2008, provisional application No. 60/795,370, filed on Apr. 26, 2006, provisional application No. 60/795,446, filed on Apr. 26, 2006, provisional application No. 60/795,413, filed on Apr. 26, 2006, provisional application No. 60/854,341, filed on Oct. 24, 2006, provisional application No. 60/615,267, filed on Oct. 1, 2004.

(56) References Cited

U.S. PATENT DOCUMENTS

| | | | |
|---|---|---|---|
| 4,512,476 | A | 4/1985 | Herrington, Jr. |
| 4,535,890 | A | 8/1985 | Artusi |
| 4,546,901 | A | 10/1985 | Buttarazzi |
| 4,655,026 | A | 4/1987 | Wigoda |
| 4,693,371 | A | 9/1987 | Malpass |
| 4,749,085 | A | 6/1988 | Denney |
| 4,799,590 | A | 1/1989 | Furman |
| 4,805,800 | A | 2/1989 | Nocek et al. |
| 4,850,489 | A | 7/1989 | Weithmann et al. |
| 4,867,315 | A | 9/1989 | Baldwin |
| 4,872,559 | A | 10/1989 | Schoon |
| 4,887,790 | A | 12/1989 | Wilkinson et al. |
| 4,918,604 | A | 4/1990 | Baum |
| 4,953,745 | A | 9/1990 | Rowlett, Jr. |
| 4,972,657 | A | 11/1990 | McKee |
| 5,014,851 | A | 5/1991 | Wick |
| 5,186,345 | A | 2/1993 | Ching An |
| 5,195,123 | A | 3/1993 | Clement |
| 5,199,636 | A | 4/1993 | Young |
| 5,310,057 | A | 5/1994 | Caldwell et al. |
| 5,366,087 | A | 11/1994 | Bane |
| 5,390,796 | A | 2/1995 | Kerfoot, Jr. |
| 5,457,895 | A | 10/1995 | Thompson et al. |
| 5,505,371 | A * | 4/1996 | O'Neill ............ 229/120.26 |
| 5,558,229 | A | 9/1996 | Halbich |
| 5,577,612 | A | 11/1996 | Chesson et al. |
| 5,597,995 | A | 1/1997 | Williams et al. |
| 5,642,906 | A | 7/1997 | Foote et al. |
| 5,671,592 | A | 9/1997 | Yuyama et al. |
| 5,737,539 | A | 4/1998 | Edelson et al. |
| 5,788,079 | A * | 8/1998 | Bouthiette ............ 206/534 |
| D400,412 | S * | 11/1998 | Gold ................. D8/20 |
| 5,878,887 | A | 3/1999 | Parker et al. |
| 5,883,370 | A | 3/1999 | Walker et al. |
| 5,899,333 | A | 5/1999 | Williams et al. |
| 5,921,398 | A * | 7/1999 | Carroll ............ 206/736 |
| 5,963,453 | A | 10/1999 | East |
| 5,995,938 | A | 11/1999 | Whaley |
| 6,012,582 | A | 1/2000 | Haygeman et al. |
| 6,115,996 | A | 9/2000 | Yuyama et al. |
| 6,129,211 | A * | 10/2000 | Prakken et al. ........... 206/750 |
| 6,155,423 | A * | 12/2000 | Katzner et al. ........... 206/531 |
| 6,155,485 | A | 12/2000 | Coughlin et al. |
| 6,202,923 | B1 | 3/2001 | Boyer et al. |
| 6,273,260 | B1 | 8/2001 | ColDepietro et al. |
| 6,293,403 | B1 | 9/2001 | Holmberg |
| 6,308,494 | B1 | 10/2001 | Yuyama et al. |
| 6,318,630 | B1 | 11/2001 | Coughlin et al. |
| 6,324,253 | B1 | 11/2001 | Yuyama et al. |
| 6,343,695 | B1 | 2/2002 | Petrick et al. |
| D455,057 | S * | 4/2002 | Medhurst ............ D8/20 |
| 6,371,297 | B1 | 4/2002 | Cha |
| 6,401,919 | B1 | 6/2002 | Griffis et al. |
| 6,449,927 | B2 | 9/2002 | Hebron et al. |
| 6,460,693 | B1 | 10/2002 | Harrold |
| 6,505,461 | B1 | 1/2003 | Yasunaga |
| 6,523,694 | B2 | 2/2003 | Lux, Jr. et al. |
| 6,535,637 | B1 | 3/2003 | Wootton et al. |
| 6,581,798 | B2 | 6/2003 | Liff et al. |
| 6,662,081 | B1 | 12/2003 | Jacober et al. |
| 6,681,935 | B1 * | 1/2004 | Lewis ............ 206/534 |
| 6,711,460 | B1 | 3/2004 | Reese |
| 6,735,497 | B2 | 5/2004 | Wallace et al. |
| 6,738,723 | B2 | 5/2004 | Hamilton |
| 6,757,898 | B1 | 6/2004 | Ilsen et al. |
| 6,771,369 | B2 | 8/2004 | Rzasa |
| 6,892,512 | B2 | 5/2005 | Rice et al. |
| 6,925,774 | B2 | 8/2005 | Peterson |
| 6,981,592 | B2 | 1/2006 | Siegel |
| 7,006,893 | B2 | 2/2006 | Hart et al. |
| 7,010,899 | B2 | 3/2006 | McErlean et al. |
| 7,028,723 | B1 | 4/2006 | Alouani et al. |
| 7,055,294 | B1 | 6/2006 | Lewis |
| 7,111,780 | B2 | 9/2006 | Broussard et al. |
| 7,185,476 | B1 | 3/2007 | Siegel et al. |
| 7,225,597 | B1 | 6/2007 | Knoth |
| 7,398,279 | B2 | 7/2008 | Muno et al. |
| 7,426,814 | B2 | 9/2008 | Knoth |
| 7,509,787 | B2 * | 3/2009 | Ballestrazzi et al. ........... 53/411 |
| 7,668,730 | B2 | 2/2010 | Reardan et al. |
| 2002/0029223 | A1 | 3/2002 | Rice et al. |
| 2002/0042725 | A1 | 4/2002 | Mayaud |
| 2002/0066691 | A1 | 6/2002 | Varon |
| 2002/0117405 | A1 | 8/2002 | Wang et al. |
| 2003/0012701 | A1 * | 1/2003 | Sangha et al. ............ 422/102 |
| 2003/0018495 | A1 | 1/2003 | Sussman |
| 2003/0136698 | A1 | 7/2003 | Klatt |
| 2003/0193185 | A1 | 10/2003 | Valley et al. |
| 2003/0200726 | A1 | 10/2003 | Rast |
| 2004/0011961 | A1 | 1/2004 | Platt et al. |
| 2004/0069675 | A1 | 4/2004 | Stevens |
| 2004/0088187 | A1 | 5/2004 | Chudy et al. |
| 2004/0122713 | A1 | 6/2004 | Hill, Sr. et al. |
| 2004/0158507 | A1 | 8/2004 | Meek, Jr. et al. |
| 2004/0162634 | A1 | 8/2004 | Rice et al. |
| 2004/0172295 | A1 | 9/2004 | Dahlin et al. |
| 2004/0188998 | A1 | 9/2004 | Henthorn |
| 2004/0217038 | A1 | 11/2004 | Gibson |
| 2004/0225528 | A1 | 11/2004 | Brock |
| 2004/0243445 | A1 | 12/2004 | Keene |
| 2004/0256277 | A1 | 12/2004 | Gedanke |
| 2005/0021367 | A1 | 1/2005 | Saeger et al. |
| 2005/0049746 | A1 | 3/2005 | Rosenblum |
| 2005/0049747 | A1 | 3/2005 | Willoughby et al. |
| 2005/0060197 | A1 | 3/2005 | Mayaud |
| 2005/0061825 | A1 | 3/2005 | Willoughby et al. |
| 2005/0144038 | A1 | 6/2005 | Tamblyn et al. |
| 2005/0171813 | A1 | 8/2005 | Jordan |
| 2005/0209879 | A1 | 9/2005 | Chalmers |
| 2005/0218152 | A1 | 10/2005 | Simon |
| 2006/0122729 | A1 | 6/2006 | Murphy et al. |
| 2007/0173971 | A1 | 7/2007 | Richardson et al. |
| 2008/0190076 | A1 | 8/2008 | Klingel et al. |

FOREIGN PATENT DOCUMENTS

| WO | WO 2004/082561 A1 | 9/2004 |
|---|---|---|
| WO | WO 2005/102841 | 11/2005 |

* cited by examiner

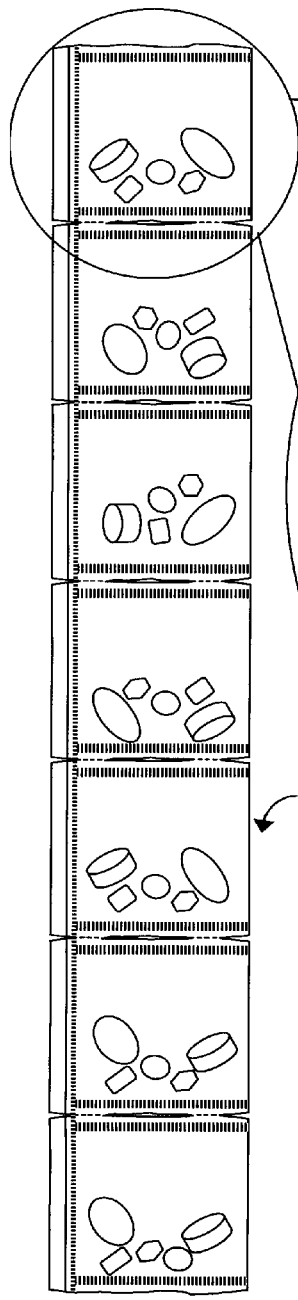
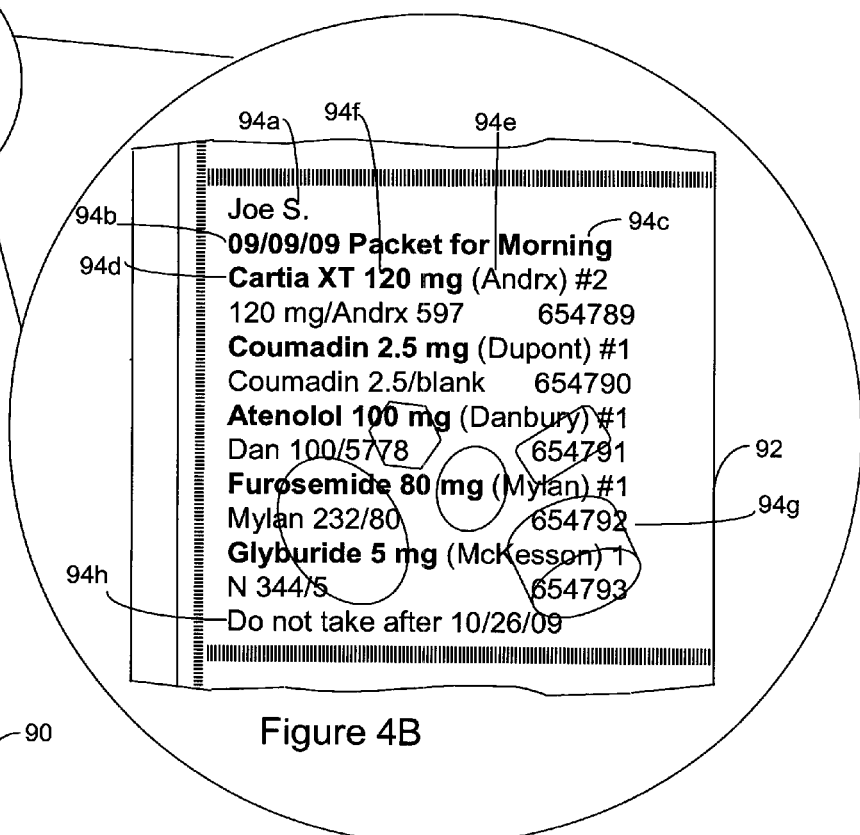
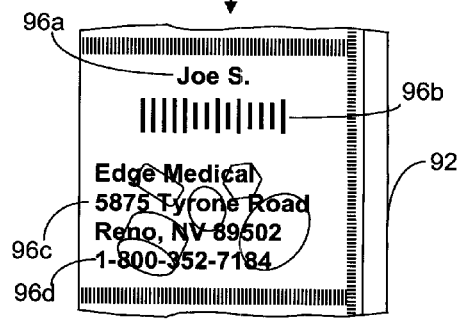
Figure 4A
Figure 4B
Figure 4C

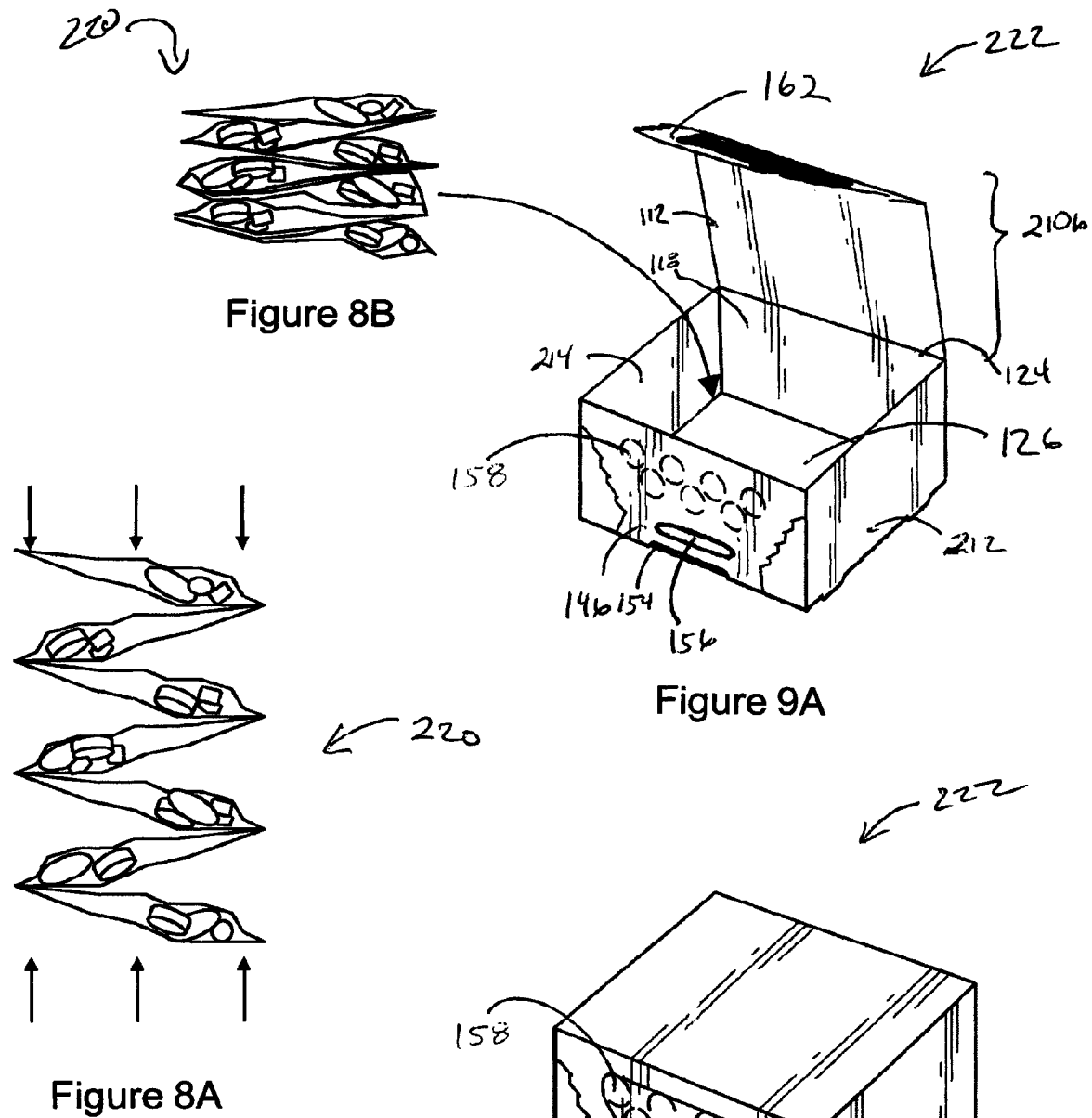
Figure 8B
Figure 9A
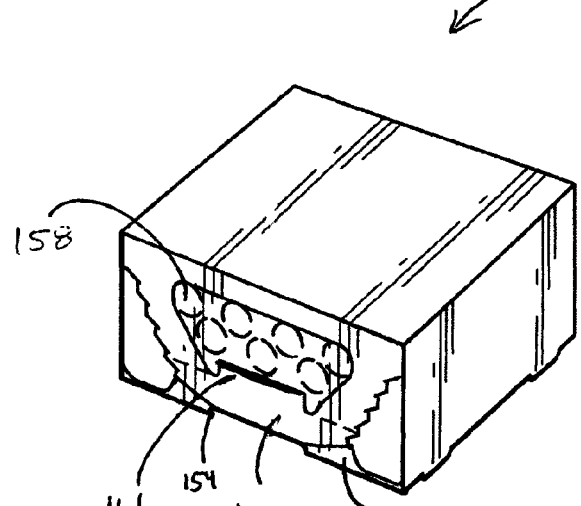
Figure 8A
Figure 9B

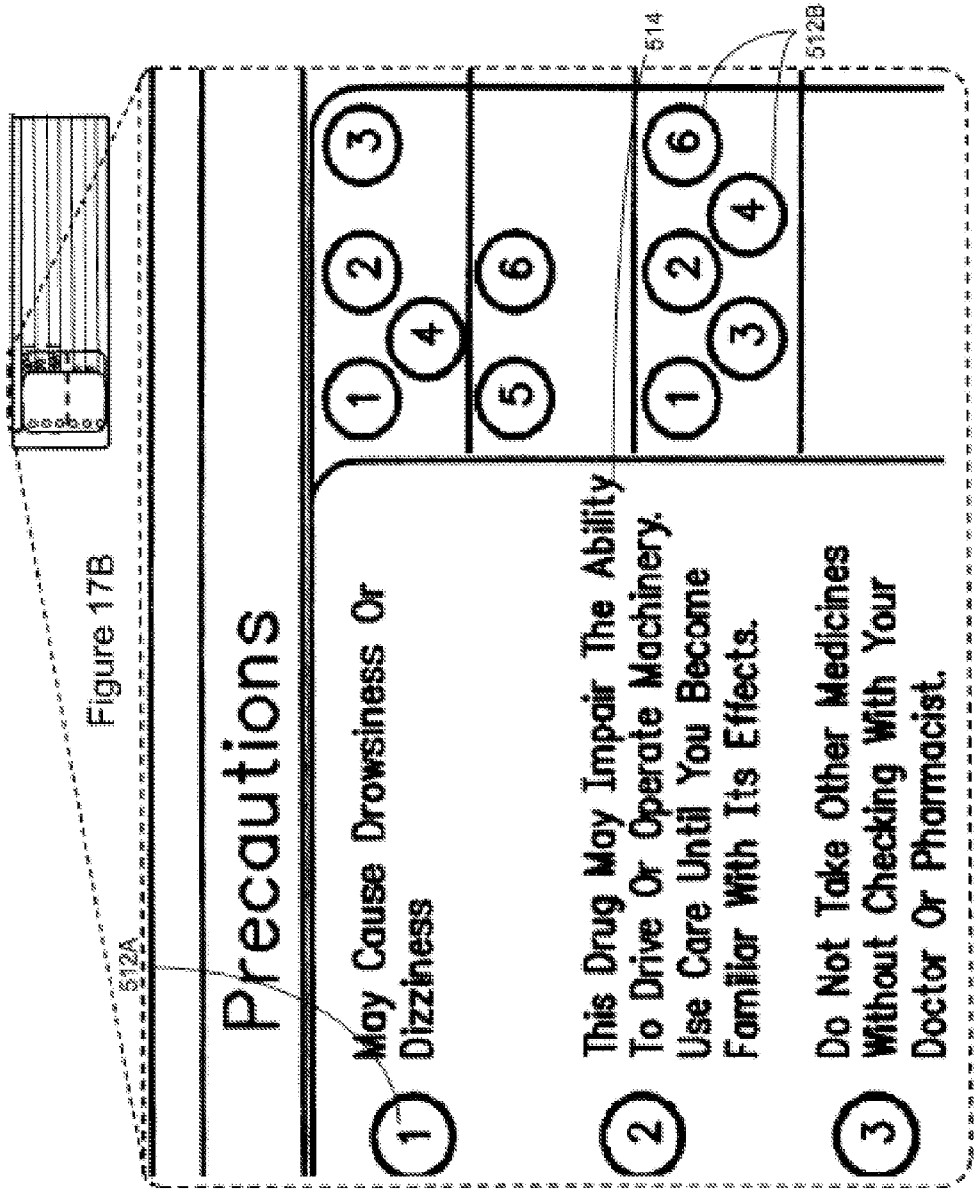

MANUFACTURING SEPARABLE POUCHES WITH A CENTER CUT BLADE

CROSS REFERENCING

The present patent application claims priority from provisional patent applications 61/045,160, 61/045,166, and 61/045,171, all filed Apr. 15, 2008. The present application is a continuation-in-part of nonprovisional application Ser. No. 11/923,321, filed Oct. 24, 2007, which is a continuation-in-part of nonprovisional patent application Ser. Nos. 11/796,123, 11/796,124, and 11/796,125 filed Apr. 25, 2007, which all claim benefit of provisional applications 60/795,370, 60/795,446, and 60/795,413, filed Apr. 26, 2006, and provisional application 60/854,341, filed Oct. 24, 2006. This application is a continuation-in-part of nonprovisional application Ser. No. 11/241,783, filed Sep. 30, 2005, which is related to provisional application 60/615,267, filed Oct. 1, 2004. All applications listed in this paragraph are hereby incorporated by reference.

FIELD OF THE INVENTION

The present invention relates to a system for manufacturing a plurality of separable pouches with a center cut blade. More particularly, the invention relates to forming sealed pouches and separating each sealed pouch using the center cut blade.

BACKGROUND

Approximately fifty to seventy percent of all prescription medications in the U.S. are taken incorrectly. The effects of this prescription misuse account for 3.1 million nursing home admissions each year. More patients in the U.S. die each year from medication mismanagement than from AIDS and automobile accidents combined, and it is estimated that 125,000 deaths per year are caused by improper use of prescription drugs.

One of the major problems in taking prescribed daily medications emanates from patients having to take more than one medication in the form of pills or tablets. A principal concern is determining whether all medications are in compliance with the prescribed daily regimen. Many times this concern is compounded by the requirement that portions of the different medications must be taken at different times during the day.

The fear of taking improper dosages of prescribed medication can be particularly acute in the elderly, many of whom have some degree of mental dementia and can easily be confused as to whether they have taken all of their medications at the correct time. Some patients have difficulty sorting out the medications prior to taking them and taking the medication in a timely manner. Providing medications to disabled or incapacitated individuals can also be complicated because one caregiver may oversee the medication of many patients.

One solution to the problem of taking multiple medications is to pre-package the multiple medications so that users can take the pre-packaged medications at a predetermined time. Generally, these methods of pre-packaging medications are targeted to patients that may lack maturity or mental capacity to take the correct medications at the correct time. For example, young children in a school or campground, and elderly individuals in elder care centers, or nursing homes are target groups for the pre-packaging of medications. Some of the pre-packaged medications are placed in a small plastic bag, which may be easily misplaced. Other pre-packaged medications are placed in sealed cups that are difficult to open.

Although multiple prescription filling systems are available, e.g. the McKesson PACMED system, these systems have limited capabilities. For example, these filling systems fail to assemble a multiple prescription order that can be easily transported and administered. Additionally, these filling systems fail to effectively organize the multiple prescription medications. Furthermore, the filling systems fail to organize the multiple prescription containers. Further still, the filling systems fail to provide a compliance packaging solution.

SUMMARY

A system for manufacturing a plurality of separable pouches comprising a means for forming sealed pouches, a center cut blade and a means for segregating each sealed pouch with the center cut blade is described. The means for forming the sealed pouches includes placing a plurality of different tablets corresponding to different medications into each sealed pouch. The center cut blade includes a side cut on each end of the blade, a center cut in the middle of the blade, and at least one perforation cut between each side cut and the center cut. The means for separating each sealed pouch with the center cut blade provides each sealed pouch with a sealed top end, a sealed bottom end, and two sides, in which at least one side is also sealed. Each sealed pouch is joined to an adjacent pouch by a plurality of tearable ribbons. Additionally, each sealed pouch includes a side cut on each side of the top end and bottom end of the sealed pouch, a center cut on the top end and bottom end of the sealed pouch, and at least one perforation between each side cut and the center cut.

Additionally, a system for manufacturing a plurality of separable pouches comprising a heated roller and a center cut blade is also described. The heated roller is configured to seal each pouch. Each pouch includes the plurality of different tablets corresponding to different medications and each sealed pouch includes a sealed top end, a sealed bottom end, and two sides, in which at least one side is also sealed. The center cut blade is configured to be affixed to the heated roller that segregates each sealed pouch. The center cut blade comprises a side cut on each end of the blade, a center cut in the middle of the blade, and a plurality of perforation cuts between each side cut and the center cut.

Furthermore, a system for manufacturing a plurality of separable pouches comprising a heated roller, a center cut blade with a center cut that is longer than each of the side cuts, and at least one perforation with at least two tearable ribbons between each side cut and the center cut is described.

DRAWINGS

The present invention will be more fully understood by reference to the following drawings which are for illustrative, not limiting, purposes.

FIG. 4A shows a group of seven separable pouches, wherein each pouch comprises a plurality of different tablets.

FIG. 4B shows an exploded view of the illustrative front side of one of the sealed center cut pouches that is included in the strip of pouches.

FIG. 4C shows an exploded view of the illustrative back side of the pouch in FIG. 4B.

FIG. 8A shows a strip of seven separable pouches.

FIG. 8B shows a folded strip of seven separable pouches.

FIG. 9A shows another illustrative folded box with a label area defined by the top wall.

FIG. 9B shows the illustrative folded box of FIG. 9A in a closed position.

FIGS. 17A-17E show a flat plan view of an illustrative label.

DESCRIPTION

Figure 1A:
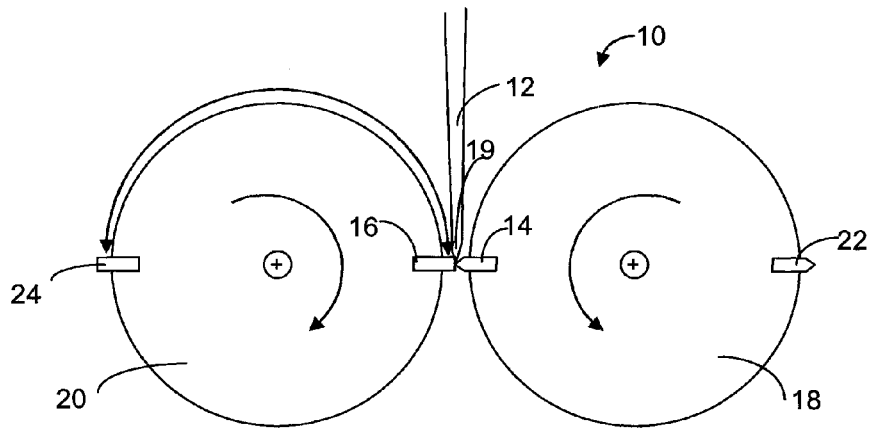
FIG. 1A shows a pair of prior art heated rollers that cut and seal the illustrative pouches.

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the apparatus and systems described herein may vary as to configuration and as to details. Additionally, the methods may vary as to details, order of the actions, or other variations without departing from the illustrative method disclosed herein.

The systems, apparatus and methods described herein provide the correct medications and dosages at the right time. The packaging is designed with clear images and names to simplify the process of determining the appropriate medications to take at the appropriate time. Additionally, the patient medication management system and method described herein eliminates that worry of taking the wrong medication at the wrong time, and eliminates the need to the manually open and organize prescriptions each week. Furthermore, the system and method described herein gathers all the patient's medicines together in one package, and clearly shows the proper dosage time.

The terms "tablets", "medications" and "medicaments" as used herein refer to medications, pharmaceuticals, nutriceuticals, vitamins, capsules, gel caps, pills and other such medicinal or nutritional preparations for oral use as would be appreciated by those of ordinary skill in the art of pharmacy.

The systems, apparatus and methods described herein provide assurances of the proper dosages at the proper period. Additionally, caregivers and patients get the assurance that the patient is getting the right medications and staying compliant with those medications. Furthermore, a time saving solution for dispensing tablets, medications and vitamins is described.

One of the patient medication management systems provides a compliant packaging solution. For purposes of this patent, the term "compliant packaging" refers to packaging tablets so that they are administered in a manner that complies with one or more prescriptions. Additionally, compliant packaging may also refer to providing reminders for taking medications and/or recording that the medications have been consumed.

By way of example and not of limitation, compliance packaging may include three elements: firstly, an action is initiated by a patient and/or caregiver with the compliance package; secondly, the compliance package dispenses at least one tablet as a result of the action taken by the patient and/or caregiver; and thirdly, the compliance package records the dispensing of the tablet. An illustrative example of a "compliance package" is the well-known birth control "dial pack" package, in which there are twenty-eight tablets in a blister package that are in a circular configuration (not shown). To consume the tablet, the patient pushes on the transparent plastic material and the tablet pierces a foil backing. After the tablet is dispensed from the dial package, a record is left on the dial pack package, i.e. a pressed plastic housing and pierced foil backing.

Compliant packaging may also include a compliant package having a plurality of different tablets corresponding to one or more prescriptions from one or more medical doctors. The compliant package is consumed at a predetermined interval consistent with the prescription. Some compliant packaging solutions may not record that each of the tablets is consumed.

One of the illustrative patient medication systems described herein satisfies the requirements for a compliance package because an action is required by the patient or caregiver that requires identifying the appropriate dosage period, e.g. morning, and selecting the appropriate pouch. The patient or caregiver records the consumption of the medication by removing the packet containing the appropriate medication from the container and consuming the medication. Since the packet is imprinted with a dosage time period and date for consumption, a patient or caregiver can tell at a glance whether the medication for the current date and dosage period has already been consumed or whether it remains to be taken.

Referring to FIG. 1A there is shown a pair of prior art heated rollers that cut and seal the illustrative pouches that hold the tablets. The illustrative pouch 12 is cut and perforated by a cutting blade 14 and cutting block 16 that is fixedly coupled to heated roller 18 and heated roller 20, respectively. The heated rollers also seal the end 19 of the pouch 12. The heated roller 18 includes a second cutting blade 22 that cuts, perforates and seals the opposite end of the pouch 12 (not shown). The second heated roller 20 includes a second cutting block 24 that is located at an equidistant point from the cutting block 16. The illustrative rollers 18 and 20 also seal the edges of the pouch. The illustrative combination of the heated rollers 18 and 20 and cutting blade 14 and cutting block 16 may be found in a PACMED™ system sold by the McKesson Corporation from Pennsylvania.

Figure 1B:
FIG. 1B shows a side view of a prior art cutting block and a prior art cutting blade shown in FIG. 1A.

Referring now to FIG. 1B there is shown a side view of the cutting block 16 and cutting blade 14 that are both fixedly coupled to the heated rollers of FIG. 1A. The cutting blade 14 has a flat face 26 and a pointed edge 28.

Figure 1C:
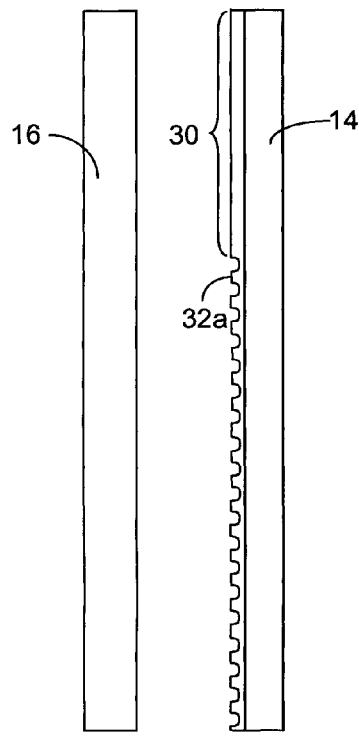
FIG. 1C shows a side view of the prior art cutting block and the prior art cutting blade that are both fixedly coupled to the heated rollers of FIG. 1A.

In FIG. 1C there is shown a side view of the cutting block 16 and cutting blade 14 that are both fixedly coupled to the heated rollers of FIG. 1A. Generally, block 16 is a rectangular block shaped metal alloy. The cutting blade 14 may be composed of the same or similar metal alloy and includes a single side cut 30 of a predetermined length and a plurality of smaller cuts such as 32a that score or cut the pouch 12 and provide perforations between the heat-sealed edges of each pouch.

Figure 1D:
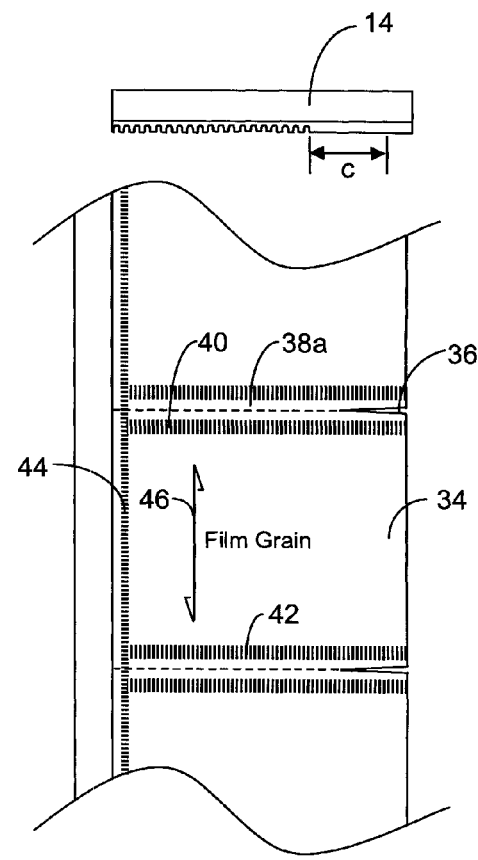
FIG. 1D shows a sealed prior art pouch with a single side cut adjacent to the prior art cutting blade.

In FIG. 1D there is shown an illustrative sealed prior art pouch with a single side cut adjacent to the prior art cutting blade 14. The illustrative pouch 34 includes a single cut 36, a plurality of perforations such as perforation 38a, a sealed top edge 40, a sealed bottom edge 42, and a sealed side edge 44. In the illustrative embodiment, the pouch 34 is formed by taking a plastic sheet composed of a polymeric compound and folding the plastic sheet over and sealing the side edge 44 and the sealed bottom edge 42 and sealed top edge 40. The length of the single cut 36 is determined by the single side cut 30.

The plastic pouch materials may be obtained with the PACMED™ system and the consumables are sold by the McKesson Corporation; however, the chemical and material properties of the plastic materials have not been publicly disclosed. Regardless, the inventors have discovered that there are various limitations corresponding to the plastic pouch materials. In the embodiments disclosed herein, the plastic "pouch" material is sold as a consumable for the PACMED system. Alternatively, an AUTOMED packaging system may also be used.

In general, the plastic pouches generated by the PACMED machines do not tear easily. The single cut 36 and multiple perforations 38a result in the tearing of the existing pouch and adjacent pouches. Although, each the perforations 38a are intended to facilitate horizontal tearing, the perforations 38a regularly result in a tear taking a circuitous route that tears the existing pouch or adjacent pouch. Thus, when a user tears the prior art pouches, there is a likelihood that the resulting tear is not horizontal and tears the sealed pouch holding the tablets or the adjacent sealed pouch.

Additionally, it appears that there is a film grain 46 corresponding to the plastic materials that result in vertical tearing of the pouches, so that upon attempting to separate a first pouch from a second pouch, a tear occurs with significant frequency on either pouch itself or the adjacent pouch that would result in tablets being spilt on a table or floor. The complexity of this problem is magnified by the plastic pouch materials being sold exclusively by McKesson Corporation and there being no alternative pouch materials that operate with the PACMED system.

Figure 2A:
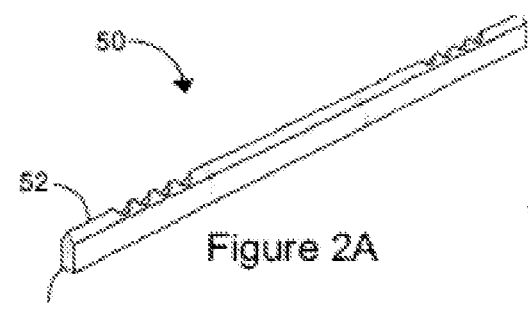
FIG. 2A shows an isometric view of a center cut cutting blade that is used to generate a separable pouch with a center cut.

Referring to FIG. 2A there is shown an isometric view of a center cut blade that is used to generate a separable pouch with a center cut. The center cut blade 50 generates separable pouches that enable a patient or caregiver to access the medications in the pouches without tearing adjacent pouches. The center cut blade 50 is fixedly coupled to heated rollers 18 shown in FIG. 1A. The heated rollers 18 and 20 are configured to seal each pouch and to also cut the plastic pouch material. The illustrative cutting blade 50 has a top edge 52 and a bottom face 54.

Figure 2B:
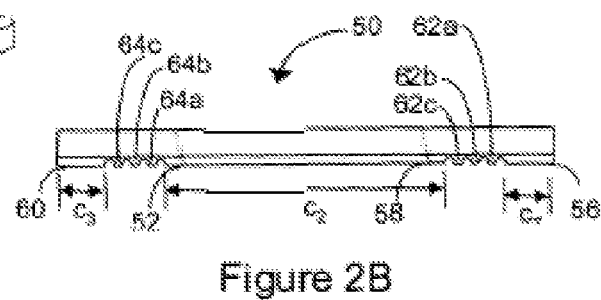
FIG. 2B shows an inverted side view of the center cut blade shown in FIG. 2A.

Referring to FIG. 2B there is shown an inverted side view of the center cut blade shown in FIG. 2A. The top edge 52 of the center cut blade 50 comprises a first side cut 56 having a $c_1$ length, a center cut 58 having a $c_2$ length, and a second side cut 60 having a $c_3$ length. The first side cut 56 and second side cut 60 are on each end of the blade 50. The center cut 58 is in the middle of the blade 50 and is separated from the first side cut 56 by perforation cuts 62a, 62b and 62c. On the opposite end, the second side cut 60 is separated from the center cut 58 by the perforation cuts 64a, 64b, and 64c. Each perforation is a relatively small cut compared to either the side cuts or the center cut. The center cut length is greater than the length of each side cut.

For example, in a broad illustrative embodiment the dimensions of the first side cut 56 $c_1$ length can range from 1.0 mm to 20.0 mm. The dimensions of the second side cut 60 $c_3$ length can range from 1.0 mm to 20.0 mm. The center cut 58 $c_2$ length can range from 1.0 mm to 50.0 mm. The number and size of perforation cuts can also vary. For example, there may 1 to 10 perforation cuts in the broad illustrative embodiment, and the width of the perforation cuts can vary from 0.1 mm to 2.0 mm.

In a more limiting embodiment, the dimensions of the first side cut 56 $c_1$ length can range from 5.0 mm to 15.0 mm. The dimensions of the second side cut 60 $c_3$ length can range from 5.0 mm to 15.0 mm. The center cut 58 clength can range from 20.0 mm to 40.0 mm. The number and size of perforation cuts can also vary. For example, there may 2 to 5 perforation cuts in the less broad illustrative embodiment, and the width of the perforation cuts can vary from 0.5 mm to 1.5 mm.

In the preferred embodiment shown in FIG. 2B, the length of first side cut 56 is approximately 10 mm and for second side cut 60 is approximately 10 mm. The center cut 58 is approximately 35, mm. In the preferred embodiment, there are three perforation cuts resulting in four tearable ribbons on each side of the center cut 58. The width of the perforation cuts is approximately 1.0 mm, and each of the tearable ribbons is approximately 1.0 mm.

Figure 2C:
FIG. 2C shows an illustrative elevational side view of a cutting block and the center cut cutting blade.

Referring to FIG. 2C, there is shown an illustrative elevational side view of a cutting block 66 and the center cut blade 50. This profile of the center cut blade 50 and the cutting block 66 shows that the center cut blade 50 has the same profile as the prior art cutting blade 14 shown in FIG. 1B. In operation, the center cut blade 50 and cutting block 66 are fixedly coupled to rotating heated rollers that effectively cut and seal the pouch. The illustrative heated roller described herein provides a dual role, namely, the heated roller provides a means for forming sealed pouches because the heated roller is used to seal the plastic pouch material. Additionally, once the center cut blade is placed in the heated roller, the combination provides a means for separating each sealed pouch without tearing the existing sealed pouch or tearing the adjacent sealed pouch.

Figure 2D:
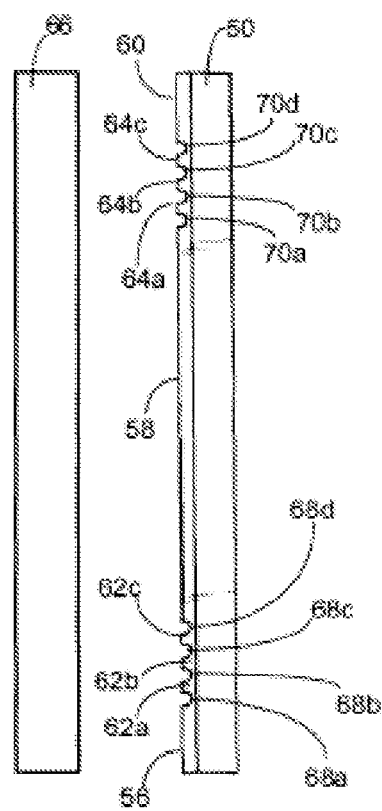
FIG. 2D shows an exploded view of the cutting block and the center cut cutting blade.

Referring to FIG. 2D, there is shown an exploded view of the cutting block and the center cut cutting blade. A more detailed view of the center cut blade 50 depicts the first side cut 56 adjacent to a first u-shaped well 68a that is adjacent the perforation cut 62a. Note, the terms "u-shaped well" and "well" are used interchangeably. A second u-shaped well 68b follows and is adjacent to another perforation cut 62b that is also adjacent well 68c. Well 68c is also adjacent to perforation cut 62c which is, in turn, adjacent to well 68d. Adjacent to well 68d is the center cut 58. The center cut 58 is separated from the second side cut 60 by the alternating combinations of the perforation cuts 64a-64c and wells 70a-70d. The first side cut 56 and second side cut 60 are on each end of the blade 50. The illustrative four wells 68a-68d and 70a-70d generate four ribbons on the plastic pouches that are between each side cut and the center cut that are described in further detail below.

Referring back to FIG. 2A the u-shaped wells 68a-68d and 70a-70d are not sharpened and do not cut the plastic pouch materials. As a result, "ribbons" are produced that connect or couple the pouches to one another.

Figure 2E:
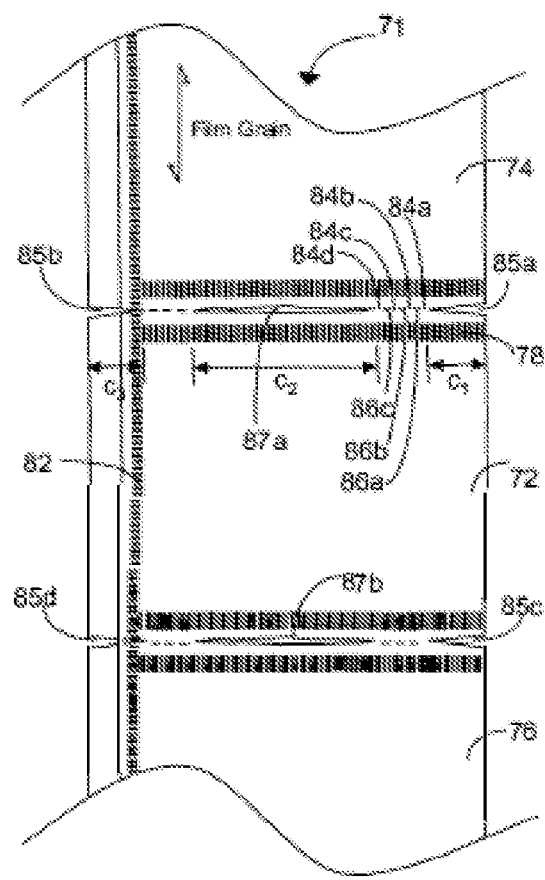
FIG. 2E shows an illustrative strip that includes a sealed center cut pouch.

The separable sealed pouches may then be grouped into of collections of seven pouches (for the seven-day box), twenty-eight pouches, thirty pouches, or any other such combination. A plurality of sealed pouches that is grouped is also referred to as a "strip," and the terms "strip" and "group of pouches" is used interchangeably in this patent. A typical strip includes seven pouches, twenty-eight pouches, or thirty pouches. In one embodiment described in further detail below, a reminder strip consists of seven pouches, followed by an empty pouch with printing on the pouch to remind the patient and/or caregiver to re-order, and two remaining pouches. In another embodiment, there are twenty-eight pouches followed by an empty pouch with printing on the pouch to remind the patient and/or caregiver to re-order, and two remaining pouches Referring now to FIG. 2E there is shown an illustrative strip 71 that includes a sealed center cut pouch 72. The illustrative pouch 72 is adjacent to pouch 74 and pouch 76. By way of example and not of limitation, the illustrative pouch 72 comprises a sealed top end 78, a sealed bottom end 80, and two sides, in which at least one side is also sealed, e.g. side seal 82, and the other side is folded over. Each illustrative pouch includes different tablets corresponding to different medications, vitamins, or other such medicinal or nutritional preparation for oral use.

Additionally, the illustrative pouch is joined to an adjacent pouch by a plurality of tearable ribbons 84a-84d adjacent to the first side cut 85a adjacent the top end 78. A similar grouping of tearable ribbons is also adjacent the second side cut 85b adjacent to the top end. Each sealed pouch comprises side cuts 85a and 85b on each side of the top end 78 and side cuts 85c and 85d on each side of bottom end 80.

The illustrative embodiment shows a pouch with at least three perforations between each side cut and the center cut. The first ribbon 84a is disposed between the first side cut 85 and the first perforation 86a. The second ribbon 84b and third ribbon 84c are each disposed between perforations 86a, 86b and perforations 86b, 86c, respectively. The fourth ribbon 84d is disposed between the third perforation 86c and the center cut 87a. A similar configuration of perforations and ribbons surround the center cut 87b that is adjacent the bottom end 80. In the illustrative example, the ribbons have a width corresponding to the width of the u-shaped well.

The resulting pouch can be opened on either side and the center cut prevents tearing the existing pouch or the adjacent pouch. In general, the pouch described minimizes the number of tearable ribbons thereby minimizing the likelihood of tearing the existing pouch or the adjacent pouch. Additionally, having the tearable ribbons at the edges of the pouch also minimizes the likelihood of tearing into the existing or adjacent pouches.

Figure 3A:
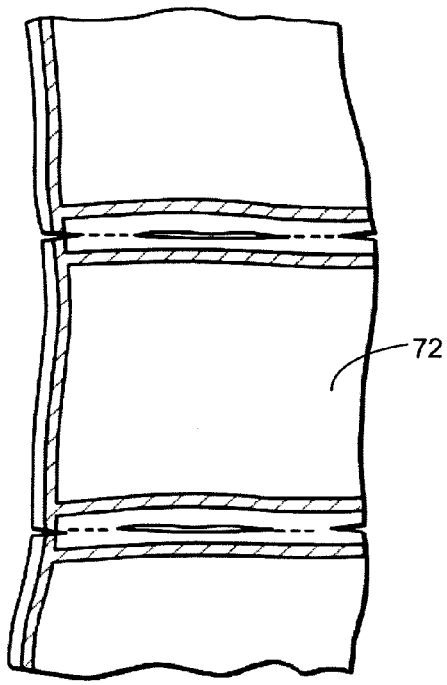
FIG. 3A shows an illustrative sealed center cut pouch with three perforations and four tearable ribbons on each side of the center cut.
Figure 3B:
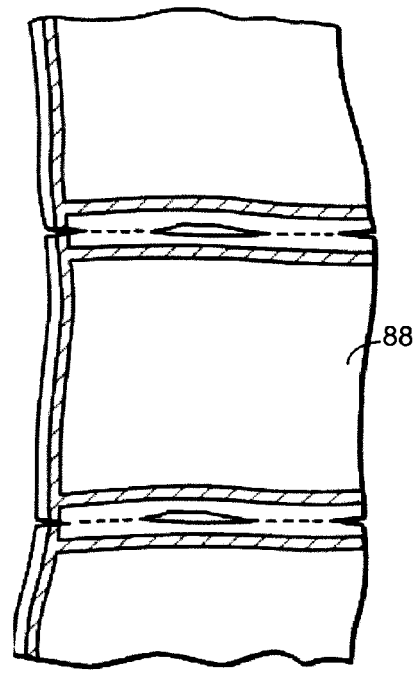
FIG. 3B shows an illustrative sealed center cut pouch with four perforations on each side of the center cut.
Figure 3C:
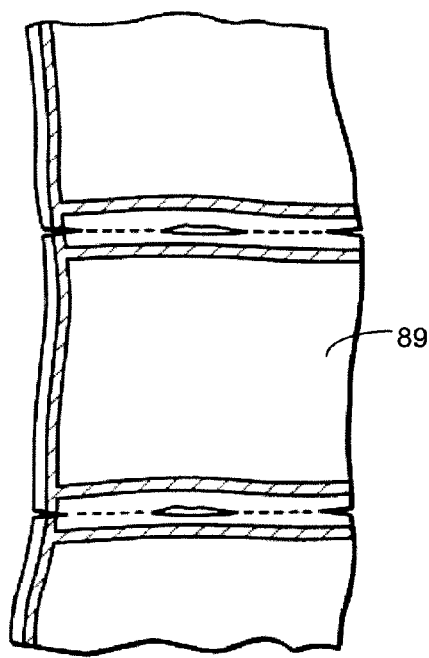
FIG. 3C shows an illustrative sealed center cut pouch with five perforations on each side of the center cut.

It shall be appreciated by those of ordinary skill in the art having the benefit of this disclosure that the resulting pouch will vary depending on the type of pouch material being used, the thickness or weight of the pouch material, the seal, the length of the cuts, the number of cuts, the length of the perforations, number of perforations, the width of the tearable ribbons, and the frequency of tearable ribbons. For example, in FIG. 3A there is shows the illustrative sealed center cut pouch 72 described above with three perforations and four tearable ribbons on each side of the center cut. In FIG. 3B there is shown an illustrative sealed center cut pouch 88 with four perforations on each side of the center cut. FIG. 3C depicts another illustrative sealed center cut pouch 89 with five perforations on each side of the center cut.

Referring to FIG. 4A there is shown a group of seven separable pouches, wherein each pouch comprises a plurality of different tablets. The separable sealed pouches have been grouped into a collection of seven pouches 90 that correspond to a seven day supply of medications. A plurality of sealed pouches that is grouped is also referred to as a "strip," and the terms "strip," "group of pouches," and "strip of pouches" is used herein interchangeably.

Referring to FIG. 4B there is shown an exploded view of the illustrative front side of one of the sealed center cut pouches 92 that is included in the strip of pouches 90. The exploded view shows that a variety of data fields that are printed on the front of each pouch. In general, the data fields provide information corresponding to each tablet within the pouch. The data fields includes: the name of the patient 94a; the date the tablets should be consumed 94b; the time of day the tablets should be taken 94c; the name of the prescribed medication 94d; the name of the corresponding generic 94e; the dosage 94f; and the prescription number 94g. Additionally, an expiration date 94h is included that identifies the medications should not be taken after the expiration date.

Referring to FIG. 4C there is shown an exploded view of the illustrative back side of the pouch 92 in FIG. 4B. The data fields include: the name of patient 96a; a bar code 96b; the address of the facility that filled the pouches with tablets 96c; and the telephone number 96d for additional information. The illustrative bar code associates the tablets in the foldable box with a particular patient.

The illustrative seven-day strip 90 is then placed in an illustrative seven-day container. An illustrative seven-day container is presented in FIG. 5A through FIG. 12. These illustrative containers are then placed in a secondary container such as described in FIG. 13 and FIG. 14.

Figure 5A:
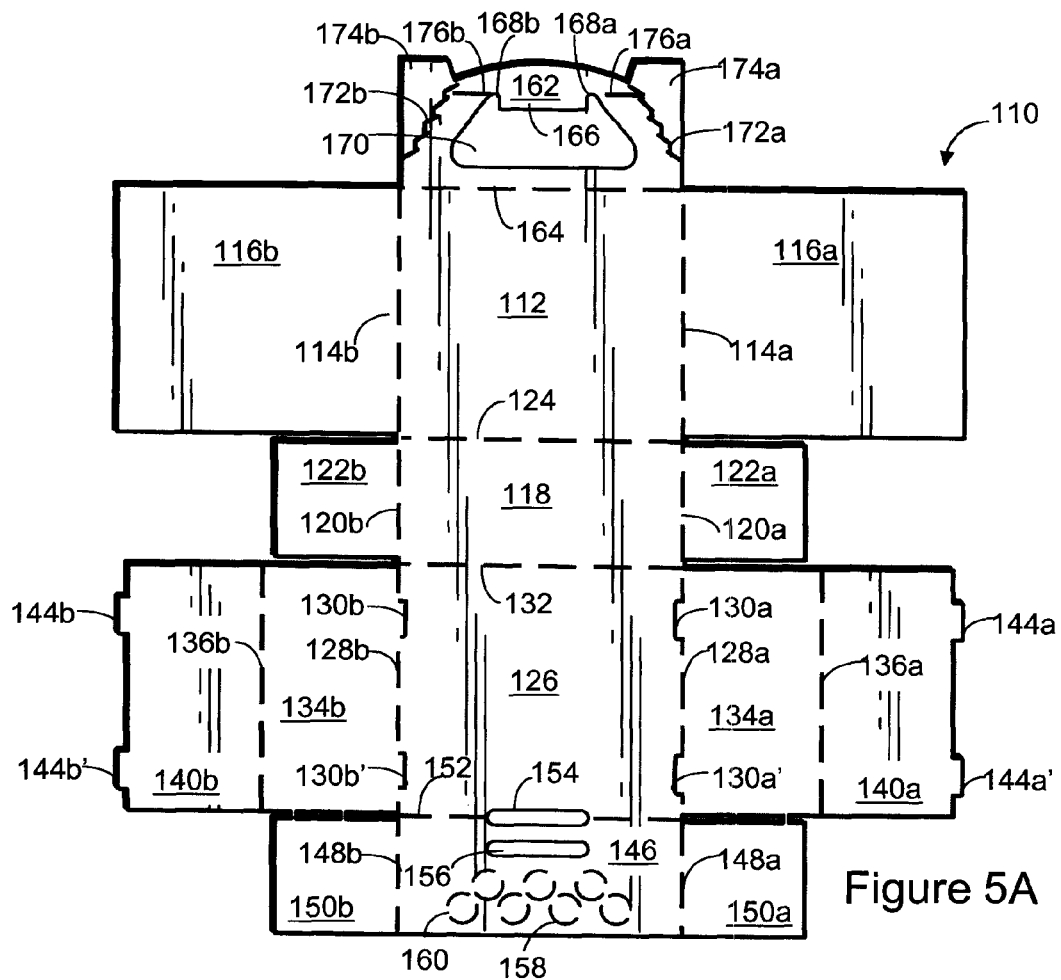
FIG. 5A shows a plan view of blank used to form a foldable box configured to receive a plurality of center cut pouches.

Referring to FIG. 5A there is shown a plan view of a blank 110 used to form an assembled box 180 (shown in FIG. 5B) that holds a plurality of pouches, wherein each pouch includes a plurality of different tablets. The foldable box is formed from a single piece of cardboard configured to receive a plurality of pouches as described herein. The blank 110 is formed from a corresponding stamping die that presses against a large piece of cardboard and cuts out the perimeter of the blank and forms the scores, holes and other cuts on the blank, in a manner well known in the art of box making. The scores are depressions in the blank 110 and are formed by projections on the dies that press into the corrugated cardboard blank 110 sufficiently to form a score or fold line, but not cut all the way through the blank 110. The cuts or perforations in blank 110 are formed by sharpened depressions on the die that cut all the way through the blank.

By way of example and not of limitation, the illustrative cardboard or blank 110 includes an outer smooth layer of paper and a thick interior layer. The outer smooth layer may receive printed text or images using an illustrative laser printer, ink jet printer, or other such printing means.

Figure 5B:
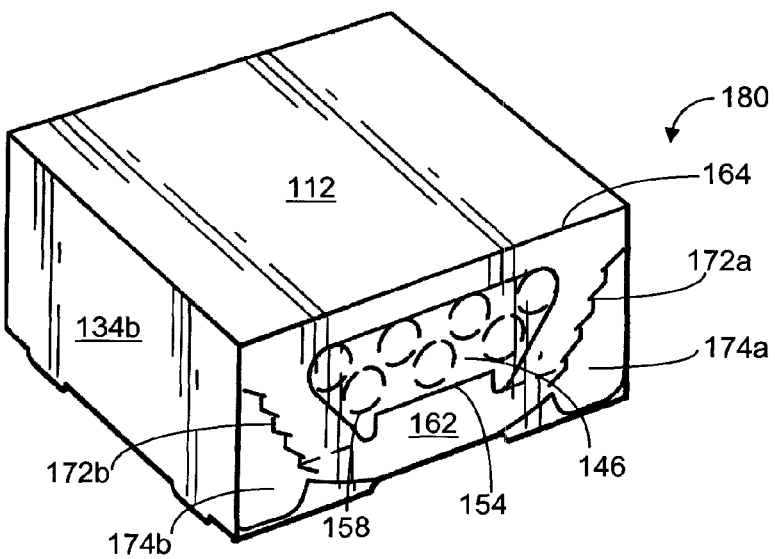
FIG. 5B shows an isometric view of an assembled box without any print placed on the blank.

The blank 110 comprises a top wall 112 that provides a closure for the assembled box 180 that is shown in FIG. 5B. Adjacent to the top wall 112 are two top wall side flaps 116a and 116b that are separated by fold lines 114a and 114b, respectively. The combination of the top wall 112 and the top wall side flaps 116a and 116b provides a printable area that may be configured to receive toner or ink or even a label corresponding to a particular patient. Additional details about an illustrative label defined by the top wall 112 and top wall side flaps 116a and 116b is described below.

A back wall 118 is adjacent to the top wall 112. The back wall 118 is bounded by back wall fold lines 120a and 120b that are adjacent back wall tabs 122a and 122b, respectively. The back wall 118 is separated from the top wall 112 by a top wall/back wall fold line 124.

A bottom wall 126 is adjacent the back wall 118. The bottom wall 126 is bounded by bottom wall fold lines 128a and 128b. The illustrative bottom fold line 128a includes two cuts, namely, cuts 130a and 130a'. Additionally, the bottom fold line 128b also includes two cuts, namely cut 130b and 130b'. The bottom wall 126 is separated from the back wall 118 by a back wall/bottom wall fold line 132.

A first side wall 134a and second side wall 134b are both adjacent to the bottom wall 126. The side walls 134a and 134b are adjacent to side wall fold lines 136a and 136b, respectively.

A first side wall flap 140a is adjacent the first side wall 134a. A second side wall flap 140b is adjacent the second side wall 134b. The side walls 134a and 134b are configured to receive text. Additionally, each side wall flap 140a and 140b comprises a pair of locking tabs including locking tabs 144a and 144a' that are at the outer edge of side wall flap 140a and interface or are "locked" into cuts 130a and 130a'. On the opposite end of the blank 110, locking tabs 144b and 144b' interface with cuts 130b and 130b', respectively.

A front wall 146 is adjacent the bottom wall 126. The front wall 146 is bordered by front wall fold lines 148a and 148b. Front wall tabs 150a and 150b are adjacent the front wall fold lines 148a and 148b, respectively. Additionally, the front wall 146 is separated from the bottom wall 126 by a front wall/bottom wall fold line 152 and an edge slot 154. The front wall 146 also includes a closing slot 156 and a plurality of circular cuts 158 where each cut has a corresponding fold line 160.

A front flap 162 is configured to interface with the closing slot 156. The front flap 162 is adjacent the top wall 112 and both elements are separate by a front flap/top wall fold line 164. The front flap 162 also includes a lip 166 that is bounded by arcuate edge 168a and 168b. The lip 166 is received by the closing slot 156 of the front wall 146. The front flap 162 also comprises an opening 170 that is trapezoidal in shape, has rounded edges, and is bordered by the lip 166 and the arcuate edges 168a and 168b. Additionally, the front flap 162 comprises grooved perforations 172a and 172b that are adjacent cut-outs 174a and 174b. In the illustrative embodiment, the cut-outs 174a and 174b are configured to receive glue or other such adhesive, and are fixedly coupled to the front wall 146. The grooved perforations 172a and 172b are located between cut-outs 174a and 174b and the trapezoidal edge of the front flap 162 that is adjacent the opening 170. The front flap 162 also comprises front flap fold lines 176a and 176b that allow the lip 166 to move about the axis defined by the front flap fold lines 176a and 176b, so the lip 166 can be easily inserted and released from closing slot 156.

Referring to FIG. 5B there is shown an illustrative embodiment of an isometric view of an assembled box 180 without any print placed on the blank 110. The second side wall 134b is shown. The back face of the top wall 112 and the front flap/top wall fold line 164 has been folded over at a 90° angle so that the front flap 162 is coupled to front wall 146 by inserting the lip 166 into closing slot 156.

The front flap 162 has an associated opening 170 that permits an illustrative patient to view a portion of the front wall 146. In the illustrative embodiment, the circular cuts 158 are visible through the opening 170. The front flap 162 has a rounded end that is adjacent the edge slot 154, wherein the edge slot 154 follows the fold line 152 and enables the lip 166 to easily separate from closing slot 156. In the illustrative embodiment, the cut-outs 174a and 174b are glued or fixedly coupled to the front wall 146. When a sealed assembled box 180 is opened, the curved perforations 172a and 172b define where the front flap 162 is perforated and separated from the cut-outs 174a and 174b that become associated with the front wall 146.

Thus, the assembled box 180 is opened when the front flap 162 is lifted and separated from the front wall 146. When the front flap 162 is separated from front wall 146, the front flap 162 may be slightly bent along front flap fold lines 176a and 176b.

Figure 6A:
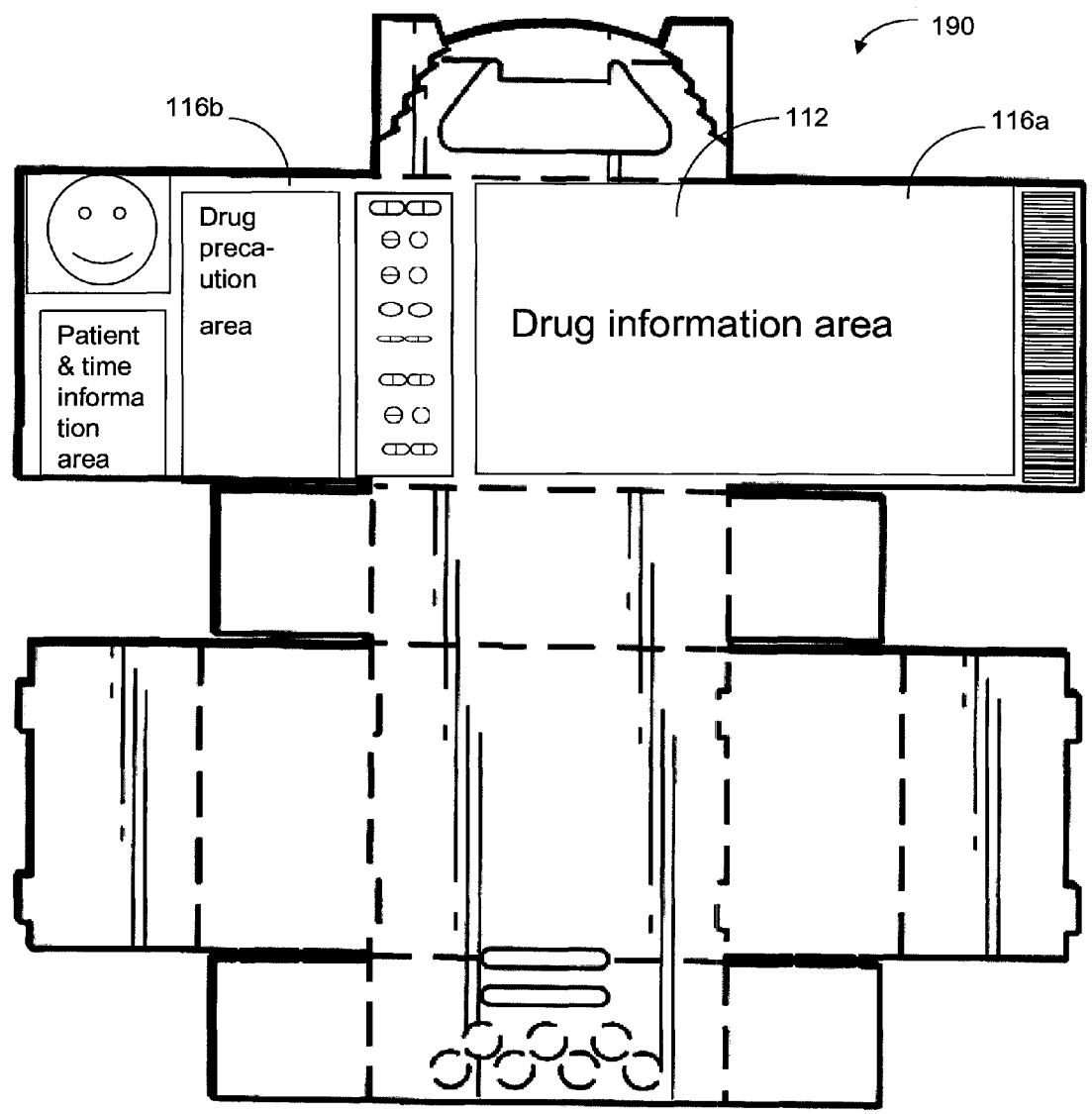
FIG. 6A shows a space for a label on a pre-assembled blank that is similar to the blank described in FIG. 5A.

Referring to FIG. 6A there is shown a label area on a pre-assembled blank 190 that is similar to blank 110 described in FIG. 5A. The information on label 192 is located on the front face of the blank 190 and includes information that is associated with a particular patient. The label 192 may be affixed separately as a separate label, printed on the blank 110 in the label area, or any combination thereof. The label area includes the top wall 112, and top side flaps 116a and 116b described in FIG. 5A.

Figure 6B:
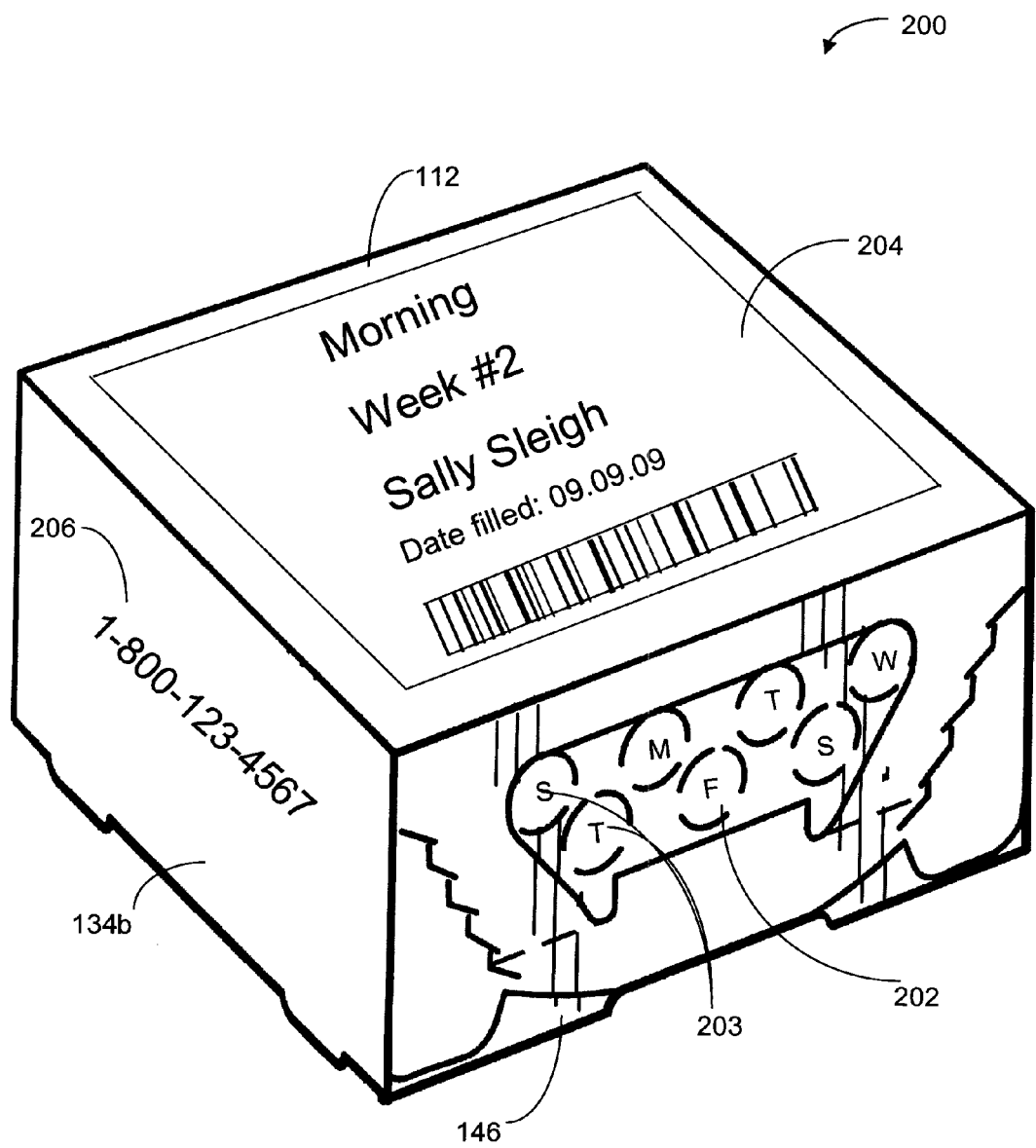
FIG. 6B shows a variety of printable areas on the back face of the assembled box.

Referring to FIG. 6B there is shown a variety of printable areas on the back face of the assembled box 200. The first printable area 202 on the front wall 146 includes printed letters 203 on the circular cuts 158 corresponding to each day of the week where M is Monday, T is Tuesday, W is Wednesday, Th is Thursday, F is Friday, Sa is Saturday, and Su is Sunday. The second printable area 204 on the back face of the top wall 112 and includes the week, the filling date, the patient name, and an illustrative bar code, and an interval or dosage period for the consuming the medications, e.g. Morning. The third printable area 206 is disposed on the back face of second side wall 134b and includes an illustrative 800 number.

Figure 7A:
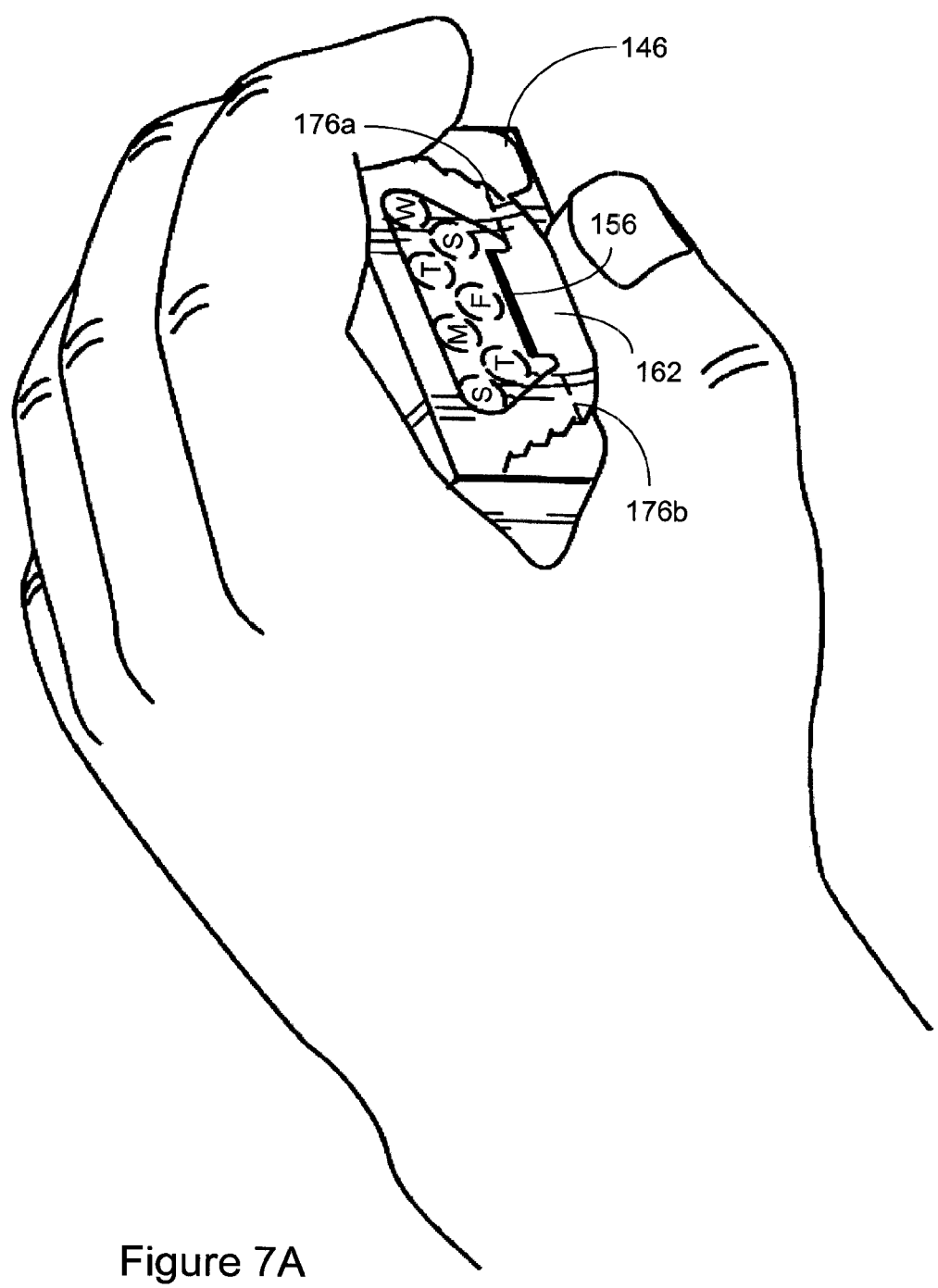
FIG. 7A shows an illustrative method for opening the assembled box with one hand.

Referring to FIG. 7A there is shown an illustrative method for opening the assembled box 200 with one hand. In the illustrative method, the user places his thumb between the front flap 162 and the front wall 146 and lifts the front flap up. The fold lines 176a and 176b allow the lip 166 to move about the axis defined by the fold lines 176a and 176b, so the lip 166 can be easily released from closing slot 156 on the front wall 146.

Figure 7B:
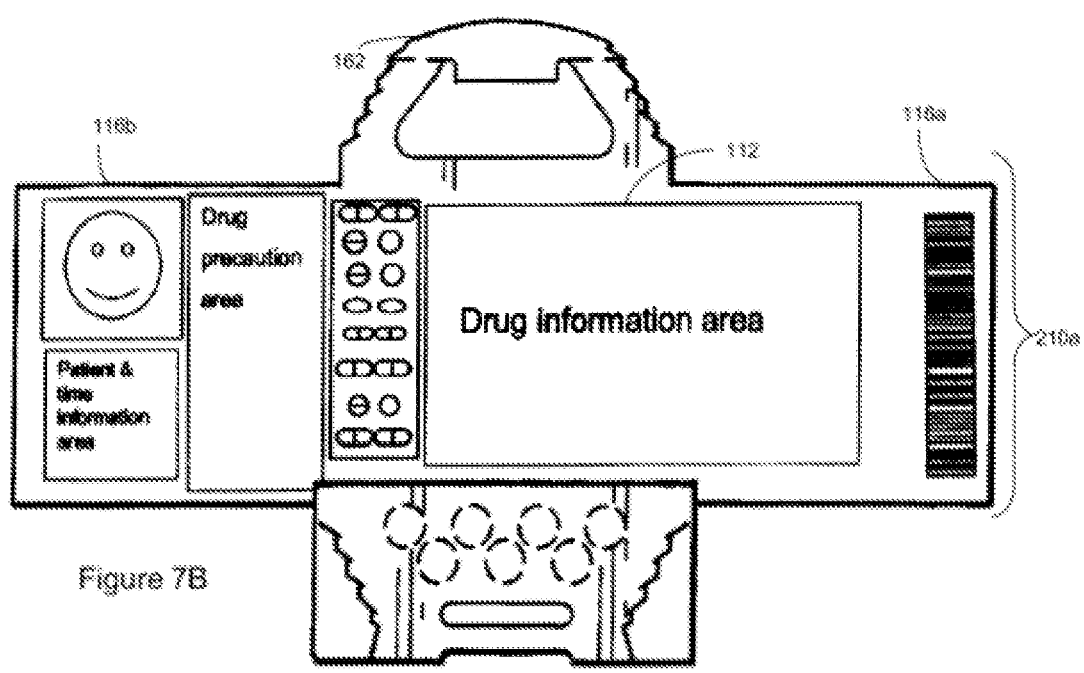
FIG. 7B shows a folded box with an exposed label area or print area defined by the top wall and top side flaps.
Figure 10A:
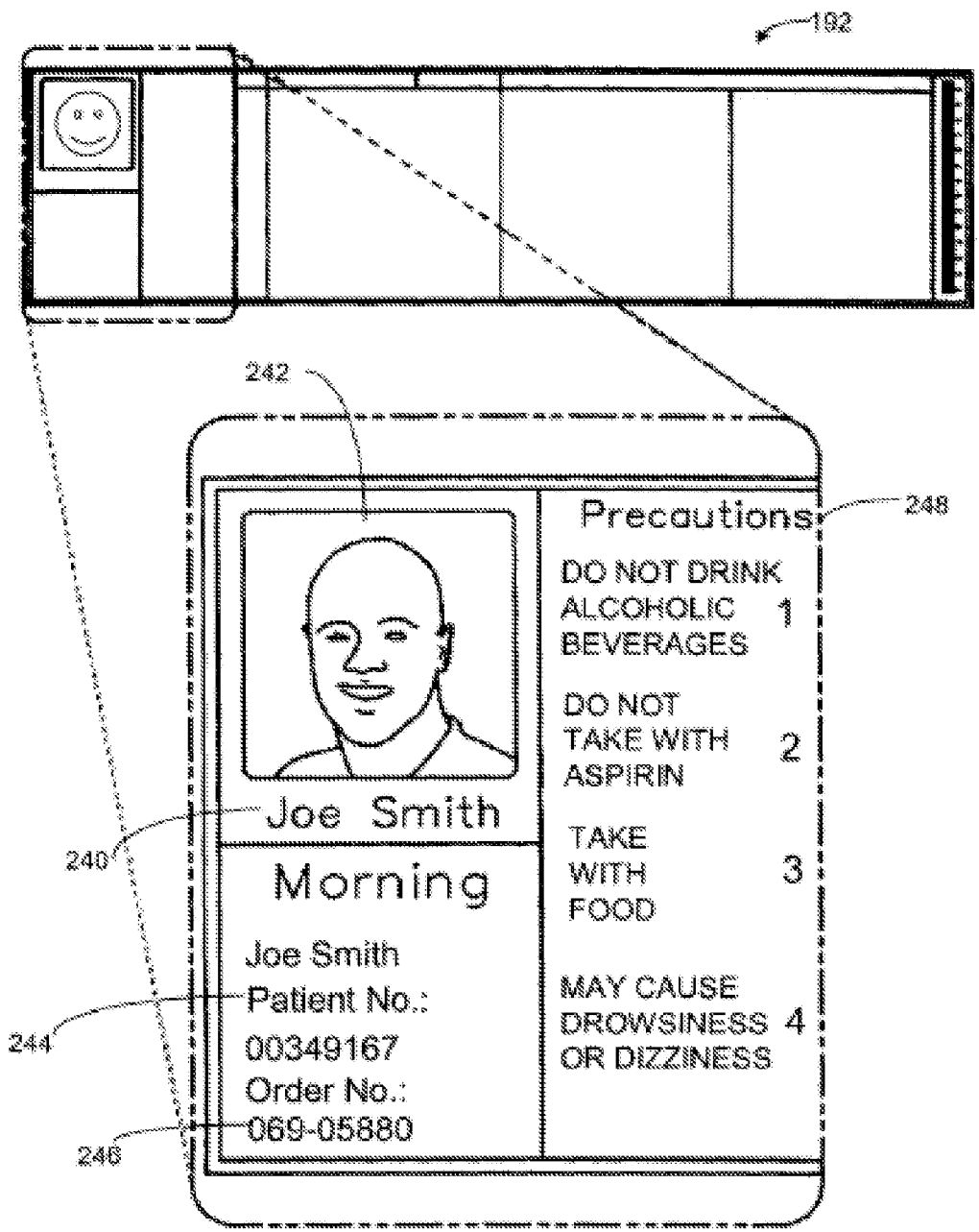
FIGS. 10A-10G show an illustrative label on the folded box.
Figure 10B:
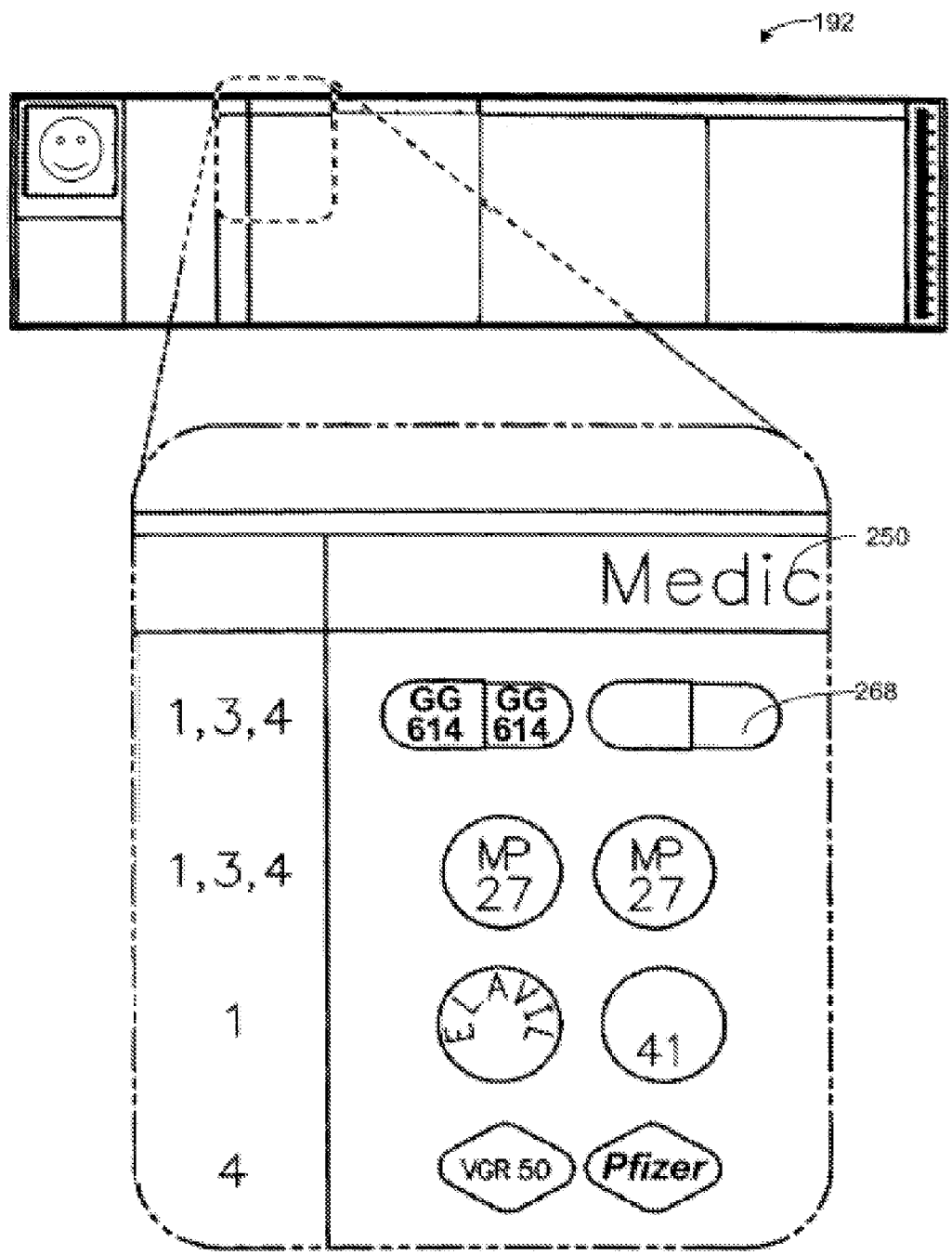
Figure 10C:
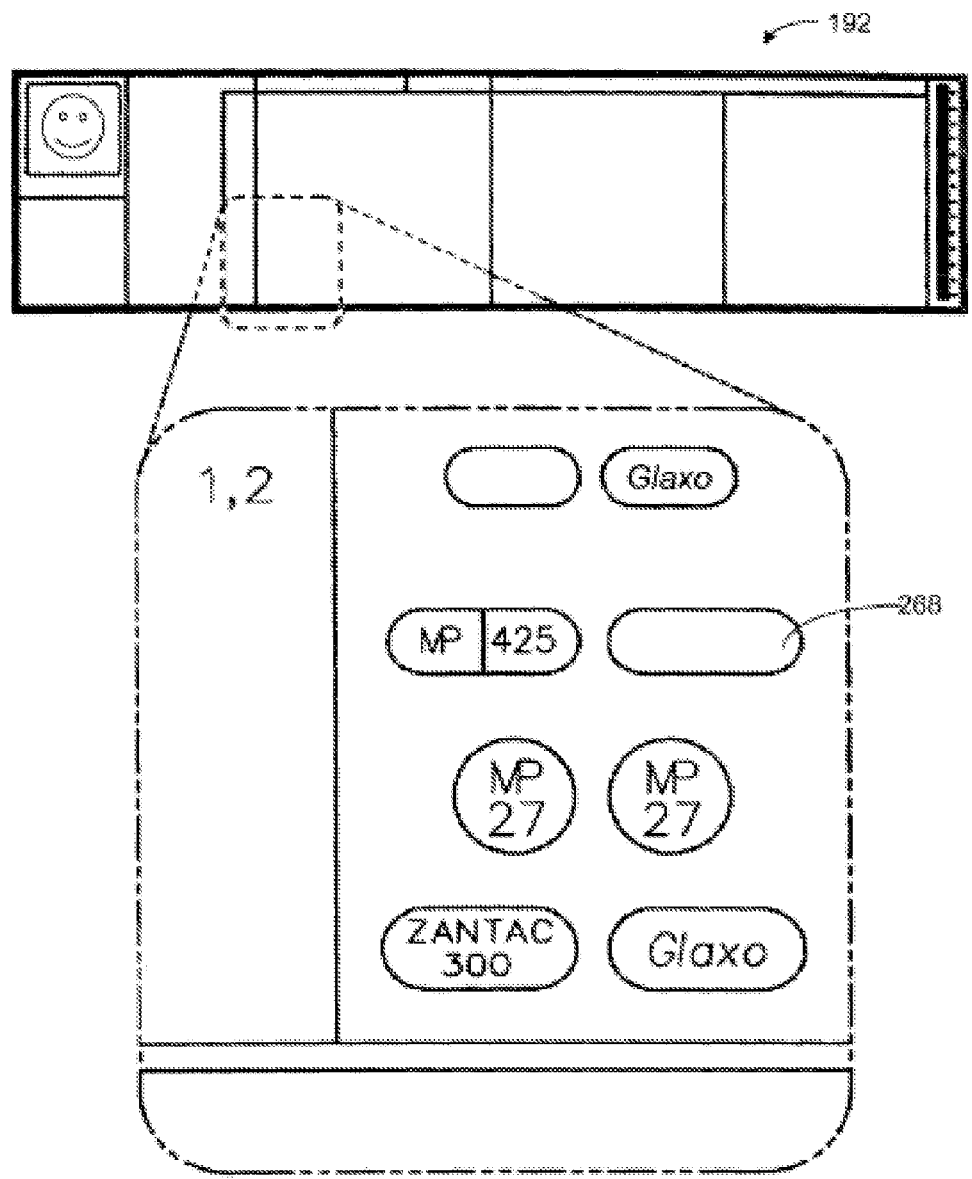
Figure 10D:
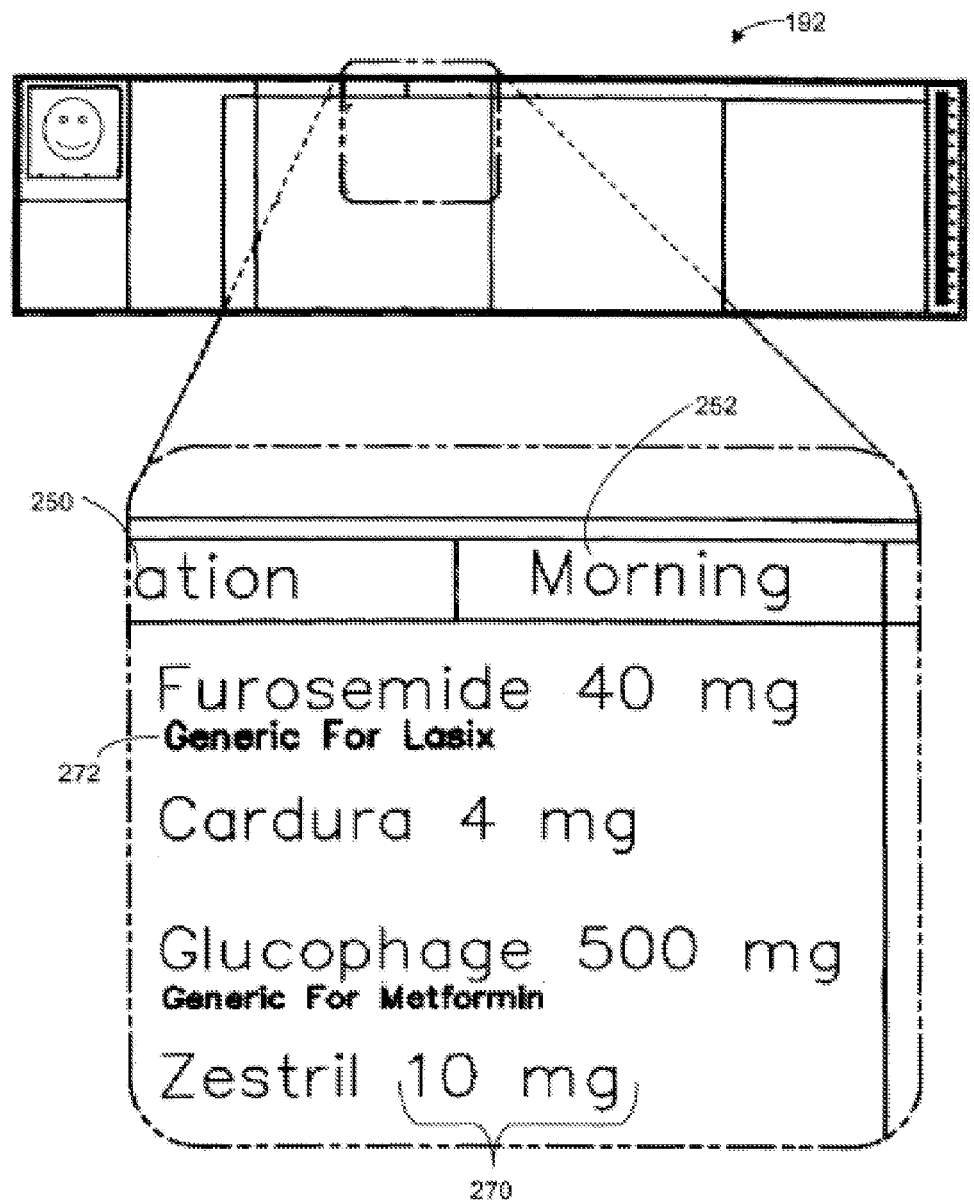
Figure 10E:
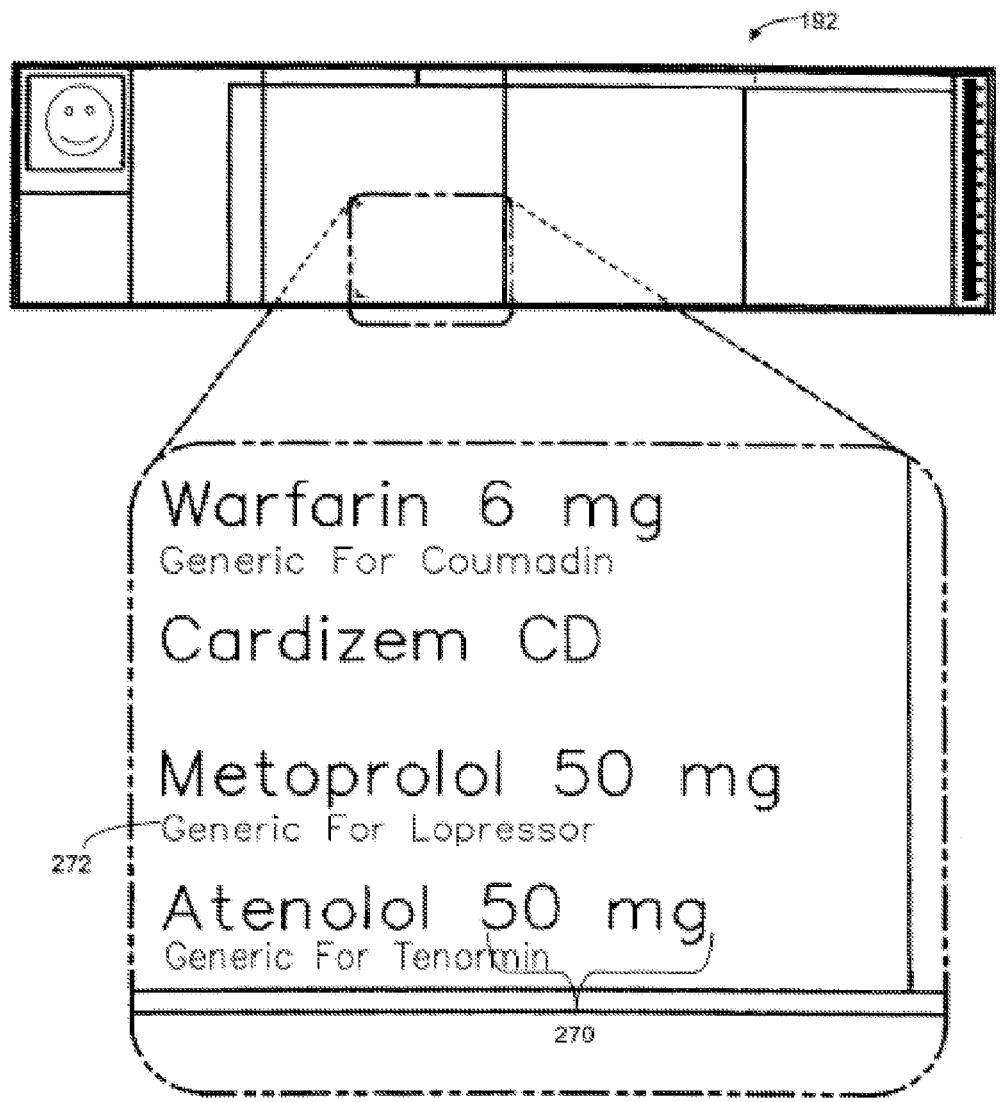
Figure 10F:
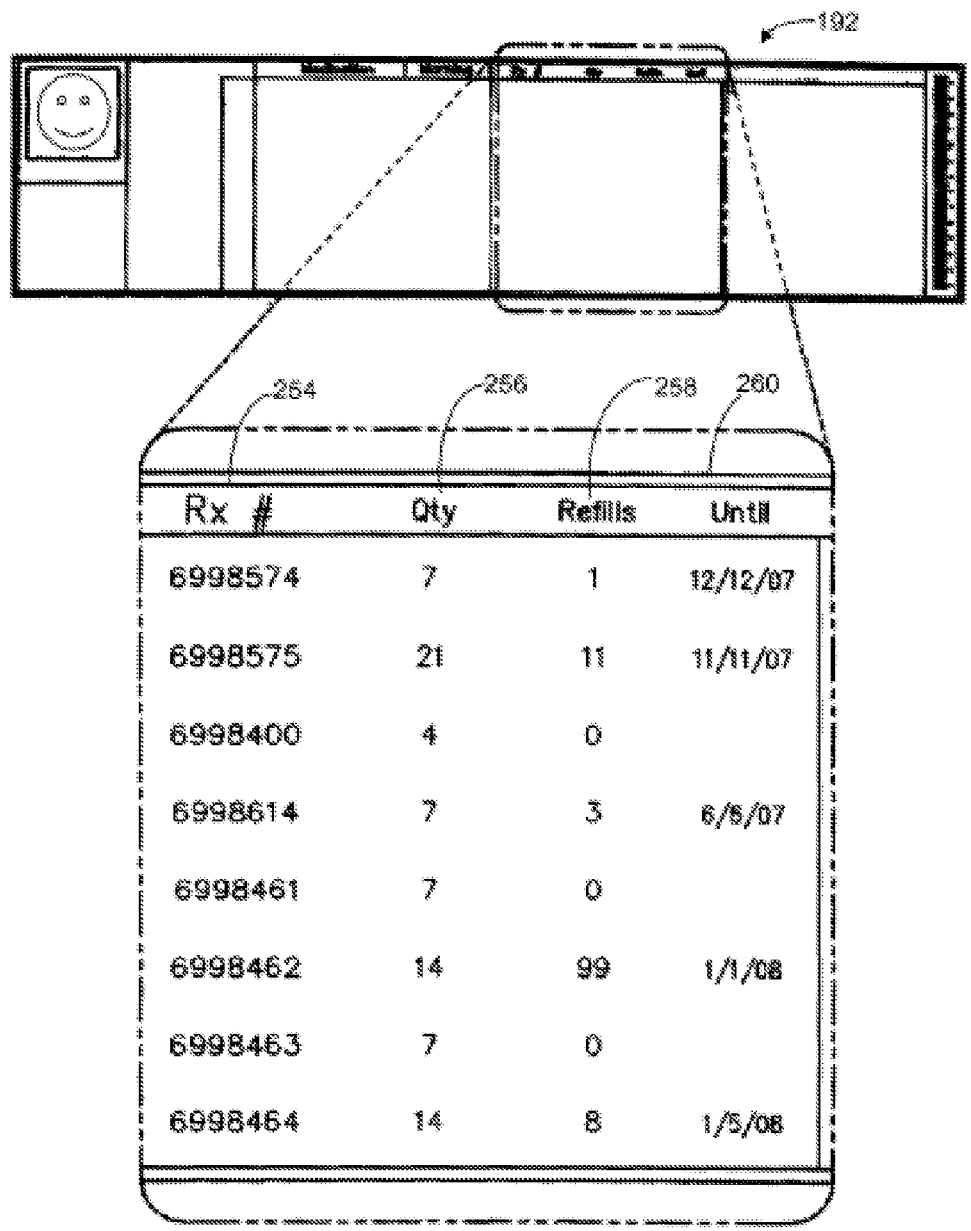
Figure 10G:
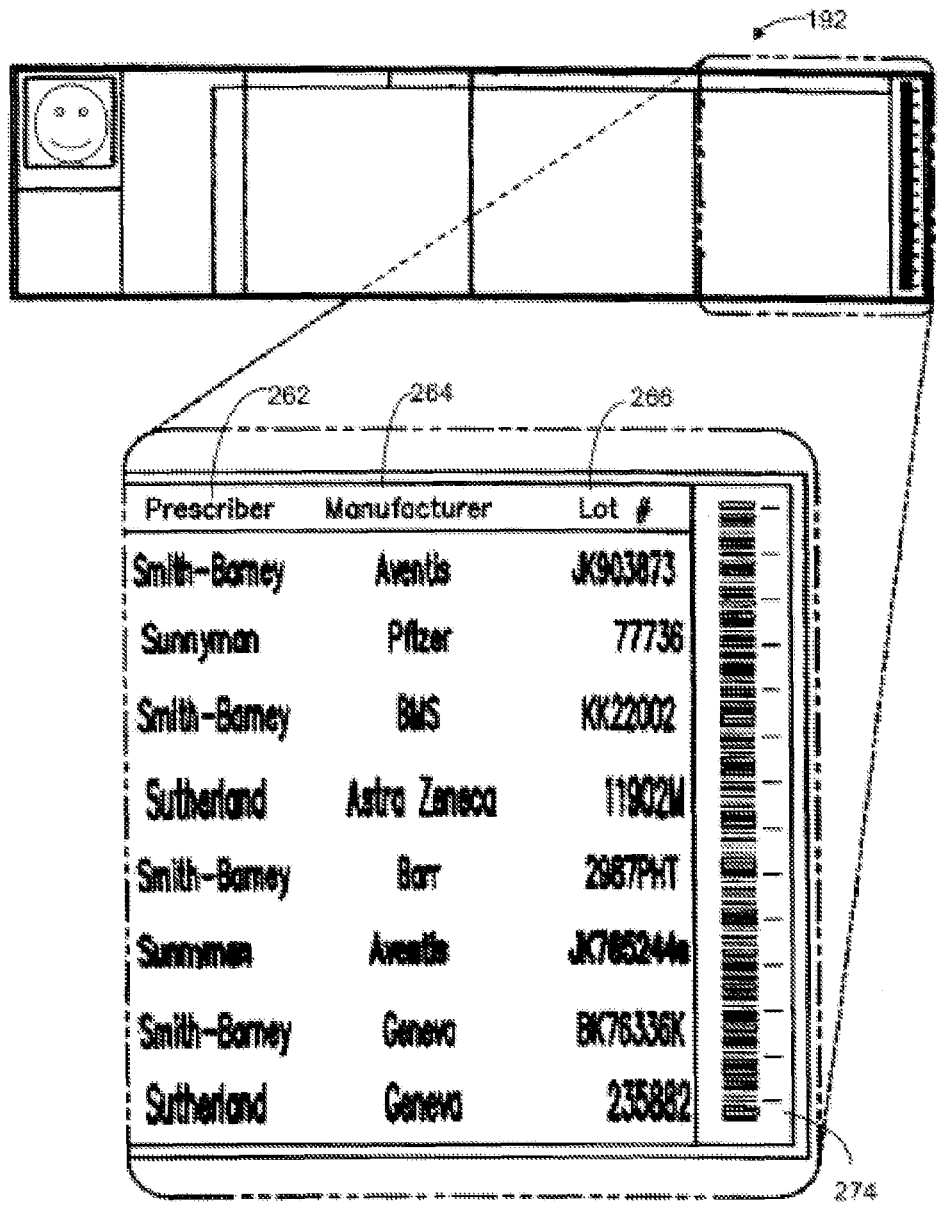

Referring to FIG. 7B, there is shown a folded box with an exposed label area or print area defined by the top wall 112 and top side flaps 116a and 116b as described above. The foldable box comprises a lid 210a and a cavity configured to receive the strip or group of pouches. The illustrative lid 210a includes the top wall 112, top side flaps 116a and 116b, and the front flap 162.

An alternative lid 210b is shown in FIG. 9A and consists of the top wall 112 and the front flap 162. As shown in FIG. 9A, the cavity is defined by the bottom wall 126 adjacent to a back wall 118, two folded side walls 212 and 214, and the front wall 146. Note, the folded side walls 212 and 214 are made by folding first side wall 134a into first side wall flap 140a (see FIG. 5A) about side wall fold line 136a and folding second side wall 134b into first side wall flap 140b about side wall fold line 136b, respectively.

Referring back to FIG. 7B and FIG. 5A, the illustrative lid 210a is adjacent to a back wall 118 (shown in FIG. 5A) that is rotatable along the top wall/back wall fold line 124 (also shown in FIG. 5A). In the illustrative embodiment, the lid 210 comprises the label 192 with a description of the medications housed by the foldable box. Additionally, the label 192 comprises a description of precautions corresponding to the medications as described in further detail below in FIG. 10A.

Referring to FIG. 8A there is shown a side view of a strip of seven separable pouches as shown in FIG. 4A. The separable sealed pouches 220 are folded over along the tearable ribbons so that each pouch is adjacent to the other pouch as shown in FIG. 8A and FIG. 8B, yet connected to one another. Once the pouches are laid over one another, the folded combination 220 is placed in the cavity shown in FIG. 9A.

In the illustrative embodiment each pouch in the strip comprises a date and a period. The date printed on the pouch indicates the date or day when the tablets are to be consumed and the interval or period printed on the pouch indicates the time of day when the tablets are to be consumed.

Referring to FIG. 9A there is shown another illustrative folded box with a label area defined by the top wall. In the illustrative folded box 222, the alternative lid 210b is shown that consists of the top wall 112 and the front flap 162. The cavity that receives the strip of pouches is defined by the bottom wall 126 adjacent to a back wall 118, two folded side walls 212 and 214, and the front wall 146. The top wall 112 is adjacent to the back wall 118 that is rotatable along the fold line 124. The bottom face of the top wall 112 has a label area or print area that is visible when the lid 210b of the folded box 222 is opened. The first area is disposed on the top wall and the first area is configured to receive a description for a plurality of different medications associated with a particular patient.

FIG. 9B shows the illustrative folded box of FIG. 9A in a closed position. The front flap 162 adjacent to the top wall 112 is configured to close the foldable box by rotating the top wall along the fold line 124 and enables the front flap 162 to interface with the front wall 146. A closing slot 156 is disposed on the front wall 146 and is configured to interface with the lip 166 disposed on the front flap 162, when the foldable box is in a closed position. The front wall 146 further comprises an edge slot 154 that is at the interface between the front wall 146 and the bottom wall 126, wherein the front flap 162 is configured to partially cover the edge slot 154. Thus, a means for closing the box is described that includes having the front flap 162 configured to close the foldable box by rotating the top wall 112 along the fold line 124 to enable the front flap 162 to interface with the front wall 146.

Additionally, FIGS. 9A and 9B show that the illustrative box 222 comprises a plurality of indicators corresponding to circular cuts 158 that record when one of the seven pouches in the box has been consumed. The circular cuts 158 are visible through the opening 170 in the front flap 162. In the illustrative example, the front wall 146 comprises seven circular cut-outs 158 that correspond to a seven day week. A record is generated when a patient or caregiver "pushes out" the circular cut. Generally, the patient or caregiver pushes out the circular cut 158 when a pouch is removed from the folded box associated or the tablets in the pouch are consumed. Alternatively, the circular cut outs may be embodied as tear-off tabs. Thus, the circular cuts 158 provide a means for recording that the medications in the pouch have been taken. Other means for recording that the medications in the pouch have been taken include using tear-off tabs, or other such recording means.

Referring to FIGS. 10A-10G there is shown an illustrative label. The label is an exploded view of the label 192. The label 192 may be affixed separately or the label may be printed directly on the cardboard blank 110 in the print area, or any combination thereof. The label area or print area on the illustrative assembled box 200 includes the top wall 112, and top side flaps 116a and 116b as described above. The illustrative label 192 is not visible when the assembled box 200 is closed. Note, the terms "label area" and "print area" are used herein interchangeably.

The illustrative label 192 comprises a plurality of printed text that may include: the patient's name 240, the interval during which the medications are taken, e.g. morning, a picture of the patient 242, patient number 244, order number 246, a list of precautions 248, a listing of the medications 250, a listing of the time interval for taking the medications 252, a prescription number 254, quantity of tablets 256 per prescription, quantity of refills 258, length of prescription 260, the prescribing physician 262, the manufacturer of the tablets 264, and the lot number 266 corresponding to each tablet. Additionally, a picture 268 of each tablet is provided and the dosage concentration 270 is provided for each medication. Information about the associated generic drug 272 is also provided. Furthermore, an expiration date may also be provided for each tablet or for each prescription. Further still, information regarding the generic or trademarked name of the medication may be provided, manufacturer information, corresponding "expiration dates," personal contact information, physician contact information, insurance information, and other such information associated with the tablets in each container.

Further yet, a bar code 274 associates the medications in the foldable box with a particular patient. The bar code 274 provides a means for associating the medications in the foldable box with a particular patient. The illustrative bar code 274 is not visible when the assembled box 200 is in a closed position. Alternative means for associating the medications in the box to the patient include, by way of example but not of limitation, the patient's name, a serial number, a radio frequency identification (RFID) tag, or any other such method for associating an individual with a particular item.

Figure 11:
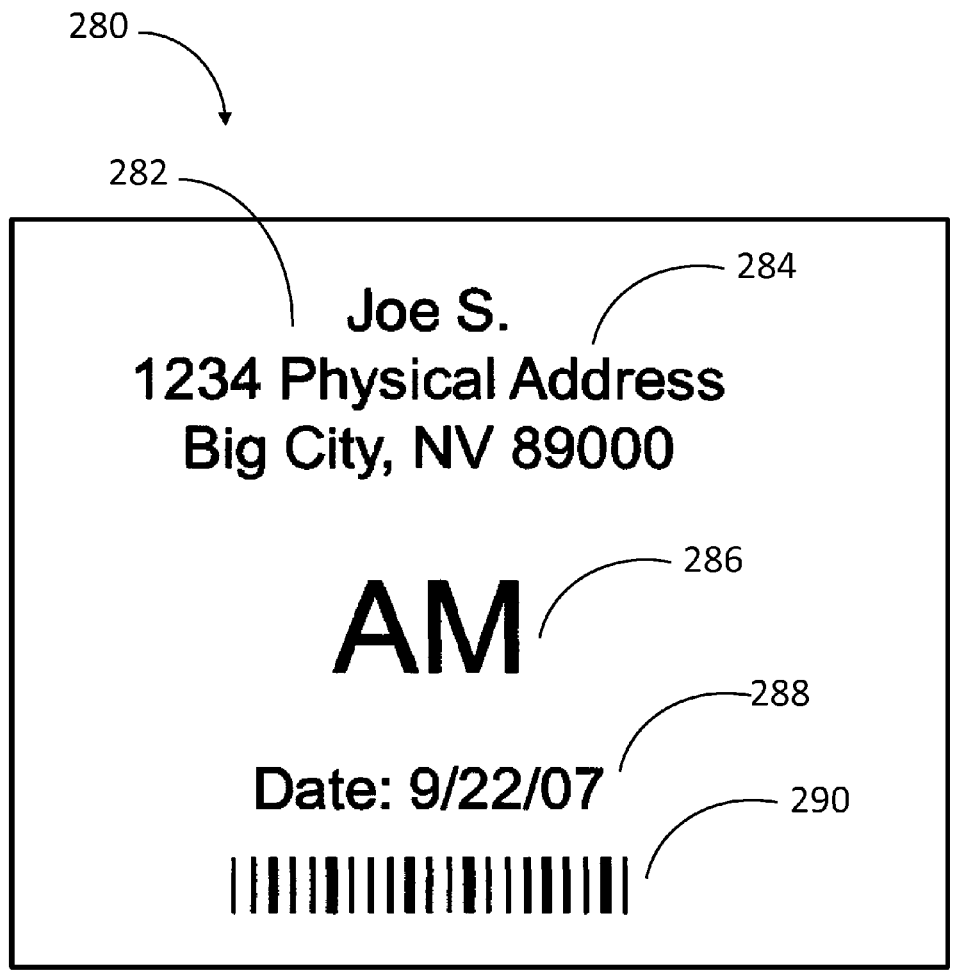
FIG. 11 shows another illustrative exterior label that is applied to the exterior of the assembled box and is visible when the assembled box is in a closed position.

Referring to FIG. 11 there is shown an illustrative exterior label that is applied to the exterior of the assembled box 200 and is visible when the assembled box 200 is in a closed position. The illustrative exterior label 280 includes the patient name 282, the patient's physical address 284, the dosing period 286 e.g. AM, a date 288, and a bar code 290. The bar code 290 associates the medications in the assembled box 200 with the particular patient. Alternatives to using a bar code as a means for associating the medications in the foldable box with the particular patient include using a serial number, an RFID tag, or any other such method for associating an individual with a particular item. The date 288 may be associated with date the prescription was filled, the date that the medication corresponding to the first pouch in the strip, the expiration date for the medications, or another such significant date. By way of example and not of limitation, the dosing period may be one of four dosing periods, namely, morning, noon, dinner, or bedtime. Although not shown, other information may also be on the exterior label may include the week number corresponding to a strip, patient number information, order number information, and other such information.

A means for indicating when the medications in each pouch are to be taken is presented herein. By way of example and not of limitation, the means for indicating when the medications are to be taken include labeling the pouch with dosage period information and including the dosage period information on the interior of foldable box, on the exterior of the assembled box, in a separate booklet associated with the pouches, or a combination thereof.

Figure 12:
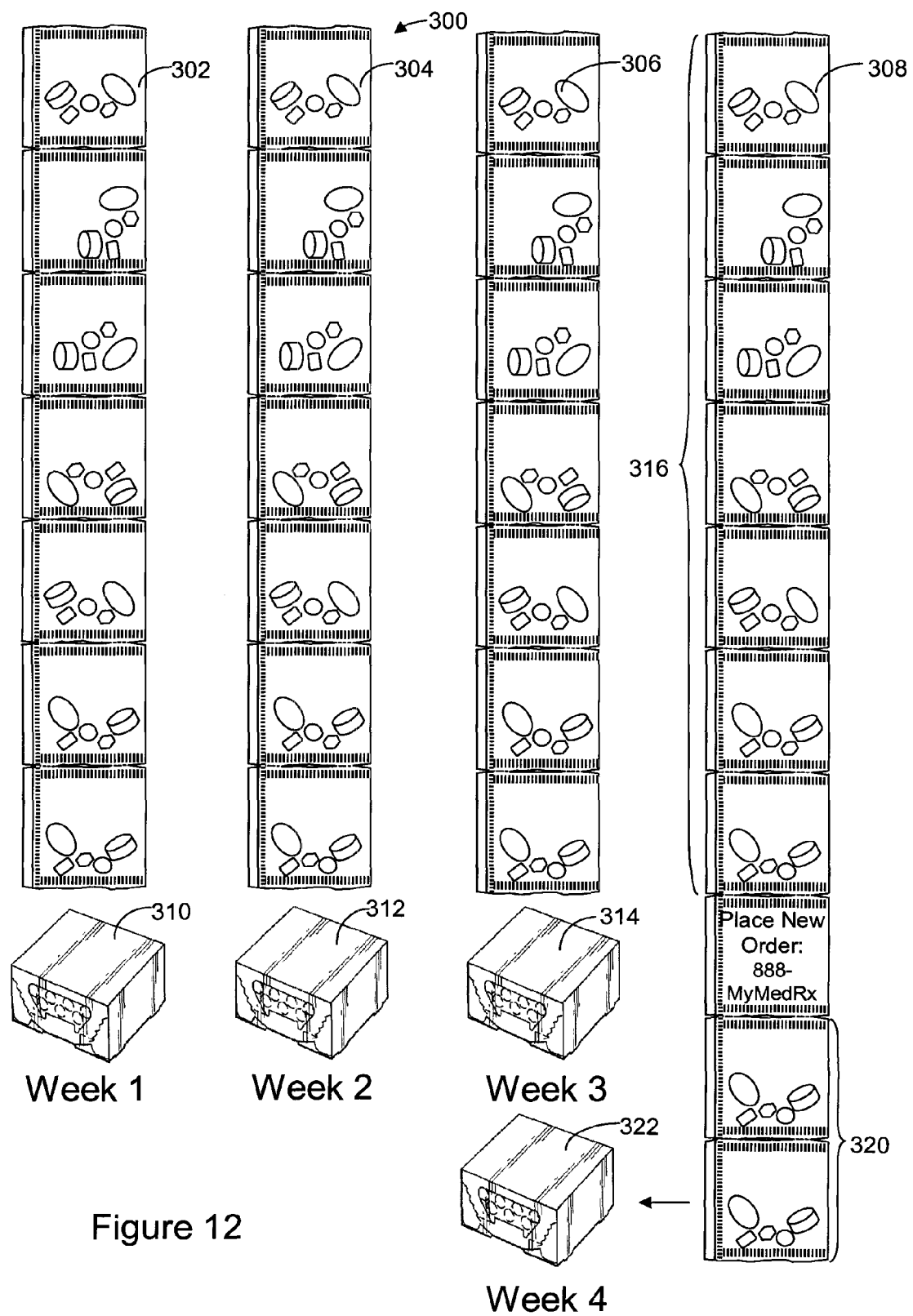
FIG. 12 shows an illustrative grouping for a 30-day tablet regimen for the patient management system.

Referring to FIG. 12 there is shown a 30-day tablet regimen for the patient medication management system that uses the seven-day box. A patient medication management system 300 provides a compliance packaging solution. The patient medication management system 300 described herein provides a compliance package because, firstly, an action is required by the patient or caregiver that requires identifying the appropriate dosage period, e.g. morning, and selecting the appropriate pouch. Secondly, the patient opens the appropriate pouch and consumes the medication. Thirdly, the patient or caregiver records the consumption of the medication by removing or pressing the circular cuts.

The patient medication management system 300 comprises a plurality of sealed pouches that are grouped into four separate strips 302, 304, 306 and 308. The first strip 302 is a seven day strip that covers an illustrative seven day period, Week 1, and is associated with one dosing period. In the illustrative embodiment, the dosage period is selected from the group of dosage period intervals consisting of a morning dosage interval, a noon dosage interval, an evening dosage interval, or a bedtime dosage interval.

The first strip 302 is placed into the illustrative folded box 310 that has the tablets corresponding to the first week of the 30-day regimen. The second strip 304 is a seven day strip that covers an illustrative seven day period, Week 2, and is associated with the same dosing period as Week 1. The second strip 304 is associated with folded box 312 that houses the tablets corresponding to the second week of the 30-day regimen. The third strip 306 is a seven day strip that covers an illustrative seven day period, Week 3, and is associated with the same dosing period as Weeks 1 and 2. The third strip 306 is associated with folded box 314 that corresponds to the third week of the 30-day regimen.

The fourth strip 308 includes a seven day grouping of pouches 316 that covers an illustrative seven day period, Week 4, and is associated with the same dosing period as Weeks 1, 2, and 3. Additionally, an empty pouch 318 is included with the fourth strip 308 that provides a reminder to place another order and an illustrative 800 number to assist in placing the refill order. Furthermore, a two day grouping of pouches 320 covers two additional days. The fourth strip 308 is associated with folded box 322 that houses the tablets corresponding to the fourth week of the 30-day regimen. Thus, the fourth strip 308 includes nine pouches that complete the 30-day regimen.

Each of the strips 302, 304, 306 and 308 are placed in the corresponding folded box 310, 312, 314 and 322, respectively. Each folded box or "primary container" is configured to receive at least seven pouches. Note, the terms folded box, assembled box, and "primary container" are used interchangeably though out this patent. Thus, each primary container is configured to receive at least seven pouches that correspond to the particular dosage period and the illustrative primary container is labeled with the dosage period corresponding to the medications. Additionally, each primary container may be labeled with the patient name and dosage period as described above.

Each folded box or primary container comprises a plurality of daily indicators corresponding to a seven-day period that are disposed on the primary container. The daily indicators provide a means for recording that the medications in the pouch have been taken. An illustrative embodiment of the daily indicators has been provided above that describes a plurality of circular cuts 158 on the folded box. Each of the daily indicators is configured to indicate that the medications in the pouch have been taken, thereby providing a means for compliance packaging.

In the illustrative 30-day regimen, the sealed pouches associated with strips 302, 304, 306 and 308 include sealed pouches with a plurality of different tablets that correspond to different medications and/or vitamins. The different medications are associated with at least one prescription and each tablet includes an appropriate dosage consistent with the prescription. Each of the sealed pouches is labeled to show the medications in the pouch and labeled with a particular dosage period that includes at least one daily interval for consuming the medications in the pouch.

Figure 13:
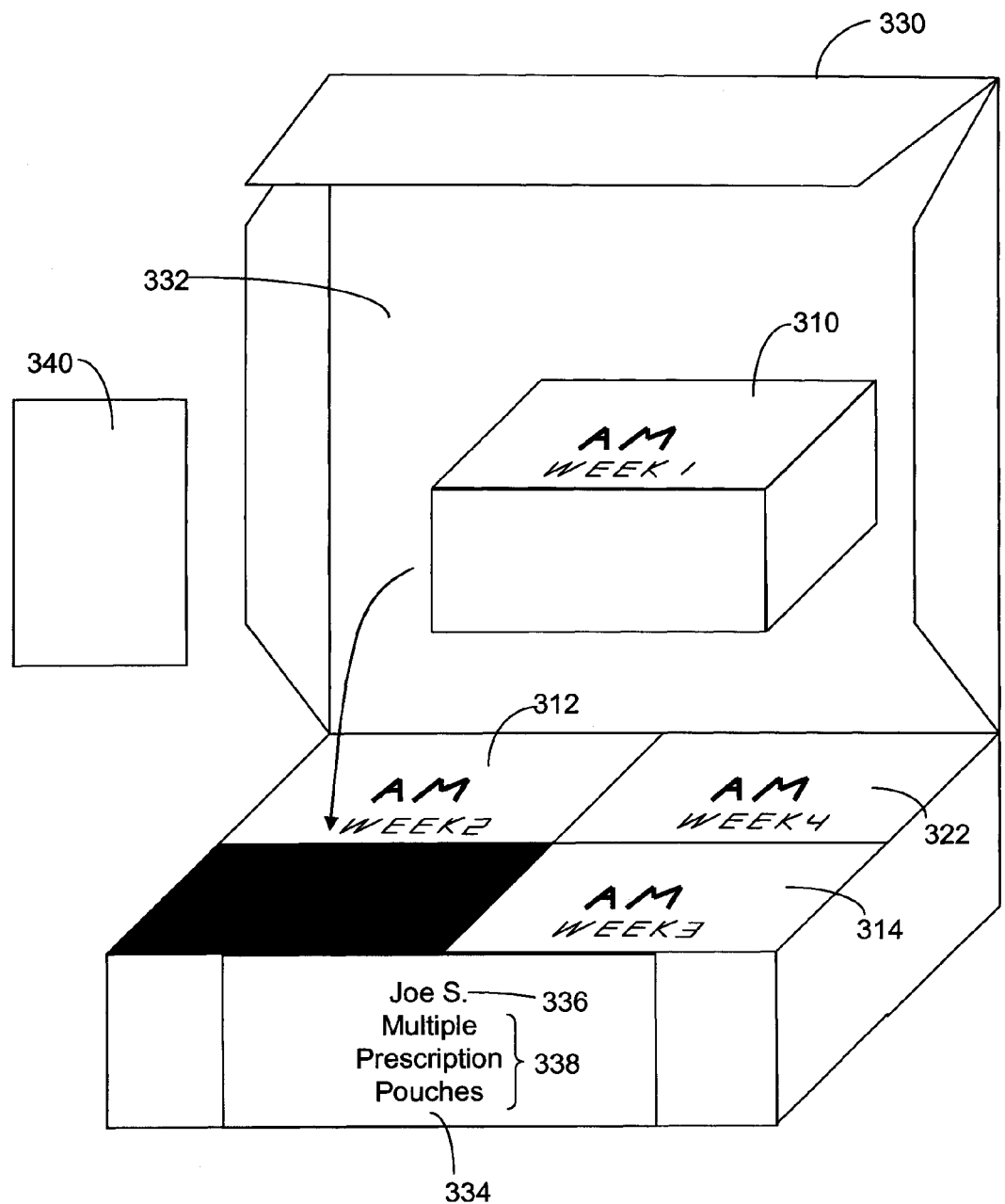
FIG. 13 shows a secondary container that receives four primary containers or assembled boxes.

Referring to FIG. 13 there is shown a secondary container that receives four primary containers or assembled boxes. The secondary container 330 is configured to house the four illustrative primary containers 310, 312, 314 and 322 described above. The illustrative secondary container 330 is composed of a cardboard material. The secondary container includes a lid 332 that is rotatable about a back fold line. The illustrative lid 332 includes a plurality of side flaps.

In the illustrative embodiment, the secondary container 330 is sealed with a label 334 that affixes the lid 332 to the body of the secondary container 330. The illustrative label 334 includes the patient's name 336 and a general description that there are multiple prescription pouches 338 in the secondary container. The illustrative label 334 may also include additional information such as the dosing interval or dosing period, the prescribing physician, one or more bar codes, a patient serial number, or additional information about the different medications, such as the type of prescriptions within the box, the pharmacy that filled the prescription, or any other such information. To open the illustrative secondary container 330, the label 334 is simply broken by the patient or caregiver and access is provided to the 30-day regimen in primary containers 310, 312, 314, and 322.

Additionally, a medication summary sheet 340 may also be included or housed by the secondary container 330. The medication summary sheet 340 provides detailed information about the tablets in each pouch. The medication summary sheet 340 may include warnings, precautions, side effects, dosage, administration, clinical pharmacology, and pictures corresponding to each medication. For example, the medication summary sheet may include summaries of the various medications being taken and summaries of the side effects. In general, the medication summary sheet provides the patient with a detailed summary of the medications being taken. The medication summary sheet 340 may also include the name of the patient, a bar code, or other such identification means that ensures that the correct medication summary sheet 340 is associated with the corresponding prescription.

The illustrative secondary container 330 housing the four smaller containers may be distributed or dispensed at a retail pharmacy, by mail order, or a combination thereof. For the mail order embodiment, a mailing label is also associated with the secondary container. The mailing label enables delivery of the patient medication to a mailing address corresponding to the patient.

Figure 14:
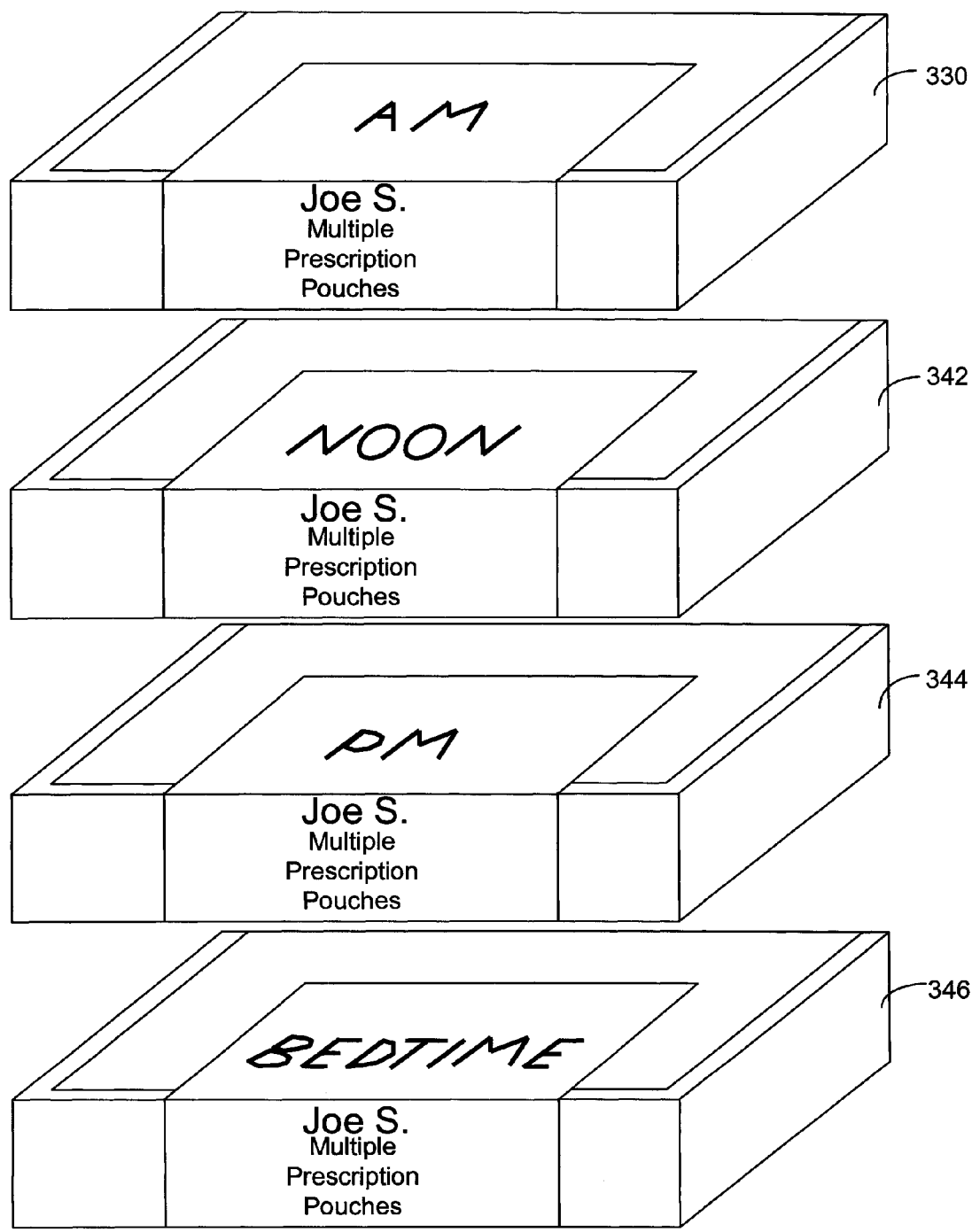
FIG. 14 shows a plurality of different secondary containers corresponding to four different dosage periods.

Referring now to FIG. 14 there is shown a plurality of different secondary containers corresponding to four different dosage periods. In the illustrative embodiment, the first dosage period is the morning dosing period corresponding to the "AM" secondary container 330. The second dosage period is the lunch-time dosing period corresponding to the "Noon" secondary container 342. The third dosage period is the dinner or evening dosage period associated with the "PM" secondary container 344. The fourth illustrative dosage period is the late night dosage period corresponding to the "Bedtime" secondary container 346. Additional dosage periods or intervals may also be necessary and the above dosage periods are illustrative and not limiting.

The secondary containers may also be combined in a tertiary container (not shown). The illustrative tertiary container may be used for shipping purposes or simply to store and transport the secondary containers.

Figure 15:
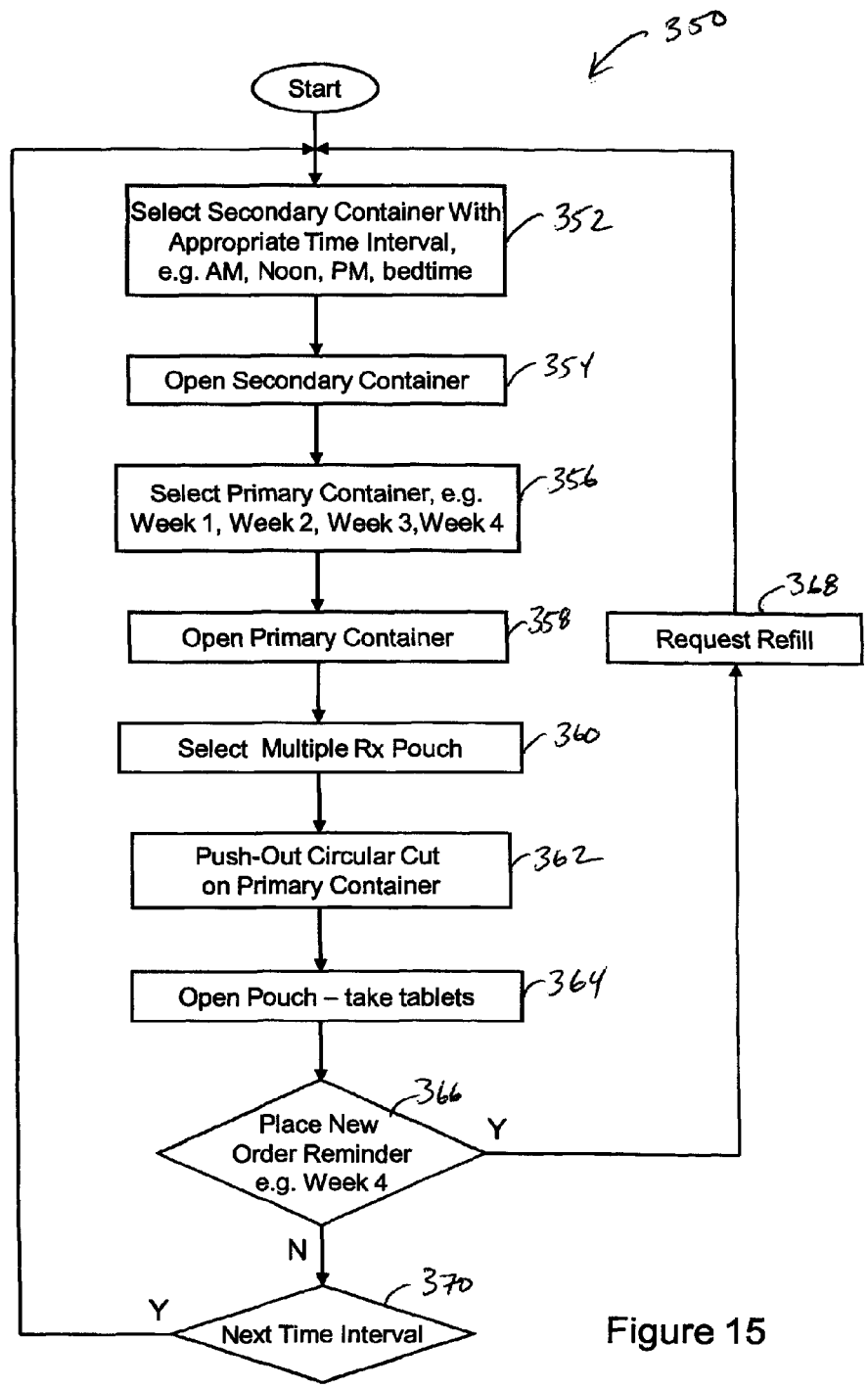
FIG. 15 shows an illustrative flowchart of a method for compliance packaging for the patient medication management system.

Referring to FIG. 15 there is shown an illustrative flowchart for using the patient medication management system described above. The method 350 is initiated at block 352 where a secondary container associated with the appropriate time interval or dosage period is selected. As described above, the illustrative dosage periods are morning, lunch, dinner and bedtime.

The patient then proceeds to block 354 where the patient opens the secondary container and selects the appropriate primary container at block 356. At block 358, the primary container is opened. Subsequently, the appropriate multiple prescription pouch is selected at block 360 and the patient may take or consume the tablets in the multiple prescription pouch.

At block 362, the patient or caregiver then records that the pouch has been removed by pushing out the appropriate circular cut on the primary container. This recording step completes the compliance packaging process. Alternatively, the patient may take the tablets at block 364 after pushing out the circular cut-out.

At decision diamond 366, the patient or caregiver determines whether to place a new order. The decision may be triggered by the empty pouch 318 shown in FIG. 12 that reminds the user that a new order or refill order should be placed, or the decision may be triggered by the patient or caregiver taking their own initiative. The order is then placed at block 368, where an illustrative refill order is placed.

If there is no need to place another order, the primary container is closed and returned to the secondary container that is also closed. The method then proceeds to decision diamond 370 where the patient waits for the next time interval or dosage period. When the next dosage period arrives, the method returns to block 352 and the entire cycle is repeated. Those skilled in the art shall appreciate that various design parameters, requirements, rulings, orders, and statutes may affect the precise method employed.

Compliant packaging may also include a compliant package having a plurality of different tablets corresponding to one or more prescriptions from one or more medical doctors. The compliant package contents are consumed at a predetermined interval consistent with the prescription. Some compliant packaging solutions may not record that each of the tablets is consumed. For example, and illustrative 30-day foldable box configured to receive the plurality of pouches is presented herein.

Figure 16A:
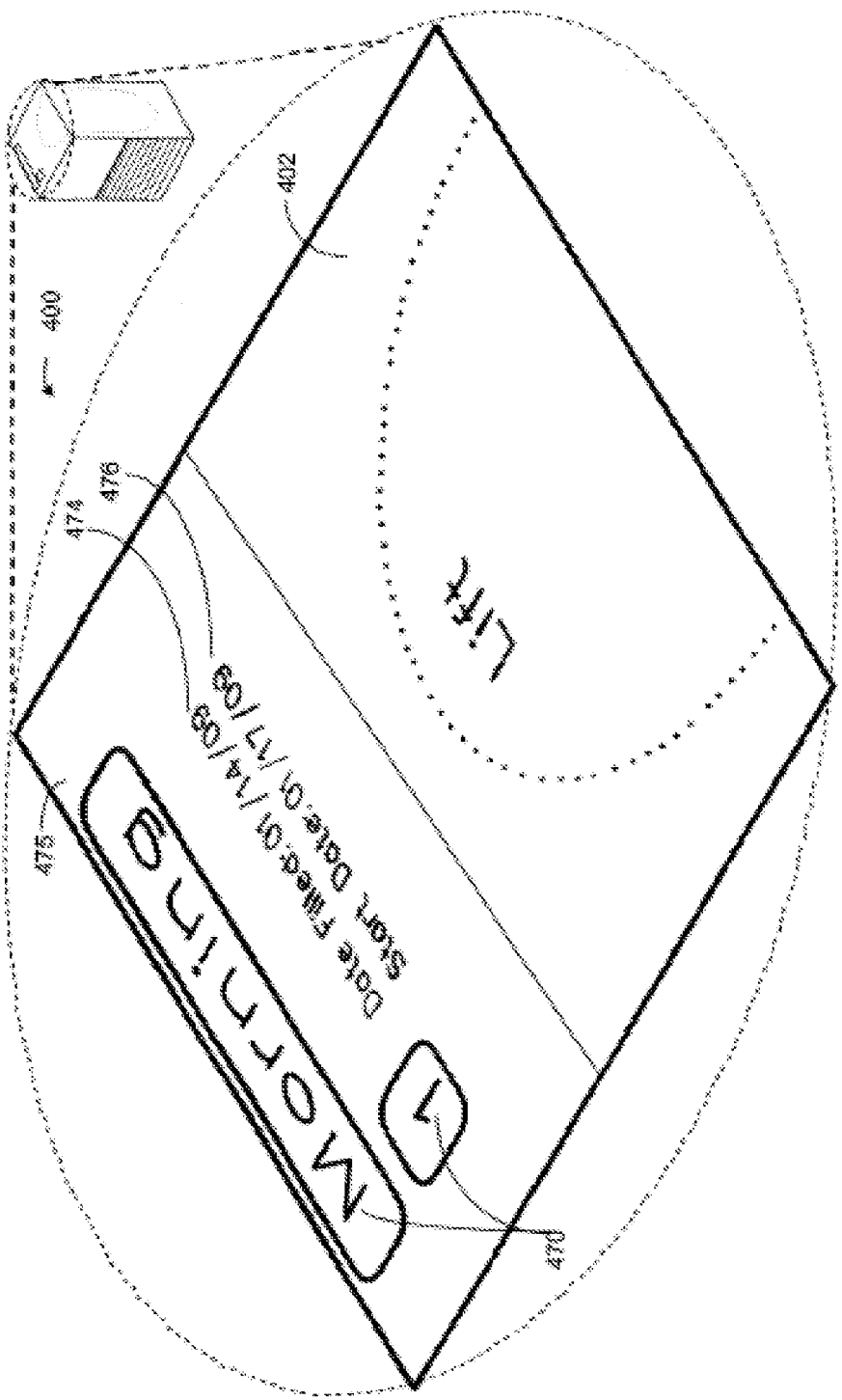
FIGS. 16A-16C show an isometric view of the 30-day tablet dispensing container.
Figure 16B:
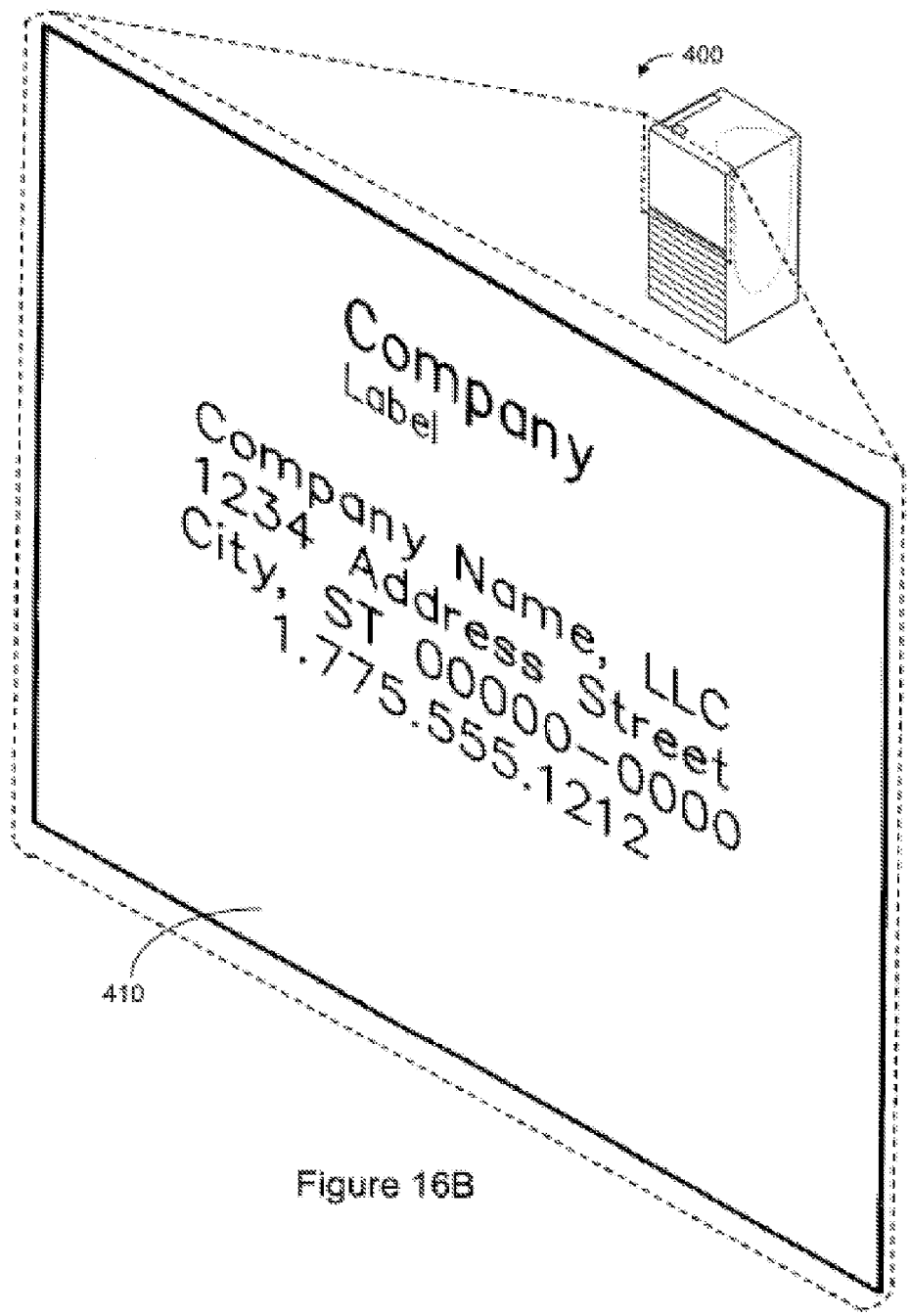
Figure 16C:
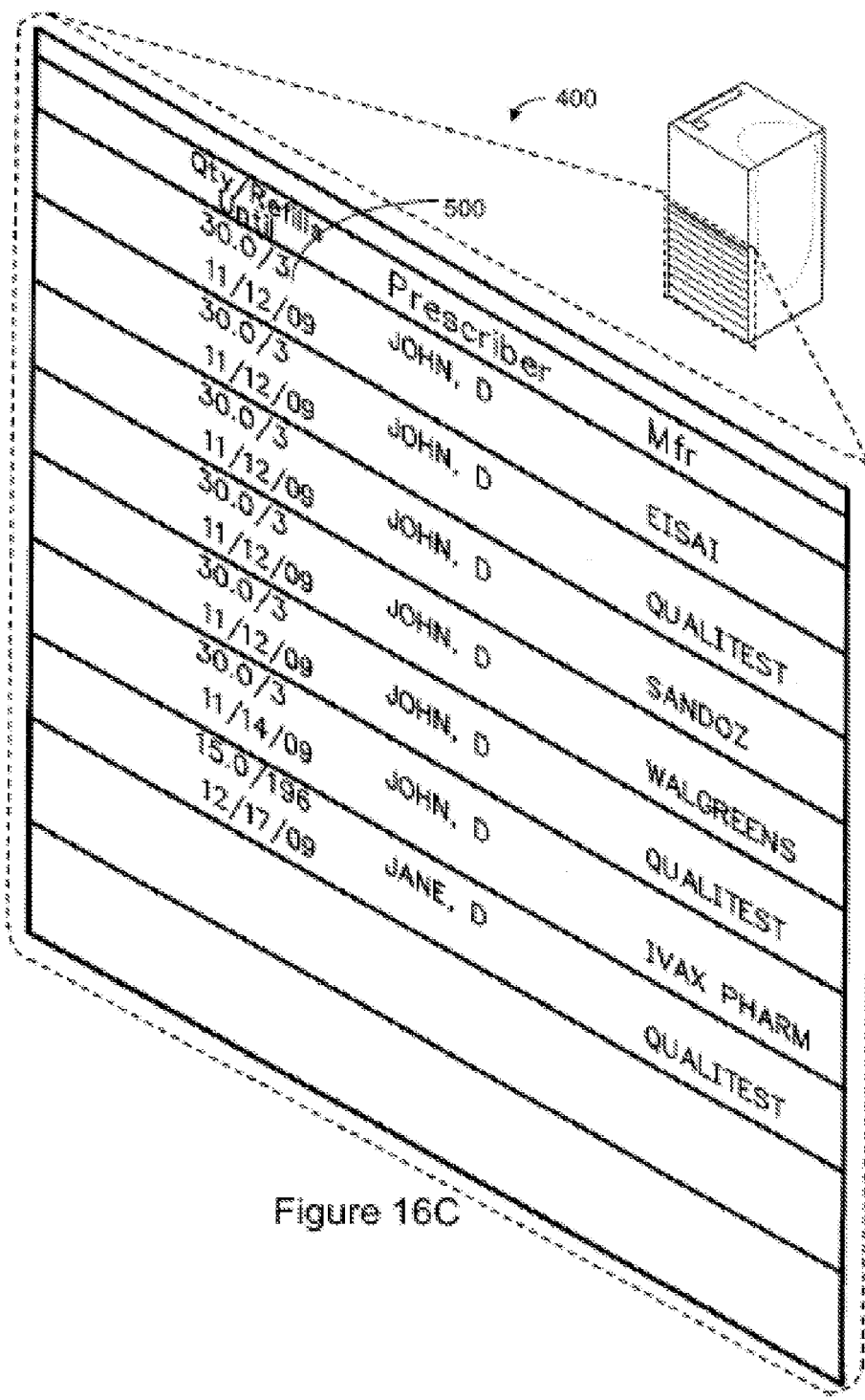
Figure 16D:
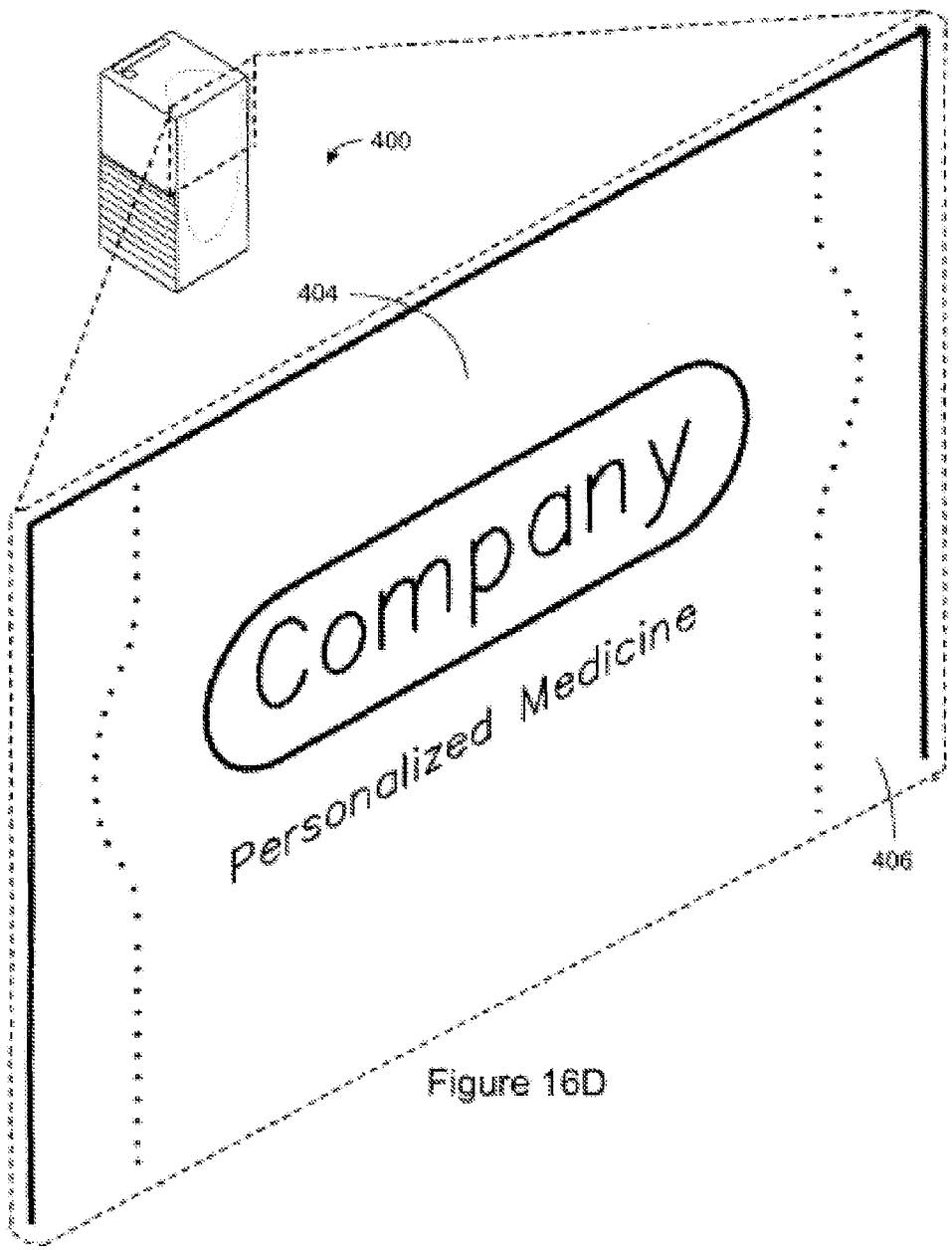
Figure 16E:
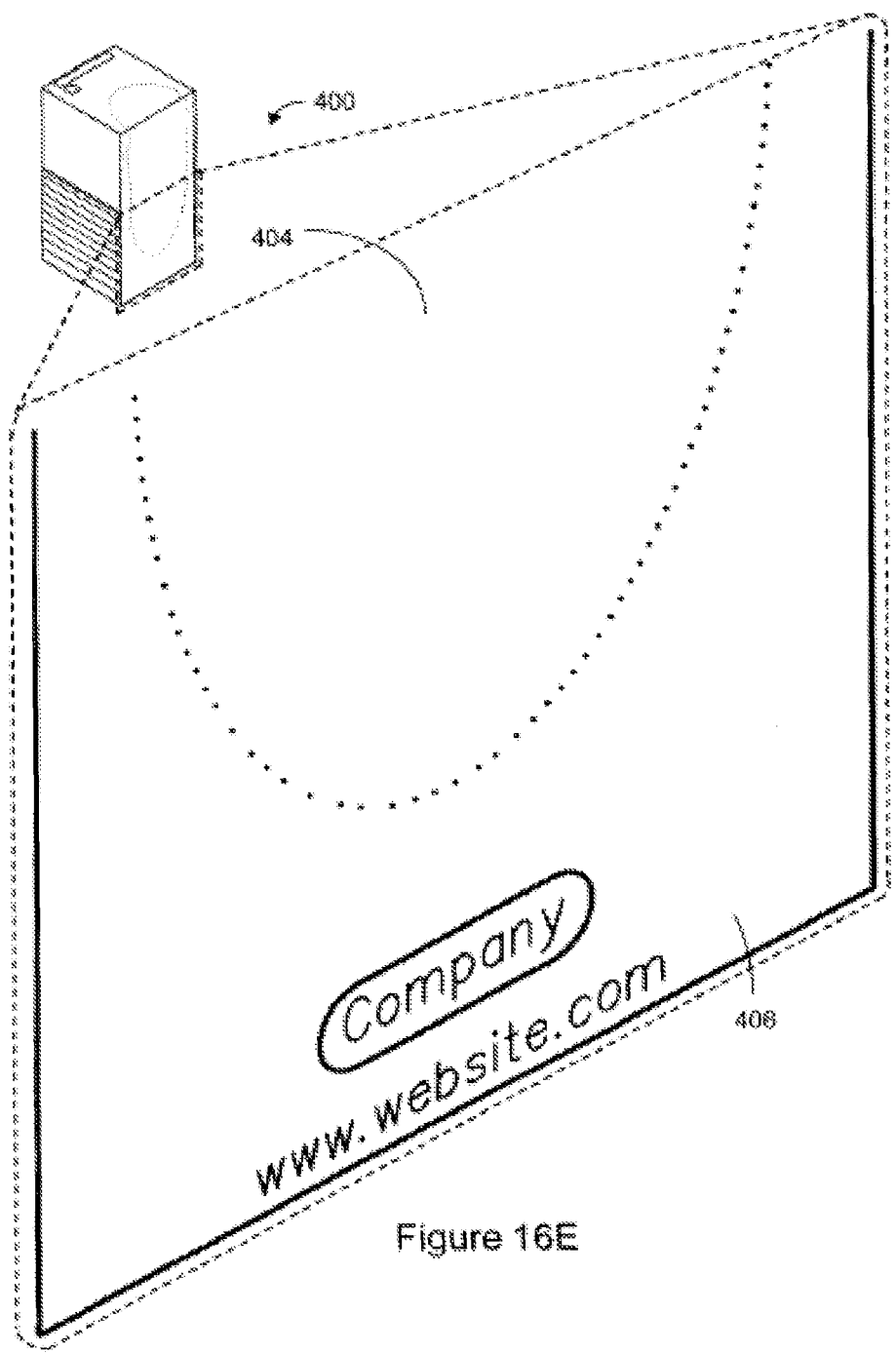

Referring to FIGS. 16A-16C, there is shown an isometric view of the 30-day tablet dispensing container 400. In general, the illustrative 30-day tablet dispensing container is a foldable box that includes a top wall, a front side wall, a right-side wall, a back side wall, a left-side wall and a bottom wall. The top wall has one end fixedly couple to the foldable box and an opposite end that provides a foldable lid. The front side wall has a removable lid that is bordered by a plurality of perforations. The right-side wall abuts the front side wall and the top wall. The back side wall abuts the right-side wall and the top wall. The left-side wall abuts the top wall and is between the back side wall and the front side wall. The bottom wall abuts the front side-wall, the right-side wall, the back side, and the left-side wall. The container is formed to receive a plurality of pouches as described herein.

By way of example and not of limitation, the illustrative cardboard used to construct container 400 includes an outer smooth layer of paper and a thick interior layer. The outer smooth layer may receive printed text or images using an illustrative laser printer, ink jet printer, or other such printing means. Additionally, the outer layer may also be configured to receive a label that is affixed thereto.

In the illustrative embodiment, a perforated, removable lid 404 makes up a large portion of the front side wall 406 and top wall 402 of the illustrative container 400. The lid can be partially or completely removed in order to access the medicament pouches within the container 400. In one embodiment the lid 404 may only occupy one wall such as the front side wall. In the illustrative embodiment, the lid occupies the front side wall 406 and extends to the top wall 402.

The illustrative top wall 402 has one end fixedly coupled to the foldable box and an opposite end that provides a foldable lid. A secondary label 475 is configured to seal the foldable lid on the top wall. In the illustrative embodiment, the secondary label has a bar code (shown in FIG. 19) and includes the time interval when the tablets should be administered or taken. In the illustrative embodiment, the secondary label 475 visible on top wall 402 of the container 400 indicates the time period 470, the filling date 474, and the prescription start date 476 listed above the perforations of lid 404.

A portion of the primary label 500 is visible in FIG. 16, shown affixed to the container 400 such that it covers the lower portion of the left side wall of the container 400. The label goes on to cover the lower portion of the back side wall and right-side wall of the container 400. In the view shown in FIG. 16, the top wall 402, front wall 406, and left side wall 410 of container 400 are visible. The label includes important information related to the prescriptions and to the individual patient for whom the medications were prescribed.

The illustrative primary label 500 may include, for example, patient and medication data such as patient name and number, names of prescribing physicians, medicine(s), dosage strength(s), medicine quantity(s), color images of the medicine(s), prescription number(s), NDA number(s), warning(s), dosage period(s), administration schedule(s), and the like. The illustrative label strip is configured such that all information necessary for drug identification and administration is affixed to the container 400.

The illustrative container 400 comprises a cavity defined by the front side wall, the right-side wall, the back side wall, the left-side wall and the bottom wall, wherein the cavity is configured to receive the plurality of filled pouches that are associated with a bar code. The plurality of filled pouches includes at least 28 filled pouches, in which each pouch comprises a plurality of different tablets associated with a prescription. The barcode is associated with at least one of the pouches, wherein the barcode is associated with the prescription.

Referring to FIGS. 17A-17E there is shown an illustrative primary label 500. The primary label 500 is the large label that is affixed to the side walls. The secondary label 475 is affixed between the top wall and the back side wall. The primary label 500 is affixed to the foldable box and includes a description of the medications and the barcode associated with the prescriptions.

The illustrative bar code provides a means for associating the labels and pouches with a particular patient. By way of example and not of limitation, the means for associating the pouches may also include a radio-frequency identification (RFID) component, writing, or other such associative element capable of associating the labels, pouches, and particular package with a particular patient Starting from the left side of FIG. 17A, the label includes patient and dosage period information including time period 502, patient name 504, barcode 506, patient number 508, and order number 510. Some embodiments, particularly those embodiments suitable for use in a long-term care facility, may also include a photograph (not shown) of the patient in this portion of the label with other identifying information. In other illustrative embodiments, the label may include information about a variety of different prescriptions and medications associated with each of these different prescriptions. Furthermore, the primary label may include an expiration date for each prescription.

The time period 502 refers to the particular time of day that the patient must take the tablets within the container. In this illustrative label, the time period is "Morning." The numeral "1" next to the word "Morning" is another reference to the time period. In this case "Morning" is the first time period during which the illustrative patient must take medications.

Figure 19:
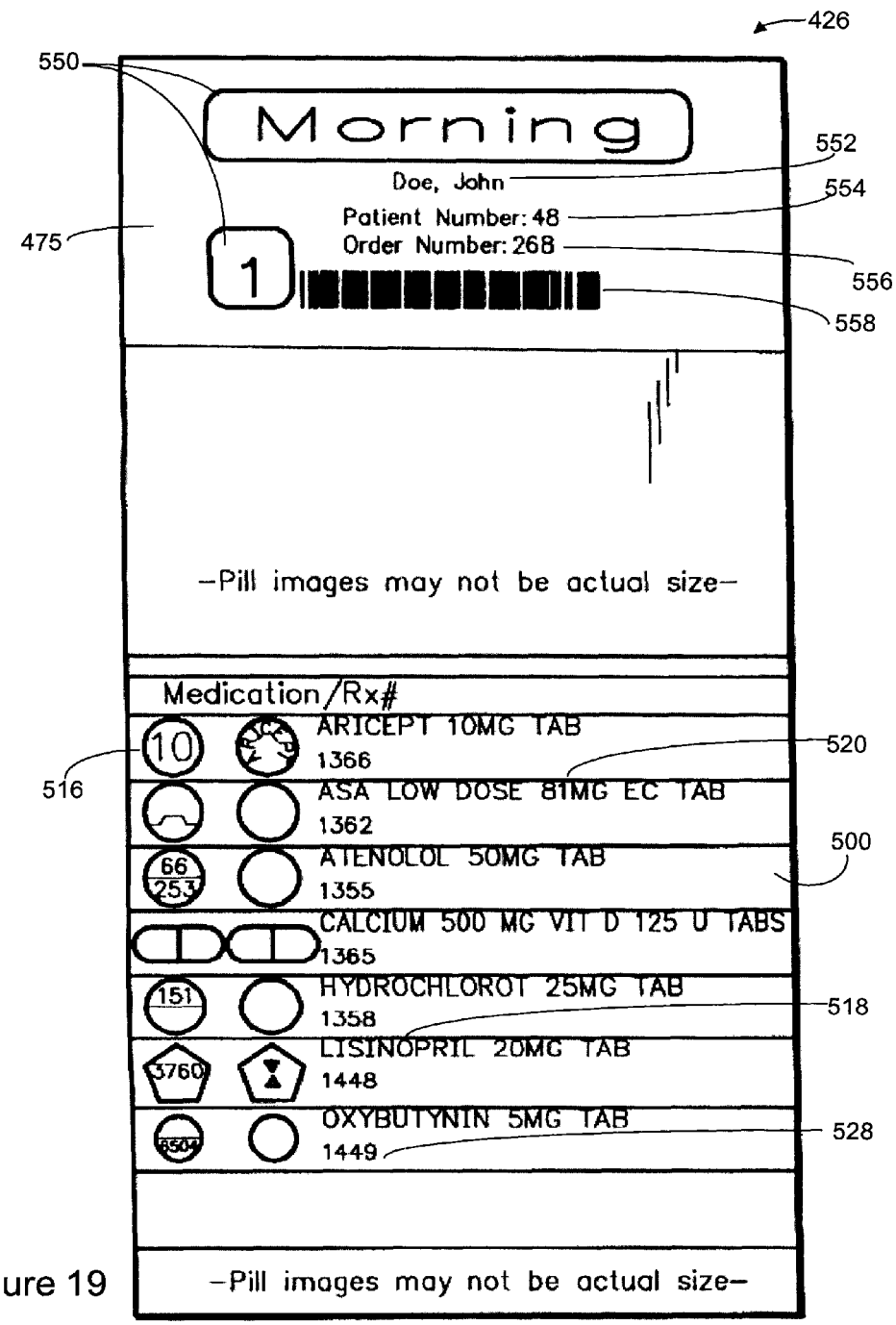
FIG. 19 shows a second side view of the back side wall of the 30-day tablet dispensing container.

A barcode 506 is printed on the illustrative label 500. A barcode may appear on each element of the container and its packaging including the illustrative label 500, the container 400 as shown in FIG. 19, and an illustrative strip of packets or pouches configured to be placed within container 400. The barcodes may encode important information such as time period 502, Patient Name 504, Patient Number 508, and/or Order Number 510. The barcodes are associated with one another during container assembly and filling, improving order verification by ensuring that the appropriate pouches, having been filled with medicaments associated with a particular patient 504 and time period 502, are placed in the appropriate container 400 that is associated with the particular patient 504 and time period 502. Barcodes are also used to ensure that the appropriate label 500 is affixed to the appropriate container 400 associated with a particular patient 504 and time period 502. The barcode may also be associated with a variety of different prescriptions and the corresponding expiration date for each prescription.

Referring now to the "Precautions" section of the illustrative label 500, there is shown a list of drug precautions 514 associated with the medicaments in the illustrative order. Each drug precaution for each drug found within the container is present in the Precautions section. The Precautions section may also include information on synergistic, agonist, or antagonist effects that may occur among one or more medications in the order. Each precaution 514 is associated with a numeral 512A, or with another easy-to interpret symbol. Each precaution applies to at least one drug in the order, but may apply to more than one drug.

The next column of label 500 contains another set of numerals 512B that map to the numerals 512A and thus to drug precautions 514. For example, one of the drug precautions 514 instructs patients to refer to the Patient Info Booklet for additional cautions. The 512A number "6" is associated with the Patient Info Booklet precaution. In turn, the 512B number "6" is associated with several of the prescription tablets 518. Other easily interpreted symbols could be used in place of numbers, but it is essential that the first set 512A maps exactly to the second set 512B.

Figure 17A:
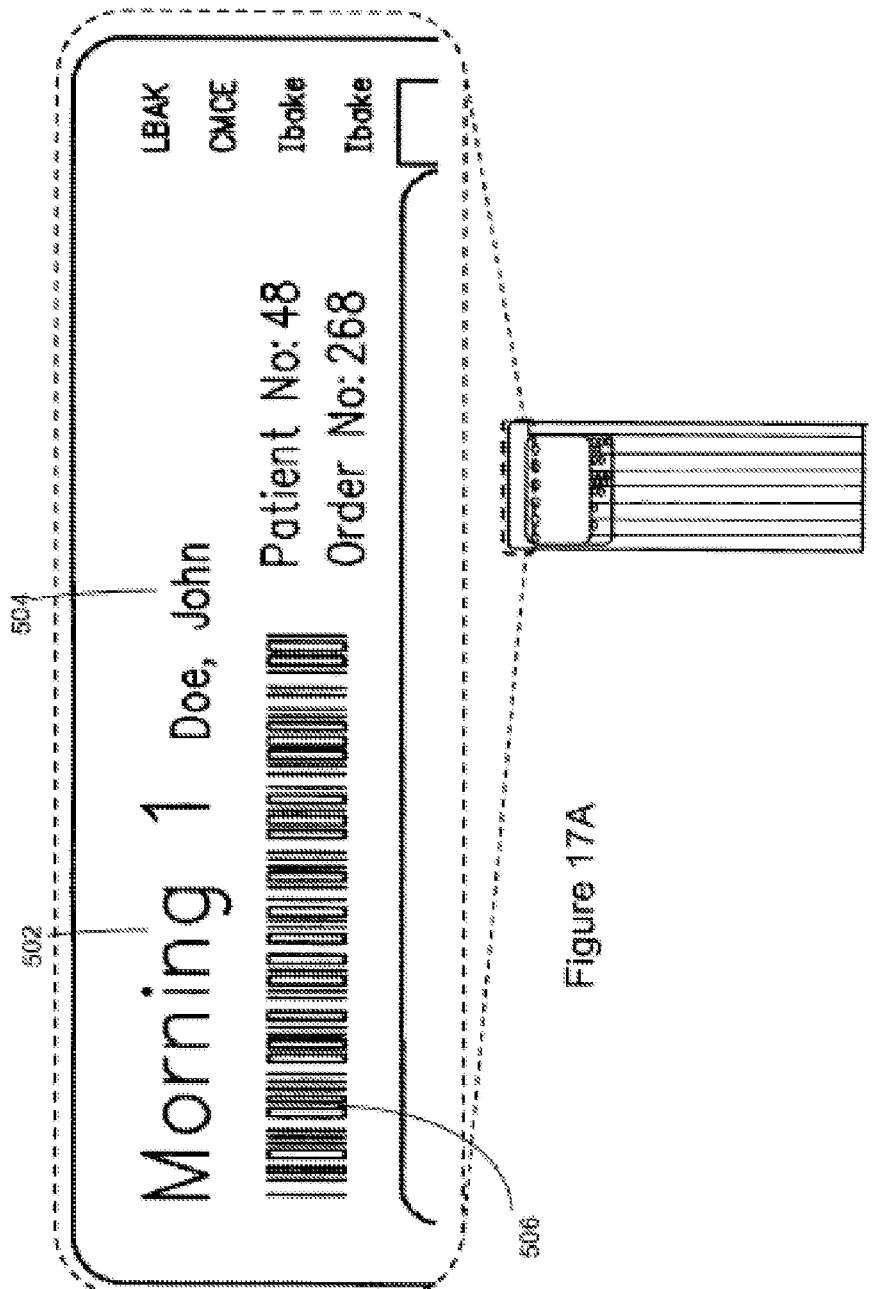
Figure 17C:
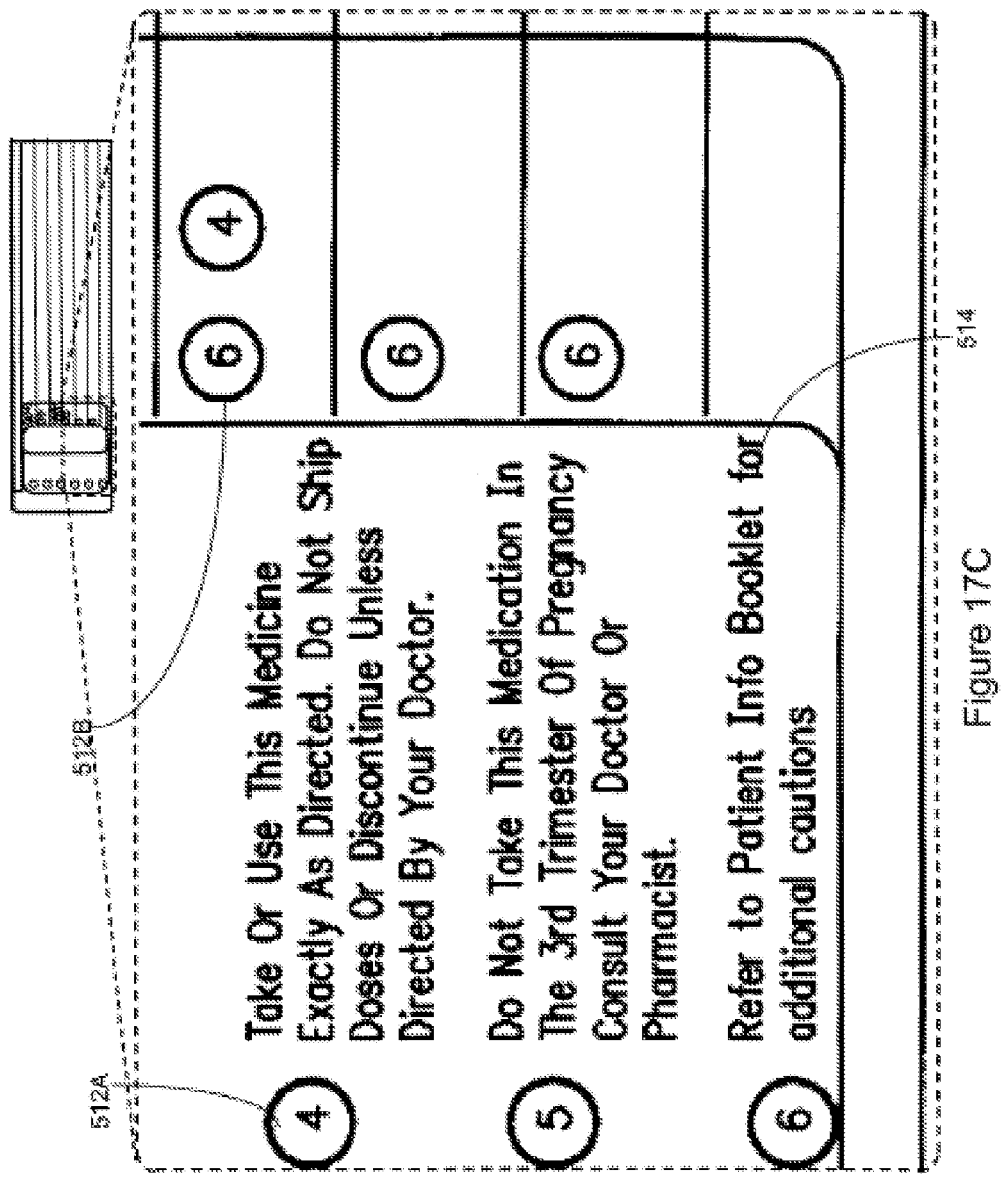
Figure 17D:
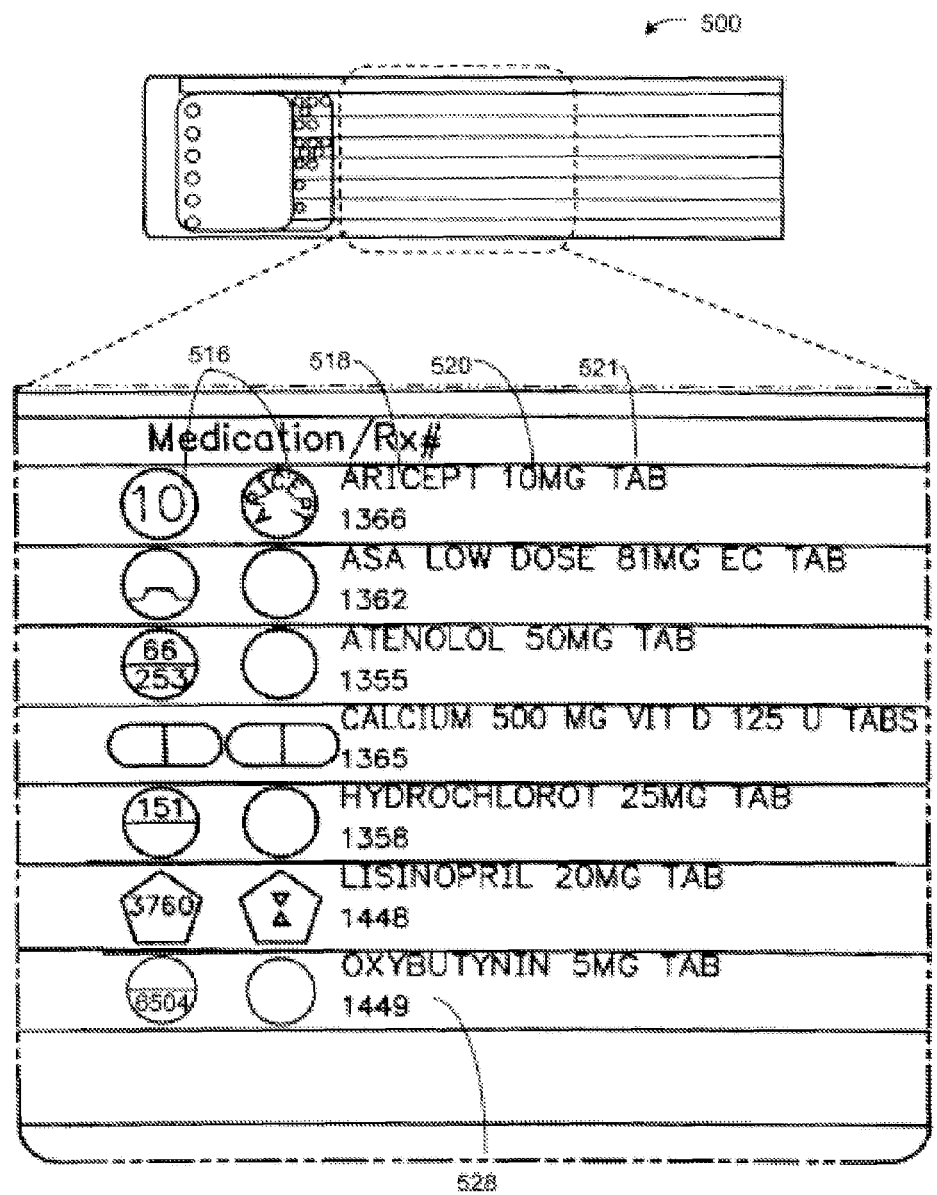
Figure 17E:
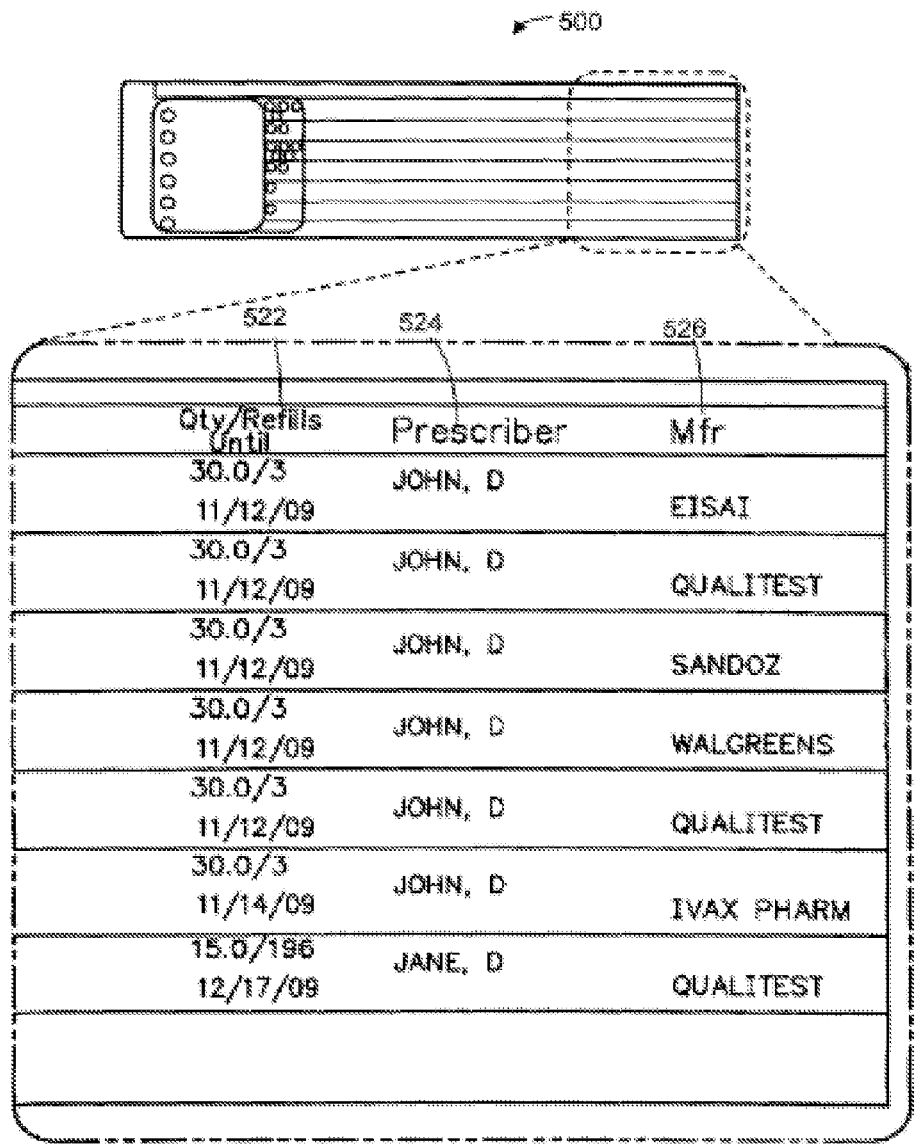

Referring now to FIG. 17D, the next part of the label 500 shows drug information, including color images 516 of each drug in the order and the name 518 of each drug in the order. The numbers 512B are grouped such that each 'cell' containing a group of numbers 512B is associated with exactly one drug 518. The numbers 512B show which listed precautions are associated with each prescription in the order. As shown, each precaution 514 maps to exactly one number 512A, but each precaution 514 and its corresponding number 512B may apply to more than one drug in an order. That is, each number found in the set of numbers 512A may appear associated with any or all drugs 518 in the order, depending on which group of numbers 512B appears next to the drug image 516 and name 518.

For example, on the illustrative label 500, six precautions 514 are shown, each of which is in turn associated with exactly one number 512A. The first drug 518 listed on the label is "ARICEPT." Next to the word "ARICEPT" is shown the color image of the drug 516, and on the other side the 512B numbers "1, 2, 3, & 4" are listed. This means that each precaution 514 associated with each of the 512A numbers "1", "2", "3", and "4" applies to "ARICEPT." Further, the number "4" appears in the groups of numbers 512B adjacent to three of the six illustrative drugs, and number "6" appears in the groups of numbers 512B adjacent to five of the six drugs listed, while the 512B number "5" is listed next to only one drug. This means that the precaution 514 associated with 512A number "5" applies only to one drug, while the precaution 514 associated with 512A number "6" applies to almost every drug in the order.

The "Medication/Rx#" section of FIG. 17B includes the drug images 516 and the drug name 518 mentioned above, in addition to the unit dosage 520, the drug format 521, and the prescription number 528. Thus, a variety of different prescriptions may be consolidated and integrated into the primary label 500. The prescriptions may also include different expiration dates as indicated by the dates in column 522, shown in FIG. 17C. The color images 516 show both the front and the back of each tablet. The color images allow the patient or a caregiver to identify individual medications within each pouch by using the label 500 as a key. If a patient's medication must be changed in the middle of a 30-day prescription order, this allows the patient to keep taking medications from the current 30-day period by merely discarding tablet associated with the discontinued prescription after opening the packet or pouch, and consuming the remaining medications.

The next column of text, shown in FIG. 17C, displays refill information 522 including the number of refills left on the prescription for that drug, the quantity of tablets that is supplied each time the prescription is filled, and the date that the prescription expired. The next column of text includes the prescribing practitioner's name 524 for each drug 518, and the last column includes manufacturer information 526 including the name of the manufacturer or other manufacturer data.

Figure 18:
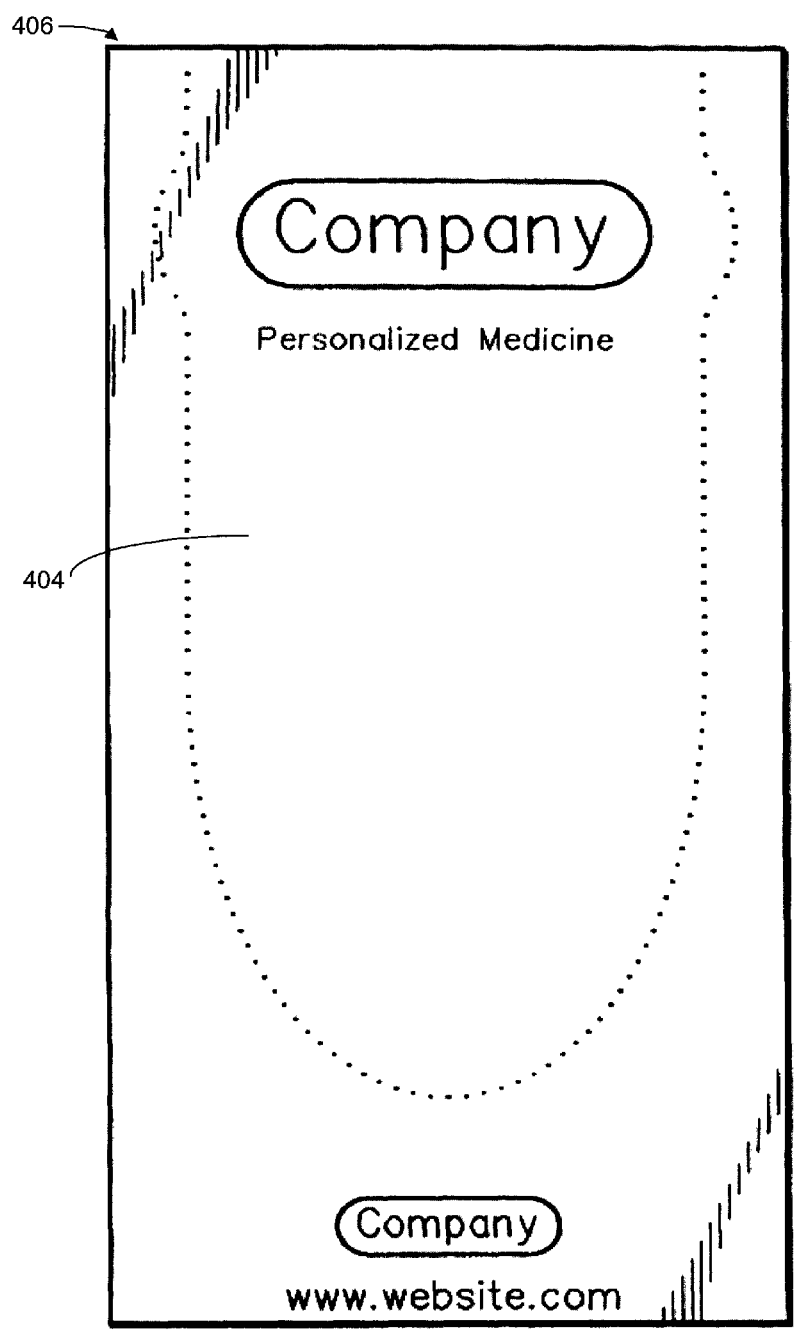
FIG. 18 shows a first side view of the front side wall for the unopened 30-day tablet dispensing container.

Referring to FIG. 18, there is shown a side view of the front side wall for the unopened 30-day tablet dispensing container. The front part of lid 404 is visible on the front side wall. Lid 404 is removed by the patient or a caregiver in order to access the contents of the container 400. By way of example, the front lid 404 and the space below the lid have areas that display the name of the pharmacy that provides the container 400.

Referring to FIG. 19 there is shown a side view of the back side wall of the 30-day tablet dispensing container. Part of the primary label 500 is shown affixed to the lower portion of the back side wall 426 of the container 400. Additionally, part of the secondary label 475 is also shown. The visible portion of the primary label 500 includes the medicament images 516, the drug name 518, the dosage amount 520, the dosage format 521, and the drug number 528 is shown. The upper portion of the back side wall 426 of container 400 includes a portion of the secondary label 475 that also has additional printed information that includes dosage period 550, patient name 552, patient number 554, order number 556, and barcode 558.

Figure 20A:
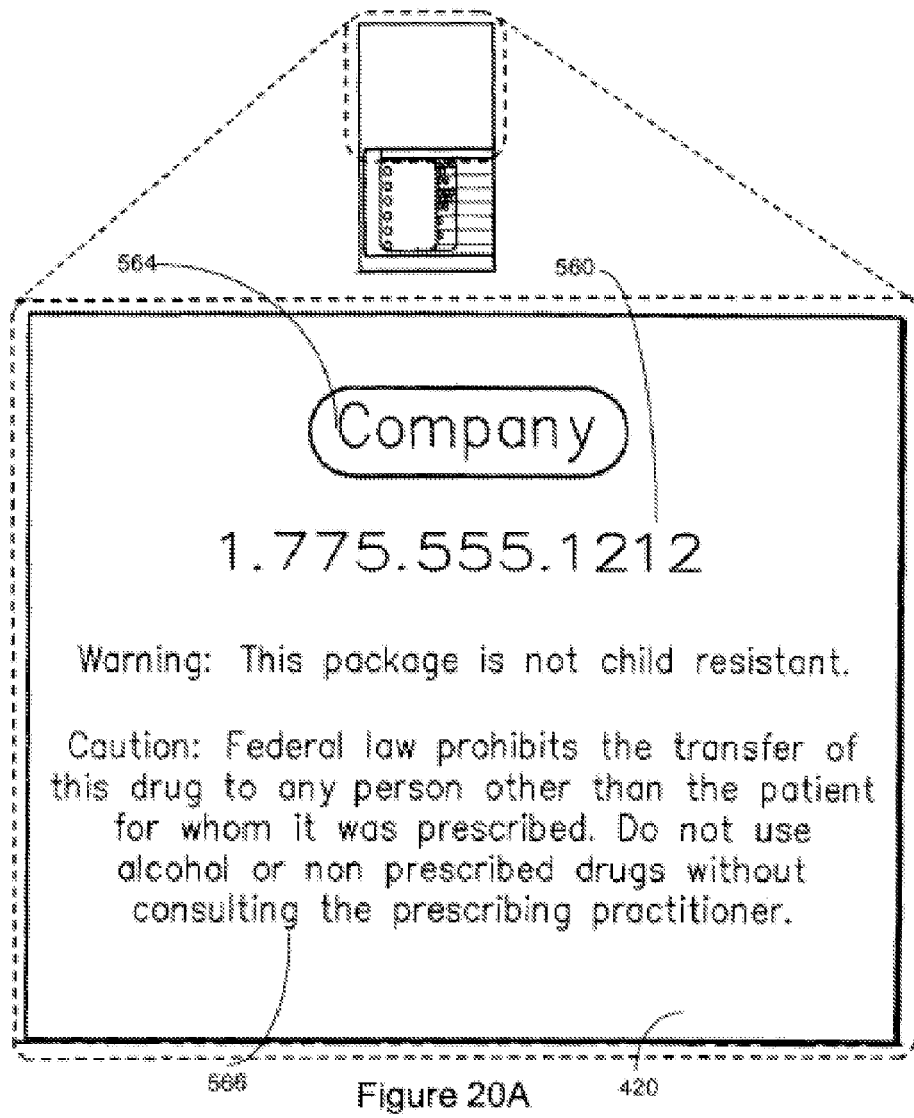
FIGS. 20A-20B show a third side view of the illustrative right-side wall of the 30-day tablet dispensing container.
Figure 20B:
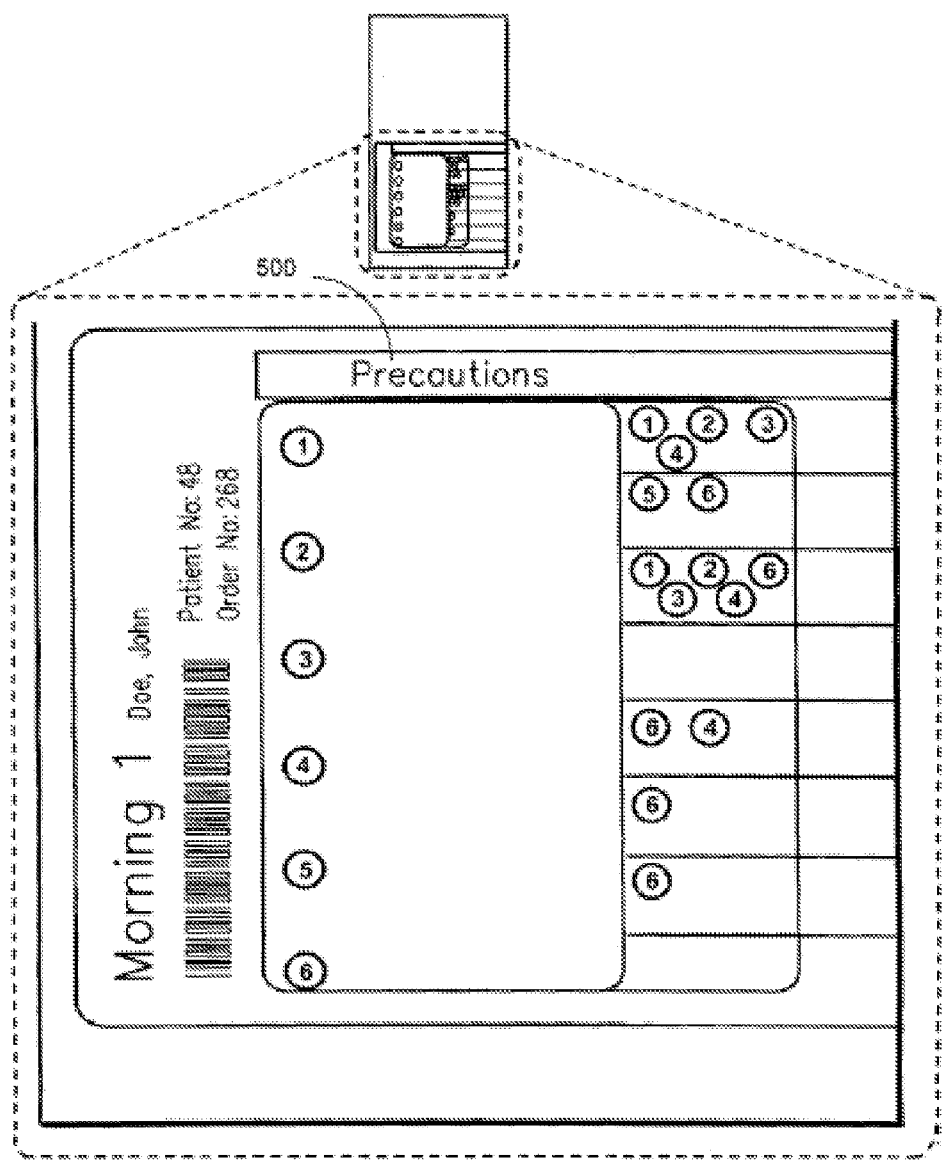

Referring to FIGS. 20A-20B, there is shown a side view of the illustrative right-side wall of the 30-day tablet dispensing container. The visible portion of primary label 500 is affixed to the lower portion of right side wall 420. The visible label portion includes the time period 502, patient name 504, barcode 506, patient number 508, order number 510, numbers 512A associated with precautions 514 (not shown), and numbers 512B. In this illustrative embodiment, the upper portion of the right side 420 includes pharmacy name 564 and contact telephone/facsimile number 560. In this illustrative embodiment, the right side 420 also includes certain additional legal information or warnings 566 regarding the package and its contents.

During the process of assembling and filling the 30-day tablet dispensing container, bar code 558 may be printed or affixed to the back of an assembled, unfilled container before any other patient-specific information is applied. Then, as the process continues, barcode 506 from the illustrative label 500 may be compared to barcode 558 that is already present on the unfilled container before the label 500 is affixed to the container. Lastly, the barcode 564 that is found on the back of each tablet pouch may be compared with the barcode 506 disposed on the label 500 and/or the barcode 558 disposed on the back side of the container. If the barcodes are properly associated, i.e. they "match", then the strip of packets will be placed into the associated container before sealing the container. The barcode scanning can be accomplished with handheld devices or may be automated.

Figure 21:
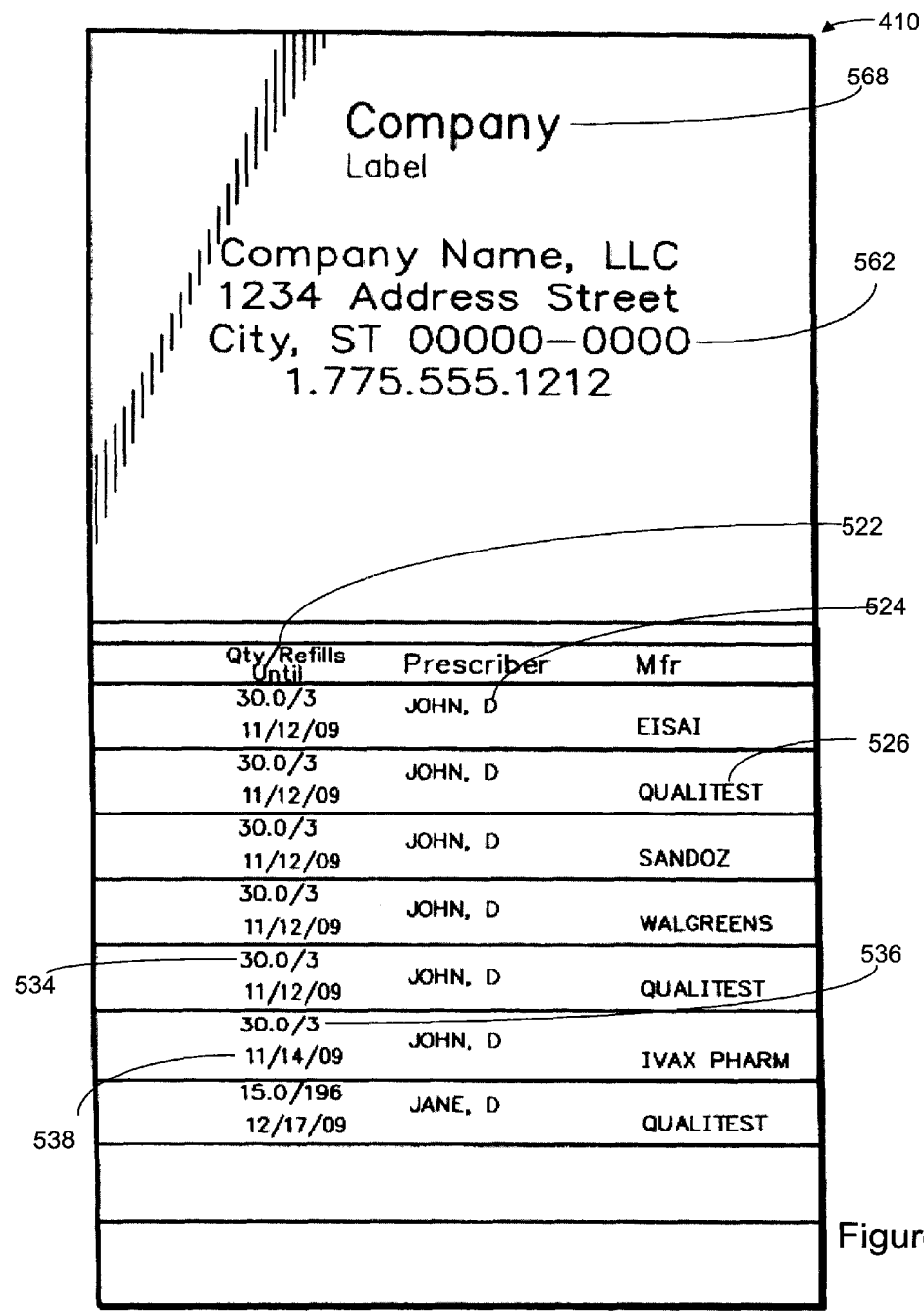
FIG. 21 shows a fourth side view of the illustrative left-side wall of the 30-day tablet dispensing container.

Referring to FIG. 21 there is shown a side view of the illustrative left-side wall of the 30-day tablet dispensing container. The visible portion of primary label 500 is affixed to the lower portion of left side wall 410. The label portion includes the refill information 522 including quantity 534, number of refills 536, the date 538 that the prescription is good through, prescribing practitioner names 524, and manufacturer information 526. In this illustrative embodiment, the upper portion of the left side 410 includes illustrative pharmacy name 568 and contact address 562.

Figure 22:
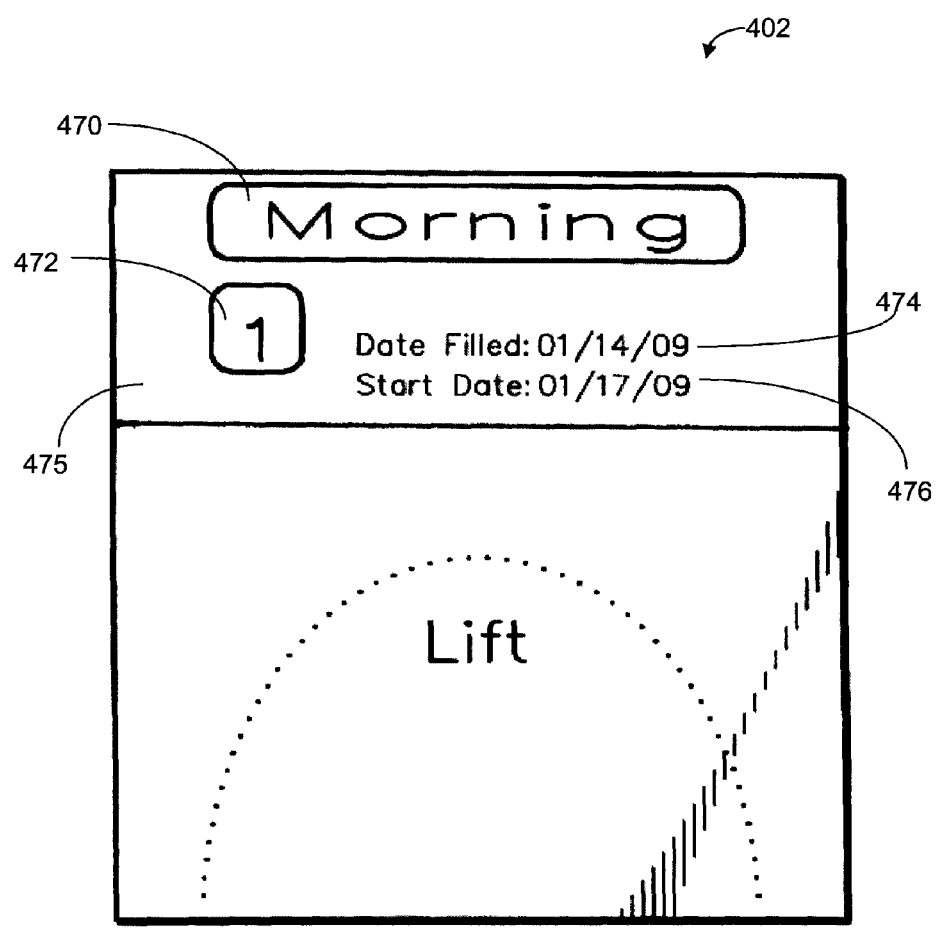
FIG. 22 shows a top view of the top wall of the unopened 30-day tablet dispensing container.
Figure 23:
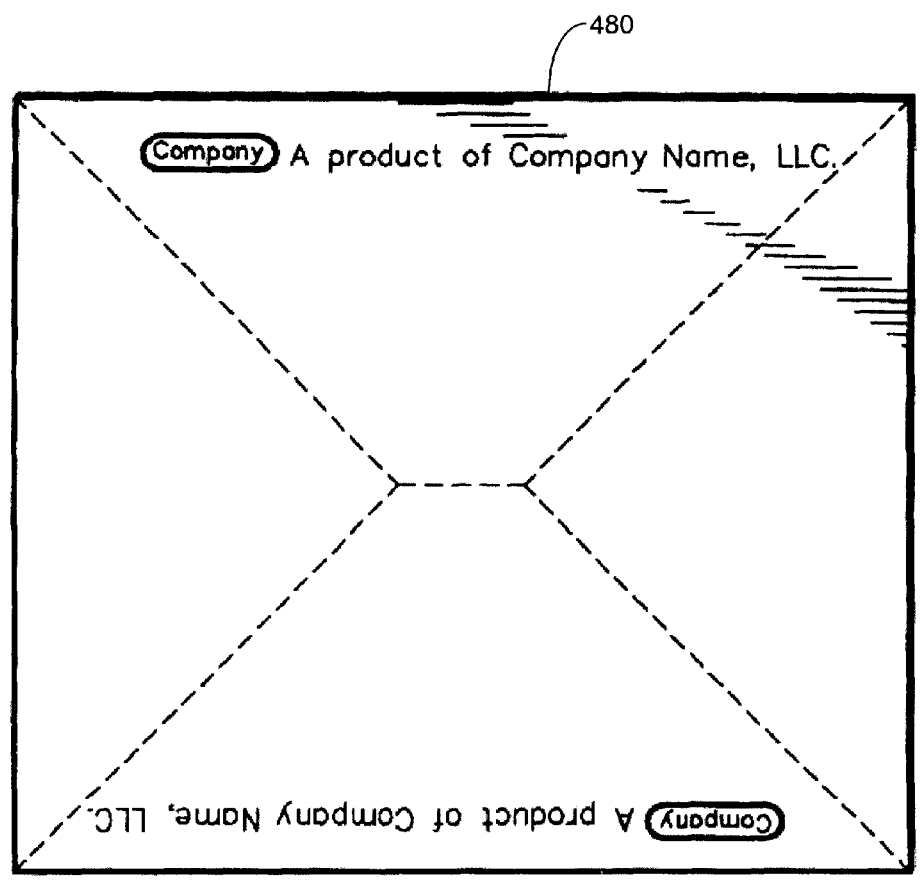
FIG. 23 shows a bottom view of the 30-day tablet dispensing container.

In FIG. 22 there is shown a top view of the top wall of the unopened 30-day tablet dispensing container. The top wall 402 includes the dosage period 470, the dosage period number 472, the date 474 that the prescription was filled, and the date 476 that marks the first day of the about 30-day period during which the enclosed medicaments should be taken. A bottom view of the 30-day tablet dispensing container is shown in FIG. 23 that includes folded elements and glued elements of the container that make up the bottom wall 480 when the foldable box is assembled.

Figure 24:
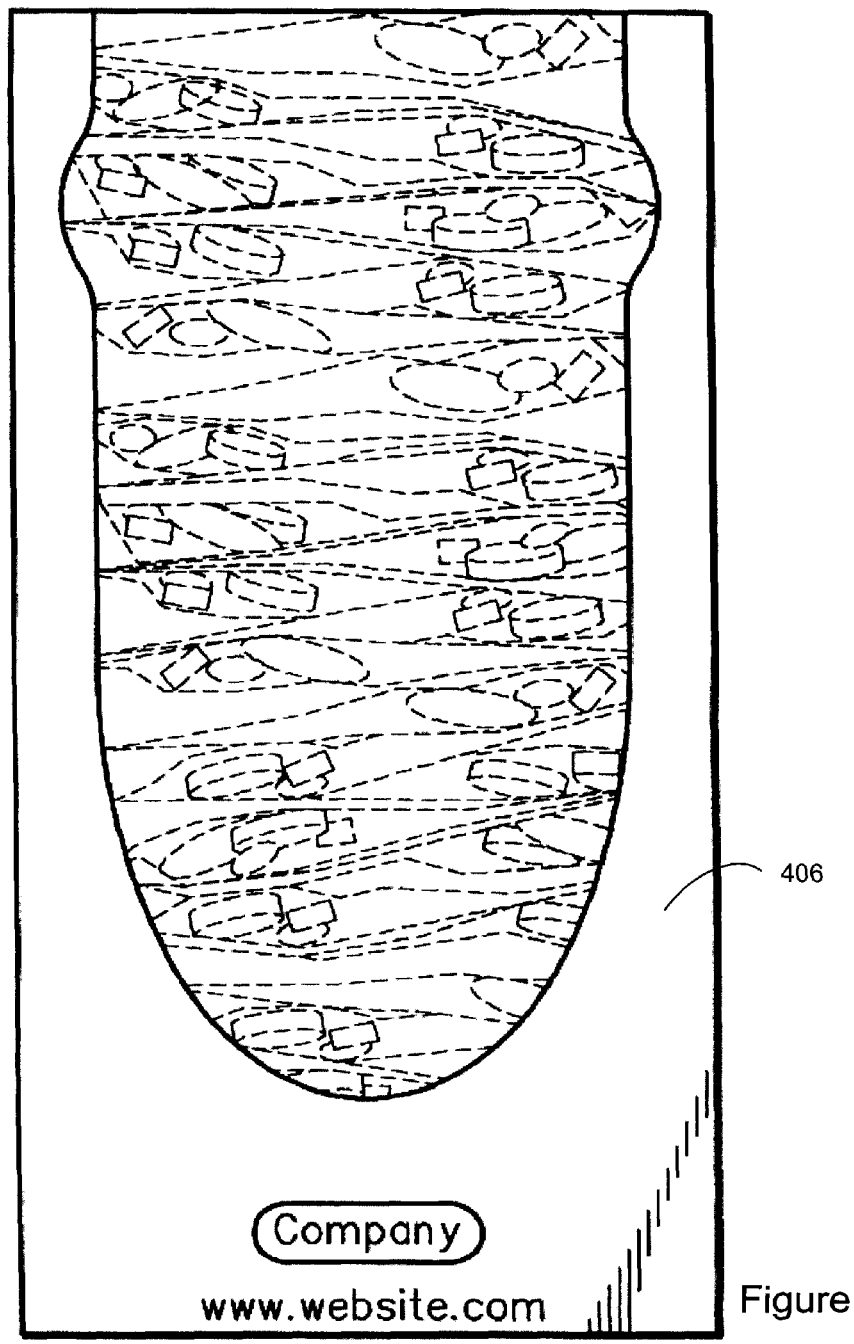
FIG. 24 shows an illustrative front view of the opened 30-day tablet dispensing container that reveals illustrative pouches.

Referring to FIG. 24 there is shown an illustrative front view of the opened 30-day tablet dispensing container that reveals illustrative pouches where the front lid 404 (not shown) has been removed to reveal medicament packets within. Typically, the lid is removed after the user verifies that the medications are prescribed to the person that is about to take the medication by checking the patient name. The user would then verify that the time period on the illustrative container 400 corresponds to the current time of day. If this is the first time the container has been used, the illustrative user would then remove the lid 404 from the top 402 and/or the front 406 of the illustrative container 400 to reveal the contents. Next, the user would reach into the container and remove the first packet or pouch that contains medicaments. The user would then verify that the pouch or packet has the current date before opening the pouch. While the user may also re-verify that the pouch or packet also has the correct patient name and dosage period, this step is unnecessary due to the barcode verification (described above) used during the filling process.

Once the user has verified that the pouch removed from the container is for the correct person, date, and time period, the user may then open the pouch. The user will then administer the medication to the patient (himself or someone else). The patient will take the medication and discard the empty pouch. The process will be repeated for the next dosage period, such as mid-day.

The illustrative pouch described above can be opened with only one hand, making it easier for even for those with limited motion to self-administer even complex medication regimens. In this way, the 30-day tablet dispensing container system described herein provides a compliance mechanism that is simple to understand and intuitive to use for patients and caregivers alike.

The illustrative 30-day tablet dispensing container offers additional benefits for those with a variety of conditions that affect speech and/or upper limb mobility, including but not limited to disorders like arthritis, effects of a stroke, or early stage dementia. Many of these patients develop their conditions later in life, and these patients may dislike relying on a caregiver to provide information to physicians or to self-administer complex medication regimens. The 30-day tablet dispensing container system helps these patients address both issues. For a patient, the illustrative 30-day tablet dispensing container provides drug regimen information and facilitates communication with a physician, a nurse, a third party, a spouse, a caregiver, or other such individual. The 30-day tablet dispensing container also allows the illustrative patient to maintain independence by taking charge of their own medications.

It is to be understood that the detailed description of illustrative embodiments are provided for illustrative purposes. The scope of the claims is not limited to these specific embodiments or examples. The foldable box holding a plurality of pouches, manufacturing separable pouches with a center cut blade, and patient medication management system provides patients or caregivers with the peace of mind of knowing that the right medication will be taken at the right dosage period each day. Thus, the patient medication management system and method removes the worries surrounding medication mishaps and enabling the patient to live independently longer. Various structural limitations, elements, details, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. A system of manufacturing a plurality of separable pouches comprising:
   a plurality of sealed pouches, in which a heated roller is configured to seal each pouch and each pouch includes a plurality of different tablets corresponding to different medications,
   each sealed pouch includes a sealed top end, a sealed bottom end, and two sides, where at least one side is also sealed;
   a center cut blade configured to be affixed to the heated roller that separates each sealed pouch, the center cut blade comprising:
      a side cut on each end of the blade,
      a center cut in the middle of the blade, and
      a plurality of perforation cuts between each side cut and center cut;
   wherein the plurality of sealed pouches comprises thirty filled pouches that are received by a foldable box that includes,
      a top wall having one end fixedly coupled to the foldable box and an opposite end that provides a foldable lid;
      a front-side wall having a removable lid that is bordered by a plurality of perforations;
      a right-side wall that abuts the front-side wall and the top wall;
      a back-side wall that abuts the right-side wall and the top wall;
      a left-side wall that is between the back-side wall and the front-side wall, the left-side wall configured to abut the top wall;
      a bottom wall that abuts the front-side wall, the right-side wall, the back-side wall, and the left-side wall;
      a cavity defined by the front-side wall, the right-side wall, the back-side wall, the left-side wall and the bottom wall;
   a barcode associated with one of the pouches, wherein the barcode is associated with the prescription;
   a label affixed to the foldable box, wherein the label includes a description of the medications and the barcode associated with the prescription;
   wherein the cavity is configured to receive the plurality of filled pouches that are associated with the barcode; and
   wherein one of the walls is configured to receive the label associated with the bar code.

2. The system of claim 1, wherein the filled pouches also include one empty pouch that provides a reminder to re-order medications.

3. The system of claim 1, wherein each sealed pouch includes a side cut on each side of a top end and a bottom end of the sealed pouch, a center cut on the top end and the bottom end of the sealed pouch, and at least one perforation between each side cut and the center cut.

4. The system of claim 3, further comprising at least three perforations between each side cut and the center cut.

5. The system of claim 4, further comprising at least four ribbons between each side cut and the center cut, wherein the first ribbon is disposed between the side cut and the first perforation, the second ribbon and third ribbon are each disposed between perforations, and the fourth ribbon is disposed between the third perforation and the center cut.

6. The system of claim 1, further comprising a heated roller configured to seal each pouch.

7. The system of claim 1, wherein the center cut length is greater than the length of each side cut.

8. The system of claim 1, wherein the thirty pouches correspond to a thirty day supply of medications.

9. The system of claim 1, wherein twenty-eight filled pouches correspond to a four-week supply of medications, the twenty-eight filled pouches adjacent to an empty pouch that provides a reminder to re-order medications, the empty pouch further adjacent to two filled pouches.

10. The system of claim 1, wherein each pouch includes a printed date and a printed period.

11. A system of manufacturing a plurality of separable pouches comprising:
   a plurality of sealed pouches, in which a heated roller is configured to seal each pouch and each pouch includes a plurality of different tablets corresponding to different medications,
   each sealed pouch includes a sealed top end, a sealed bottom end, and two sides, where at least one side is also sealed;
   a center cut blade configured to be affixed to the heated roller that separates each sealed pouch, the center cut blade comprising:
      a side cut on each end of the blade,
      a center cut in the middle of the blade, and
      a plurality of perforation cuts between each side cut and center cut;
   wherein the plurality of sealed pouches comprises seven filled pouches that are received by a foldable box that includes,
      a top wall having one end fixedly coupled to the foldable box and an opposite end that provides a foldable lid;
      a front-side wall having a removable lid that is bordered by a plurality of perforations;
      a right-side wall that abuts the front-side wall and the top wall;
      a back-side wall that abuts the right-side wall and the top wall;
      a left-side wall that is between the back-side wall and the front-side wall, the left-side wall configured to abut the top wall;
      a bottom wall that abuts the front-side wall, the right-side wall, the back-side wall, and the left-side wall;
      a cavity defined by the front-side wall, the right-side wall, the back-side wall, the left-side wall and the bottom wall;
   a barcode associated with one of the pouches, wherein the barcode is associated with the prescription;
   a label affixed to the foldable box, wherein the label includes a description of the medications and the barcode associated with the prescription;
   wherein the cavity is configured to receive the plurality of filled pouches that are associated with the barcode; and
   wherein one of the walls is configured to receive the label associated with the bar code.

12. The system of claim 11, wherein each sealed pouch includes a side cut on each side of a top end and a bottom end of the sealed pouch, a center cut on the top end and the bottom end of the sealed pouch, and at least one perforation between each side cut and the center cut.

13. The system of claim 12, further comprising at least three perforations between each side cut and the center cut.

14. The system of claim 13, further comprising at least four ribbons between each side cut and the center cut, wherein the first ribbon is disposed between the side cut and the first perforation, the second ribbon and third ribbon are each disposed between perforations, and the fourth ribbon is disposed between the third perforation and the center cut.

15. The system of claim 11, further comprising a heated roller configured to seal each pouch.

16. The system of claim 11, wherein the center cut length is greater than the length of each side cut.

17. The system of claim 11, wherein each pouch includes a printed date and a printed period.

18. A method for manufacturing a plurality of separable pouches, comprising:
 forming a plurality of sealed pouches;
 sealing each pouch with a heat roller, in which each pouch includes a plurality of different tablets corresponding to different medications,
 each sealed pouch including a sealed top end, a sealed bottom end, and two sides, where at least one side is also sealed;
 wherein a center cut blade is affixed to the heated roller that separates each sealed pouch, wherein the center cut blade comprises:
  a side cut on each end of the blade,
  a center cut in the middle of the blade, and
  a plurality of perforation cuts between each side cut and center cut; and
 wherein each sealed pouch is joined to an adjacent pouch by a plurality of tearable ribbons, wherein each sealed pouch comprises:
  a side cut on each side of the top end and bottom end sealed pouch,
  a center cut on the top end and bottom end of the sealed pouch, and
  a plurality of perforations between each side cut and the center cut;
 receiving at least seven filled pouches in a foldable box that includes,
  a top wall having one end fixedly coupled to the foldable box and an opposite end that provides a foldable lid;
  a front side wall having a removable lid that is bordered by a plurality of perforations;
  a right-side wall that abuts the front side wall and the top wall;
  a back side wall that abuts the right-side wall and the top wall;
  a left-side wall that is between the back side wall and the front side wall, the left-side wall configured to abut the top wall;
  a bottom wall that abuts the front side wall, the right-side wall, the back side wall, and the left-side wall;
  a cavity defined by the front side wall, the right-side wall, the back side wall, the left-side wall, and the bottom wall;
 a barcode associated with one of the pouches, wherein the barcode is associated with the prescription;
 a label affixed to the foldable box, wherein the label includes a description of the medications and the barcode associated with the prescription;
 wherein the cavity is configured to receive the plurality of filled pouches that are associated with the barcode; and
 wherein one of the walls is configured to receive the label associated with the bar code.

19. The method of claim 18, wherein the step of receiving further comprises receiving thirty filled pouches in the foldable box.

20. The method of claim 19, wherein the thirty filled pouches include twenty-eight filled pouches corresponding to a four week supply of medications, an empty pouch adjacent to the twenty-eight filled pouches and providing a reminder to re-order medications, the empty pouch further adjacent to two filled pouches.

* * * * *